US012030905B2

(12) United States Patent
Carlson et al.

(10) Patent No.: US 12,030,905 B2

(45) **Date of Patent: *Jul. 9, 2024**

(54) STEVIOL GLYCOSIDE COMPOUNDS, COMPOSITIONS FOR ORAL INGESTION OR USE, AND METHOD FOR ENHANCING STEVIOL GLYCOSIDE SOLUBILITY

(71) Applicant: Cargill, Incorporated, Wayzata, MN (US)

(72) Inventors: Ting Liu Carlson, Marietta, SC (US); Dan Gaspard, Excelsior, MN (US)

(73) Assignee: Carghill, Incorporated, Wayzata, MN (US)

( * ) Notice: Subject to any disclaimer, the term of this patent is extended or adjusted under 35 U.S.C. 154(b) by 116 days.

This patent is subject to a terminal disclaimer.

(21) Appl. No.: 17/856,460

(22) Filed: Jul. 1, 2022

(65) Prior Publication Data

US 2023/0044540 A1 Feb. 9, 2023

Related U.S. Application Data

(63) Continuation of application No. 17/120,739, filed on Dec. 14, 2020, now Pat. No. 11,407,780, which is a continuation of application No. 16/553,200, filed on Aug. 28, 2019, now Pat. No. 10,906,927, which is a continuation of application No. 15/536,385, filed as application No. PCT/US2015/066419 on Dec. 17, 2015, now Pat. No. 10,711,024.

(60) Provisional application No. 62/093,213, filed on Dec. 17, 2014.

(51) Int. Cl.

| | |
|---|---|
| ***C07H 15/256*** | (2006.01) |
| ***A23L 2/56*** | (2006.01) |
| ***A23L 2/60*** | (2006.01) |
| ***A23L 27/00*** | (2016.01) |
| ***A23L 27/30*** | (2016.01) |

(52) U.S. Cl.

CPC .............. *C07H 15/256* (2013.01); *A23L 2/56* (2013.01); *A23L 2/60* (2013.01); *A23L 27/36* (2016.08); *A23L 27/88* (2016.08)

(58) Field of Classification Search

None

See application file for complete search history.

(56) References Cited

U.S. PATENT DOCUMENTS

| | | | |
|---|---|---|---|
| 6,180,157 | B1 | 1/2001 | Fotos et al. |
| 6,365,216 | B1 | 4/2002 | Dron et al. |
| 9,522,929 | B2 | 12/2016 | Mao et al. |
| 9,527,880 | B2 | 12/2016 | Mao et al. |
| 9,567,619 | B2 | 2/2017 | Mao et al. |
| 9,643,990 | B2 | 5/2017 | Mao et al. |
| 9,783,566 | B2 | 10/2017 | Mao et al. |
| 9,850,270 | B2 | 12/2017 | Mao et al. |
| 2006/0083838 | A1 | 4/2006 | Jackson et al. |
| 2009/0162500 | A1 | 6/2009 | Mui et al. |
| 2011/0033525 | A1 | 2/2011 | Liu et al. |
| 2011/0183056 | A1 | 7/2011 | Morita et al. |
| 2013/0209658 | A1 | 8/2013 | Spelman et al. |
| 2013/0251881 | A1 | 9/2013 | Mutilangi et al. |
| 2013/0309389 | A1 | 11/2013 | Carlson et al. |
| 2014/0171519 | A1 | 6/2014 | Prakash et al. |
| 2014/0227421 | A1 | 8/2014 | Markosyan |
| 2014/0296499 | A1 | 10/2014 | Chen et al. |
| 2014/0329281 | A1 | 11/2014 | Houghton-Larsen et al. |
| 2014/0342043 | A1 | 11/2014 | Bell et al. |
| 2014/0343262 | A1 | 11/2014 | Prakash et al. |
| 2015/0257424 | A1 | 9/2015 | Catani et al. |
| 2016/0039856 | A1 | 2/2016 | Prakash et al. |
| 2017/0362268 | A1 | 12/2017 | Carlson et al. |

FOREIGN PATENT DOCUMENTS

| | | |
|---|---|---|
| CN | 103404833 | 11/2013 |
| EP | 3383201 | 10/2018 |
| JP | H01319494 A | 12/1989 |
| JP | 2001048727 | 2/2001 |
| JP | 2012504552 | 2/2012 |
| WO | WO0160842 | 8/2001 |
| WO | WO2010038911 | 4/2010 |
| WO | WO2010151653 | 12/2010 |
| WO | WO2013022989 | 2/2013 |

(Continued)

OTHER PUBLICATIONS

International Search Report dated Feb. 16, 2017 for PCT/US2016/064274 filed Nov. 30, 2016 (2 pgs).

International Search Report dated Sep. 15, 2017 for PCT/US2017/037868 filed Jun. 16, 2017 (2 pgs).

International Search Report dated Feb. 17, 2017 of PCT/US2016/064227 filed Nov. 30, 2016 (2 pages).

FDA GRAS Notice (GRN) No. 626; http://www.fda.gov/Food/IngredientsPackagingLabeling/GRAS/NoticeInventory/default.htm. (68 pages)(2016).

Prakash et al., "Development of Next Generation Slevia Sweetener: Rebaudioside M," Foods, 3(1):162-175 (2014).

(Continued)

*Primary Examiner* — Layla D Berry

(74) *Attorney, Agent, or Firm* — McDonnell Boehnen Hulbert & Berghoff LLP

(57) ABSTRACT

Novel steviol glycoside compounds characterized by a first group of four glucopyranose residues attached via the number 13 carbon (C13) of the steviol moiety and a second group of two or three glucopyranose residues attached via the number 19 carbon (C19) of the steviol moiety are described, and exemplified by compounds 1-4. These compounds can be present in a composition with other steviol glycosides (e.g., Reb D and Reb M) to enhance their solubilities. Accordingly, the novel compounds can facilitate the preparation of aqueous compositions having a higher concentration of steviol glycosides. A steviol glycoside composition including one or more of compounds 1-4 can be used as a sweetener composition to sweeten other compositions (sweetenable compositions) such as foods, beverages, medicines, oral hygiene compositions, nutraceuticals, and the like.

13 Claims, 24 Drawing Sheets

(56) References Cited

FOREIGN PATENT DOCUMENTS

| | | |
|---|---|---|
| WO | WO2013066490 | 5/2013 |
| WO | WO2013096420 | 6/2013 |
| WO | WO2013148177 | 10/2013 |
| WO | WO2014052457 | 4/2014 |
| WO | WO2014086890 | 6/2014 |
| WO | WO2014122227 | 8/2014 |
| WO | WO2014122328 | 8/2014 |
| WO | WO2014146135 | 9/2014 |
| WO | WO2014172055 | 10/2014 |
| WO | WO2014191581 | 12/2014 |
| WO | WO2014193888 | 12/2014 |
| WO | WO2014193889 | 12/2014 |
| WO | WO2014193934 | 12/2014 |
| WO | WO2015006764 | 1/2015 |
| WO | WO2015023928 | 2/2015 |
| WO | WO2015051454 | 4/2015 |
| WO | WO2015065650 | 5/2015 |
| WO | WO2015171555 | 11/2015 |
| WO | WO2016023844 | 2/2016 |
| WO | WO2016028899 | 2/2016 |
| WO | WO2016043926 | 3/2016 |
| WO | WO2016054534 | 4/2016 |
| WO | WO2016054548 | 4/2016 |
| WO | WO2016086233 | 6/2016 |
| WO | WO2016100689 | 6/2016 |
| WO | WO2016120486 | 8/2016 |
| WO | WO2016156616 | 10/2016 |
| WO | WO2017095932 | 6/2017 |
| WO | WO2017198682 | 11/2017 |

OTHER PUBLICATIONS

Chaturvedula, et al., "Utilization of RP-HPLC fingerprinting analysis for identification of diterpene glycosides from stevia rebaudinana," Int. J. Res. Phytochem Pharmacol., 1(2):88-92 (2011).

Chaturvedula, et al., "A new diterpene glycoside from Stevia rebaudiana," Molecules, 16(4):2937-43 (2011).

Chaturvedula, et al., "Diterpene Glycosides from Stevia rebaudiana," Molecules, 28;16(5):3552-62 (2011).

Chaturvedula, et al., "IR Spectral Analysis of Diterpene Glycosides Isolated from Stevia rebaudiana," Food Nutr Sci, 3:1467-1471 (2012).

Chaturvedula, et al., "NMR Spectral Analysis and Hydrolysis Studies of Rebaudioside N, a Minor Steviol Glycoside of Stevia rebaudiana Bertoni," Food and Nutrition Sciences, 4, 1004-1008 (2013).

Prakash, et al., "Bioconversion of Rebaudioside I from Rebaudioside A," Molecules, 19:17345-17355 (2014).

Prakash, et al, "Isolation and Characterization of a Novel Rebaudioside M Isomer from a Bioconversion Reaction of Rebaudioside A and NMR Comparison Studies of Rebaudioside M Isolated from Stevia rebaudiana Bertoni and Stevia rebaudiana Morita," Biomolecules, 4(2):374-389 (2014).

Prakash, et al, "Structural Characterization of the Degradation Products of a Minor Natural Sweet Diterpene Glycoside Rebaudioside M under Acidic Conditions," Int. J. Mol. Sci. 15:1014-1025 (2014).

Prakash, et al., "Additional Minor Diterpene Glycosides from Stevia rebaudiana Bertoni," Molecules, 18:13510-13519 (2013).

Prakash et al., "Catalytic Hydrogenation of the Sweet Principles of Stevia rebaudiana, Rebaudioside B, Rebaudioside C, and Rebaudioside D and Sensory Evaluation of Their Reduced Derivatives," Int. J. Mol. Sci., 13, 15126-15136 (2012).

Chaturvedula, et al, "Minor diterpenoid glycosides from the leaves of Stevia rebaudiana," Phytochemistry Letters, 4:209-212 (2011).

Chaturvedula, et al., "Structure of the novel a-glucosyl linked diterpene glycoides from Stevia rebaudiana," Carboydrate Research, 346:2034-2038 (2011).

Chaturvedula, et al., "Structures of the novel diterpene glycosides from Stevia rebaudiana," Carbohydrate Research, 346:1057-1060 (2011).

Prakash, et al., "Stability of rabaudioside A under acidic conditions and its degradation products," Food Research International, 48:65-75 (2012).

Starratt, et al., "Rebaudioside F, a diterpene glycoside from Stevia rebaudiana", Phytochemistry, 59:367-370 (2002).

Prakash, et al., "Structural Characterization And Hydrolysis Studies Of Rebaudioside E, A Minor Sweet Component Of Stevia Rebaudiana," Eur. Chem. Bull., 2(5), 298-302 (2013).

Chaturvedula, et al. "Additional Minor Diterpene Glycosides from Stevia rebaudiana Bertoni," Nat Prod Commun., 6(8):1059-62 (2011).

Chaturvedula et al., "Isolation and Structural Characterization of a New Minor Penta β-D-Glucopyranosyl Diterpene from Stevia rebaudiana Bertoni," American Journal of Plant Sciences, 5, 3519-3525 (2014).

Prakash et al., "A New Diterpene Glycoside: 15α-Hydroxy-Rebaudioside M Isolated from Stevia rebaudiana," Nat Prod Commun. 10(7):1159-61 (2015).

Ibrahim et al., "Minor Diterpene Glycosides from the Leaves of Stevia rebaudiana," J. Natural Prod. 77:1231 (2014).

EFSA Panel on Food Additives and Nutrient Sources added to Food (ANS), "Scientific Opinion on the safety of steviol glycosides for the proposed uses as a food additive," EFSA Journal 8(4):1537 (2010).

EFSA Panel on Food Additives and Nutrient Sources added to Food, "Scientific opinion on the safety of the proposed amendment of the specifications for steviol glycosides (E 960) as a food additive," EFSA Journal 13(12):4316 (2015).

EFSA Panel on Food Additives and Nutrient Sources added to Food (ANS), "Scientific opinion on the safety of the extension of use of steviol glycosides (E 960) as a food additive," EFSA Journal 13(6):4146 (2015).

Final Office Action issued in U.S. Appl. No. 15/536,385; dated Sep. 26, 2019, pp. 1-9.

Non-Final Office Action issued in U.S. Appl. No. 16/310,746; dated Jun. 8, 2021, pp. 1-10.

Non-Final Office Action issued in U.S. Appl. No. 16/310,779; dated Jun. 8, 2021, pp. 1-14.

Non-Final Office Action issued in U.S. Appl. No. 15/779,761; dated Jun. 8, 2021, pp. 1-13.

Final Office Action issued in U.S. Appl. No. 16/310,746; dated Dec. 1, 2021, pp. 1-14.

Final Office Action issued in U.S. Appl. No. 16/310,779; dated Nov. 30, 2021, pp. 1-15.

Final Office Action issued in U.S. Appl. No. 15/779,761; dated Nov. 29, 2021, pp. 1-12.

FDA GRAS Not1ce (GRN) No. 626; http://www.fda.gov/Food/IngredientsPackagingLabeling/GRAS/NoticeInventory/default.htm. (68 pages).

International Search Report dated Mar. 3, 2016 for International Application No. PCT/US2015/066419 (3 pages).

Third Party Observation submitted Oct. 17, 2018 for European Application No. 17814167.7 (6 pages).

Kusama et al., "Transglucosylation into stevioside by the enzyme system from *Streptomyces* sp.," Agric. Biol. Chem. 50(10):2445-51 (Oct. 1986).

International Preliminary Report on Patentability from then International Search Authority for International Application No. PCT/US2016/064274; dated Dec. 18, 2018 pp. 1-9.

International Preliminary Report on Patentability from then International Search Authority for International Application No. PCT/US2017/037868; dated Sep. 15, 2017 pp. 1-7.

International Preliminary Report on Patentability from then International Search Authority for International Application No. PCT/US2016/064227; dated Jun. 5, 2018 pp. 1-7.

Extended European Search Report and Opinion issued by the European Patent Office for European Application No. 15871082.2, dated Jul. 24, 2018 (pp. 1-7).

Extended European Search Report and Opinion issued by the European Patent Office for European Application No. 16905680.1, dated Feb. 28, 2020 (pp. 1-10).

(56) References Cited

OTHER PUBLICATIONS

Extended European Search Report and Opinion issued by the European Patent Office for European Application No. 17814167.7, dated Mar. 17, 2020 (pp. 1-4).
Extended European Search Report and Opinion issued by the European Patent Office for European Application No. 16871428.5, dated Apr. 25, 2019 (pp. 1-5).
Third Party Observation submitted Aug. 21, 2019 for European Application No. 15871082.2 (39 pages).
Third Party Observation submitted Jan. 11, 2019 for European Application No. 16905680.1 (5 pages).
Third Party Submission submitted Mar. 14, 2018 for U.S. Appl. No. 15/536,385 (58 pages).
Ohta et al., "Characterization of Novel Steviol Glycosides from leaves of Stevia rebaudiana Morita", Journal of Applied Glycoscience, The Japanese Society of Applied Glycoscience, Aug. 17, 2010, Issue 57, pp. 199-209.
Prakash et al., "Isolation, characterization and sensory evaluation of a Hexa beta-D-glucopyranosyl diterpene from Stevia rebaudiana," Nat Prod Commun. 8(11):1523-6 (2013).
Prakash et al., "Catalytic hydrogenation of the sweet principles of Stevia rebaudiana, Rebaudioside B, Rebaudioside C, and Rebaudioside D and sensory evaluation of their reduced derivatives," Int J Mol Sci. 13(11):15126-36 (2012).
Verduyn, C. et al., "Effect of benzoic acid on metabolic fluxes in yeasts: a continuous-culture study on the regulation of respiration and alcoholic fermentation," Yeast 8, 501-517 (1992).
International Preliminary Report on Patentability from then International Search Authority for International Application No. PCT/US2015/066419; dated Jun. 20, 2017 pp. 1-8.
Non-Final Office Action issued in U.S. Appl. No. 15/536,385; dated Oct. 10, 2018, pp. 1-7.
Final Office Action issued in U.S. Appl. No. 15/536,385; dated Mar. 28, 2019, pp. 1-8.
EPO Communication issued in European Patent Application No. 16 905 680.1 dated Sep. 29, 2023.

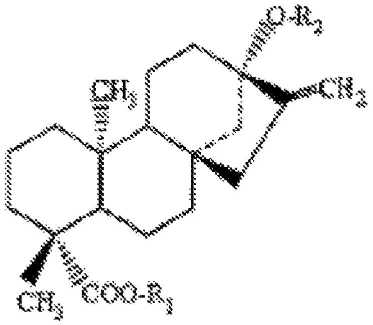

| Compound name | $R_1$ (C-19) | $R_2$ (C-13) |
|---|---|---|
| 1. Steviol | H | H |
| 2. Steviolmonoside | H | β-Glc |
| 3. Rubusoside | β-Glc | β-Glc |
| 4. Steviolbioside | H | β-Glc-β-Glc(2→1) |
| 5. Stevioside | β-Glc | β-Glc-β-Glc(2→1) |
| 6. Rebaudioside A | β-Glc | β-Glc-β-Glc(2→1)<br>β-Glc(3→1) |
| 7. Rebaudioside B | H | β-Glc-β-Glc(2→1)<br>β-Glc(3→1) |
| 8. Rebaudioside C (Dulcoside B) | β-Glc | β-Glc-α-Rha(2→1)<br>β-Glc(3→1) |
| 9. Rebaudioside D | β-Glc-β-Glc(2→1) | β-Glc-β-Glc(2→1)<br>β-Glc(3→1) |
| 10. Rebaudioside E | β-Glc-β-Glc(2→1) | β-Glc-β-Glc(2→1) |
| 11. Rebaudioside F | β-Glc | β-Glc-β-Xyl(2→1)<br>β-Glc(3→1) |
| 12. Dulcoside A | β-Glc | β-Glc-α-Rha(2→1) |

| No. | Atom1 | Shift1 (ppm) | H's | Type | J (Hz) | Multiplet1 | (ppm) |
|---|---|---|---|---|---|---|---|
| 1 | 88, 6<'> | 0.74 | 4 | br s | - | M32 | [0.69 .. 0.78] |
| 2 | 7a | 0.88 | 1 | m | - | M31 | [0.81 .. 0.91] |
| 3 | 3<'> | 0.94 | 1 | m | - | M30 | [0.91 .. 0.96] |
| 4 | 4 | 1.00 | 1 | br d | 12.72 | M29 | [0.98 .. 1.04] |
| 5 | 90 | 1.11 | 3 | s | - | M28 | [1.07 .. 1.15] |
| 6 | 11<'>, 14<'>, 1<'>, 9<'> | 1.34 | 4 | m | - | M26 | [1.27 .. 1.38] |
| 7 | 13<''>, 9<''> | 1.42 | 2 | m | - | M27 | [1.38 .. 1.49] |
| 8 | 13<'>, 10<'> | 1.64 | 2 | m | - | M25 | [1.59 .. 1.67] |
| 9 | 8<''>, 1<''>, 10<''> | 1.72 | 3 | br d | 12.23 | M24 | [1.67 .. 1.76] |
| 10 | 14<''> | 1.82 | 1 | br s | - | M23 | [1.79 .. 1.85] |
| 11 | 16<'> | 1.96 | 1 | m | - | M22 | [1.89 .. 1.98] |
| 12 | 16<''>, 11<'> | 2.00 | 2 | m | - | M21 | [1.98 .. 2.04] |
| 13 | 2<''> | 2.10 | 1 | br d | 11.49 | M20 | [2.07 .. 2.14] |
| 14 | 31<ax> | 2.82 | 1 | m | - | M15 | [2.80 .. 2.85] |
| 15 | 65<ax>, 57<ax>, 35<ax>, 53<ax> | 3.06 | 4 | m | - | M14 | [3.03 .. 3.09] |
| 16 | 80<ax>, 83<ax>, 43<ax>, 55<ax>, 58<ax>, 28<ax>, 47<ax>, 33<ax> | 3.16 | 8 | m | - | M13 | [3.10 .. 3.21] |
| 17 | 45<ax>, 54<ax>, 74<ax>, 72<ax> | 3.26 | 4 | br dd | 17.34, 8.93 | M19 | [3.21 .. 3.28] |
| 18 | 49<ax> | 3.31 | 1 | m | - | M11 | [3.30 .. 3.32] |
| 19 | 68<ax>, 21<ax>, 22<ax> | 3.34 | 3 | br d | 4.65 | M18 | [3.32 .. 3.35] |
| 20 | 29<'> | 3.38 | 1 | m | - | M12 | [3.38 .. 3.40] |
| 21 | 81<'>, 41<'>, 58<'>, 70<'>, 24<ax> | 3.48 | 5 | m | - | M10 | [3.44 .. 3.54] |
| 22 | 50<'> | 3.62 | 1 | br s | - | M16 | [3.59 .. 3.64] |
| 23 | 81<''>, 41<''>, 58<''>, 76<ax>, 70<''>, 29<''> | 3.68 | 6 | m | - | M09 | [3.64 .. 3.74] |
| 24 | 23<ax> | 3.76 | 1 | br d | 8.96 | M17 | [3.74 .. 3.78] |
| 25 | 50<''> | 3.90 | 1 | br d | 11.25 | M06 | [3.88 .. 3.94] |
| 26 | 52<ax> | 4.24 | 1 | d | 7.82 | M05 | [4.22 .. 4.26] |
| 27 | 19<ax>, 38 | 4.57 | 2 | br d | 7.63 | M07 | [4.56 .. 4.59] |
| 28 | 78<ax> | 4.60 | 1 | br d | 7.58 | M08 | [4.59 .. 4.63] |
| 29 | 28<ax> | 4.70 | 1 | br d | 7.82 | M04 | [4.67 .. 4.72] |
| 30 | 17<a> | 4.76 | 1 | br s | - | M03 | [4.73 .. 4.79] |
| 31 | 17<b> | 5.02 | 1 | br s | - | M02 | [5.00 .. 5.05] |
| 32 | 67<ax> | 5.39 | 1 | br d | 7.34 | M01 | [5.37 .. 5.42] |

FIG. 4C

| F2 Atom | F2 (ppm) | F2 Atom | F2 (ppm) | F1 Atom | F1 (ppm) | F1 Atom | F1 (ppm) |
|---|---|---|---|---|---|---|---|
| 1<*> | 1.71 | 31<ax> | 2.91 | 1 | 19.9 | 31 | 71.8 |
| 1<'> | 1.31 | 33<ax> | 3.18 | | | 33 | 77.2 |
| 2<*> | 2.09 | 35<ax> | 3.01 | 2 | 37.7 | 35 | 75.4 |
| 2<'> | 0.85 | 36<ax> | 4.56 | | | 36 | 103.3 |
| | | 40<ax> | 3.33 | 3 | 44.8 | 40 | 77.8 |
| 4 | 0.99 | 41<*> | 3.69 | 4 | 57.4 | 41 | 61.9 |
| | | 41<'> | 3.46 | 5 | 40.3 | | |
| 6<*> | 1.71 | 43<ax> | 3.24 | 6 | 40.8 | 43 | 70.3 |
| 6<'> | 0.73 | 45<ax> | 3.23 | | | 45 | 76.9 |
| 7a | 0.87 | 47<ax> | 3.12 | 7 | 54 | 47 | 74.4 |
| | | 50<*> | 3.89 | 8 | 42.2 | 50 | 68.3 |
| 9<*> | 1.39 | 50<'> | 3.82 | 9 | 42.1 | | |
| 9<'> | 1.31 | 52<ax> | 4.23 | | | 52 | 103.9 |
| 10<*> | 1.72 | 53<ax> | 3.04 | 10 | 22.7 | 53 | 74.2 |
| 10<'> | 1.62 | 54<ax> | 3.18 | | | 54 | 77.2 |
| 11<*> | 2 | 55<ax> | 3.33 | 11 | 44.4 | 55 | 69.1 |
| 11<'> | 1.34 | 56<ax> | 3.3 | | | 56 | 77.2 |
| | | 58<*> | 3.68 | 12 | 88.4 | 58 | 62 |
| 13<*> | 1.61 | 58<'> | 3.46 | 13 | 38.3 | | |
| 13<'> | 1.38 | | | | | 64 | 178 |
| 14<*> | 1.82 | 67<ax> | 5.38 | 14 | 20.6 | 67 | 93.9 |
| 14<'> | 1.43 | 68<ax> | 3.23 | | | 68 | 76.9 |
| | | 70<*> | 3.64 | 15 | 153.2 | 70 | 61.6 |
| 16<*> | 1.89 | 70<'> | 3.5 | 16 | 47.4 | | |
| 16<'> | 1.84 | 72<ax> | 3.15 | | | 72 | 70.8 |
| 17<a> | 4.75 | 74<ax> | 3.66 | 17 | 105.8 | 74 | 77.2 |
| 17<b> | 5.02 | 76 | 3.65 | | | 76 | 78.4 |
| 19<ax> | 4.57 | 78<ax> | 4.59 | 19 | 96.4 | 78 | 103.3 |
| 21<ax> | 3.15 | 80<ax> | 3.33 | 21 | 77.6 | 80 | 75.6 |
| 22<ax> | 3.12 | 81<*> | 3.66 | 22 | 70.8 | 81 | 62.7 |
| 23<ax> | 3.75 | 81<'> | 3.37 | 23 | 86.5 | | |
| 24<ax> | 3.48 | 83<ax> | 3.06 | 24 | 79.6 | 83 | 71.3 |
| 25<ax> | 4.69 | 85<ax> | 3.18 | 25 | 103 | 85 | 77.2 |
| 26<ax> | 3.3 | 87<ax> | 3.05 | 26 | 77.2 | 87 | 75.1 |
| 29<*> | 3.71 | 89 | 0.73 | 29 | 62.1 | 89 | 17.1 |
| 29<'> | 3.69 | 90 | 1.1 | | | 90 | 23.2 |

ACD numbering

= $^{1}H$-$^{13}C$ HMBC

= $^{1}H$-$^{1}H$ COSY

= $^{1}H$-$^{1}H$ TOCSY spin system

Assigments were made on the basis of $^{1}H$-$^{1}H$ COSY, $^{1}H$-$^{1}H$ TOCSY, $^{1}H$-$^{13}C$ HSQC-DEPT, $^{1}H$-$^{13}C$ HMBC.

Numbering following IUPAC

FIG. 5B

| No. | Atom1 | Shift (ppm) | H's | Type | J (Hz) | Multiplet1 | (ppm) |
|---|---|---|---|---|---|---|---|
| 1 | 100, 6<> | 0.87 | 4 | s | - | M17 | [0.80 .. 0.93] |
| 2 | 7a | 0.99 | 1 | m | - | M18 | [0.96 .. 1.02] |
| 3 | 2<> | 1.06 | 1 | m | - | M19 | [1.02 .. 1.09] |
| 4 | 4 | 1.13 | 1 | m | - | M20 | [1.09 .. 1.16] |
| 5 | 101 | 1.34 | 3 | s | - | M21 | [1.17 .. 1.38] |
| 6 | 1<>, 9<> | 1.44 | 2 | br s | - | M22 | [1.38 .. 1.47] |
| 7 | 9<>, 14<>, 13<>, 11<> | 1.56 | 4 | m | - | M23 | [1.47 .. 1.65] |
| 8 | 10<> | 1.70 | 1 | m | - | M24 | [1.65 .. 1.75] |
| 9 | 14<>, 1<>, 6<>, 13<>, 10<> | 1.88 | 5 | br d | 10.51 | M25 | [1.78 .. 1.98] |
| 10 | 18<> | 2.05 | 1 | m | - | M26 | [2.00 .. 2.09] |
| 11 | 18<>, 11<> | 2.16 | 2 | m | - | M27 | [2.10 .. 2.22] |
| 12 | 2<> | 2.26 | 1 | m | - | M28 | [2.23 .. 2.30] |
| 13 | 31<ax> | 3.14 | 1 | br t | 9.41 | M16 | [3.10 .. 3.17] |
| 14 | 98<ax>, 35<ax>, 94<ax>, 53<ax> | 3.24 | 4 | m | - | M15 | [3.19 .. 3.30] |
| 15 | 40<ax>, 81<ax>, 78<ax>, 47<ax>, 65<ax>, 55<ax>, 91<ax>, 26<ax>, 56<ax>, 33<ax>, 96<ax>, 54< | 3.40 | 12 | m | - | M14 | [3.32 .. 3.47] |
| 16 | 45<ax>, 69<ax>, 21<ax>, 83<ax>, 43<ax> | 3.50 | 5 | m | - | M13 | [3.47 .. 3.54] |
| 17 | 29<>, 12<ax>, 22<ax>, 58<> | 3.58 | 4 | m | - | M12 | [3.54 .. 3.63] |
| 18 | 82<>, 70<>, 73<>, 41<>, 24<ax> | 3.69 | 5 | m | - | M11 | [3.63 .. 3.74] |
| 19 | 92<>, 29<>, 70<>, 50<>, 23<ax>, 79<>, 41<>, 58<> | 3.86 | 8 | m | - | M10 | [3.77 .. 3.95] |
| 20 | 74<ax>, 67<ax>, 50<> | 4.09 | 3 | m | - | M09 | [4.04 .. 4.15] |
| 21 | 52<ax> | 4.45 | 1 | d | 7.82 | M03 | [4.42 .. 4.49] |
| 22 | 19<ax> | 4.77 | 1 | br d | 8.07 | M08 | [4.76 .. 4.77] |
| 23 | 38<ax> | 4.78 | 1 | br d | 8.07 | M07 | [4.78 .. 4.79] |
| 24 | 76<ax> | 4.80 | 1 | br d | 8.07 | M06 | [4.79 .. 4.81] |
| 25 | 26<ax> | 4.83 | 1 | br d | 7.83 | M05 | [4.81 .. 4.85] |
| 26 | 17<ax>, 89<ax> | 4.91 | 2 | m | - | M04 | [4.86 .. 4.95] |
| 27 | 17<ax> | 5.13 | 1 | br s | - | M02 | [5.09 .. 5.17] |
| 28 | 67<ax> | 5.61 | 1 | d | 7.83 | M01 | [5.58 .. 5.63] |

FIG. 5C

| F2 Atom | F2 (ppm) | F1 Atom | F1 (ppm) |
|---|---|---|---|
| 1<"> | 1.87 | 1 | 19.3 |
| 1<'> | 1.45 | | |
| 2<"> | 2.27 | 2 | 37.1 |
| 2<'> | 1.06 | | |
| | | 3 | 44.3 |
| 4 | 1.12 | 4 | 57.1 |
| | | 5 | 39.8 |
| 6<"> | 1.88 | 6 | 40.9 |
| 6<'> | 0.84 | | |
| 7a | 0.98 | 7 | 53.6 |
| | | 8 | 42 |
| 9<"> | 1.56 | 9 | 41.5 |
| 9<'> | 1.44 | | |
| 10<"> | 1.91 | 10 | 22.1 |
| 10<'> | 1.7 | | |
| 11<"> | 2.15 | 11 | 44 |
| 11<'> | 1.6 | | |
| | | 12 | 88.6 |
| 13<"> | 1.98 | 13 | 37.6 |
| 13<'> | 1.52 | | |
| 14<"> | 1.81 | 14 | 20.3 |
| 14<'> | 1.6 | | |
| | | 15 | 153.1 |
| 16<"> | 2.19 | 16 | 47 |
| 16<'> | 2.08 | | |
| 17<a> | 4.91 | 17 | 104.9 |
| 17<b> | 5.14 | | |
| 19<ax> | 4.77 | 19 | 95.7 |
| 21<ax> | 3.54 | 21 | 74.6 |
| 22<ax> | 3.57 | 22 | 68.5 |
| 23<ax> | 3.92 | 23 | 85.4 |
| 24<ax> | 3.68 | 24 | 78.9 |
| 26<ax> | 4.84 | 26 | 102.4 |
| 28<ax> | 3.39 | 28 | 76.6 |
| 29<"> | 3.87 | 29 | 62 |
| 29<'> | 3.6 | | |
| 31<ax> | 3.15 | 31 | 70.9 |
| 33<ax> | 3.44 | 33 | 76.2 |
| 35<ax> | 3.26 | 35 | 74.6 |
| 38<ax> | 4.79 | 38 | 102.4 |
| 40<ax> | 3.44 | 40 | 76.2 |
| 41<"> | 3.89 | 41 | 61.1 |
| 41<'> | 3.7 | | |
| 43<ax> | 3.51 | 43 | 69.9 |
| 45<ax> | 3.51 | 45 | 76.3 |
| 47<ax> | 3.36 | 47 | 73.8 |
| 50<"> | 4.1 | 50 | 68.9 |
| 50<'> | 3.83 | | |
| 52<ax> | 4.46 | 52 | 103.1 |
| 53<ax> | 3.28 | 53 | 73.8 |
| 54<ax> | 3.44 | 54 | 76.2 |
| 55<ax> | 3.39 | 55 | 69.9 |
| 56<ax> | 3.44 | 56 | 76.2 |
| 58<"> | 3.89 | 58 | 61.1 |
| 58<'> | 3.7 | | |
| | | 64 | 178.8 |
| 67<ax> | 5.62 | 67 | 92.9 |
| 69<ax> | 3.51 | 69 | 76.3 |
| 70<"> | 3.89 | 70 | 61.1 |
| 70<'> | 3.7 | | |
| 72<ax> | 3.54 | 72 | 69.5 |
| 74<ax> | 4.13 | 74 | 88.1 |
| 76<ax> | 4.8 | 76 | 102.4 |
| 78<ax> | 3.39 | 78 | 76.6 |
| 79<"> | 3.89 | 79 | 61.1 |
| 79<'> | 3.7 | | |
| 81<ax> | 3.39 | 81 | 69.9 |
| 83<ax> | 3.51 | 83 | 76.3 |
| 85<ax> | 3.37 | 85 | 73.8 |
| 87<ax> | 4.07 | 87 | 76.3 |
| 89<ax> | 4.92 | 89 | 101.9 |
| 91<ax> | 3.39 | 91 | 76.6 |
| 92<"> | 3.92 | 92 | 62 |
| 92<'> | 3.67 | | |
| 94<ax> | 3.26 | 94 | 70.9 |
| 96<ax> | 3.44 | 96 | 76.2 |
| 98<ax> | 3.22 | 98 | 74.2 |
| 100 | 0.87 | 100 | 16.4 |
| 101 | 1.25 | 101 | 28.6 |

ACD numbering

FIG. 5D
Sugar VII
Sugar VI
Sugar V
Sugar IV
Sugar I
Sugar III
Sugar II
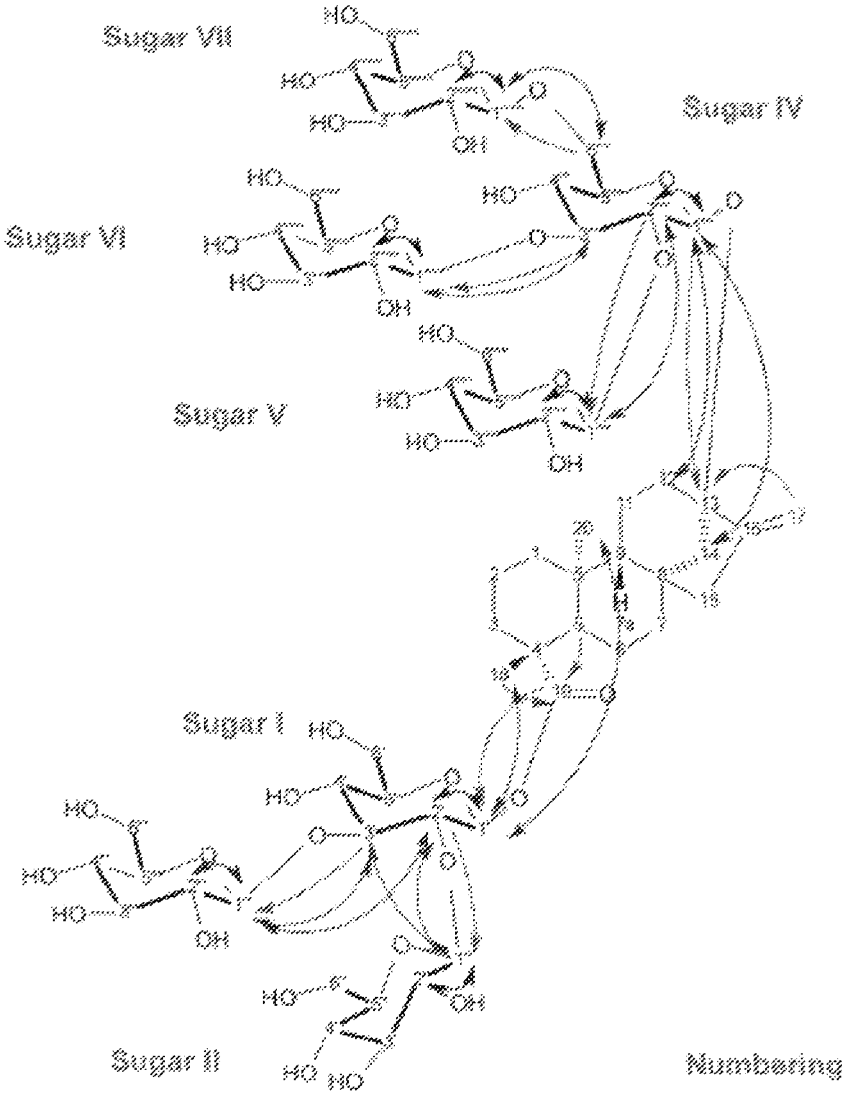
= $^{1}H$-$^{13}C$ HMBC
= $^{1}H$-$^{1}H$ COSY
= $^{1}H$-$^{1}H$ TOCSY spin system
= $^{1}H$-$^{1}H$ dipolar correlation (ROESY)
Assignments were made on the basis of $^{1}H$-$^{1}H$ COSY, $^{1}H$-$^{1}H$ TOCSY, $^{1}H$-$^{13}C$ HSQC-DEPT, $^{1}H$-$^{13}C$ HMBC and $^{1}H$-$^{1}H$ ROESY.
Numbering following IUPAC Cargill OPS1-4

FIG. 6B

| No. | Atom1 | Shift1 (ppm) | H's | Type | J (Hz) | Multiplet1 | (ppm) |
|---|---|---|---|---|---|---|---|
| 1 | 89, 6<> | 0.90 | 4 | m | - | M01 | [0.88 .. 0.93] |
| 2 | 7s | 1.04 | 1 | br d | 8.07 | M02 | [1.02 .. 1.06] |
| 3 | 2<> | 1.11 | 1 | m | - | M03 | [1.08 .. 1.14] |
| 4 | 4 | 1.17 | 1 | br d | 12.47 | M04 | [1.15 .. 1.20] |
| 5 | 90 | 1.28 | 3 | s | - | M05 | [1.26 .. 1.30] |
| 6 | 11<>, 9<>, 1<> | 1.49 | 3 | m | - | M06 | [1.45 .. 1.54] |
| 7 | 14<> | 1.64 | 1 | m | - | M07 | [1.61 .. 1.67] |
| 8 | 10<> | 1.74 | 1 | m | - | M08 | [1.71 .. 1.78] |
| 9 | 6<*>, 10<*>, 1<*> | 1.89 | 3 | m | - | M09 | [1.83 .. 1.94] |
| 10 | 13<*> | 1.98 | 1 | td | 12.10, 6.11 | M10 | [1.95 .. 2.01] |
| 11 | 16<> | 2.10 | 1 | br d | 17.12 | M11 | [2.08 .. 2.13] |
| 12 | 11<*>, 16<*> | 2.20 | 2 | m | - | M12 | [2.18 .. 2.24] |
| 13 | 2<*> | 2.30 | 1 | m | - | M13 | [2.28 .. 2.33] |
| 14 | 57<ax>, 52<ax> | 3.32 | 2 | m | - | M14 | [3.29 .. 3.34] |
| 15 | 41<>, 75<ax> | 3.88 | 3 | m | - | M15 | [3.82 .. 3.96] |
| 16 | 41<*> | 4.22 | 1 | br d | 9.54 | M16 | [4.20 .. 4.24] |
| 17 | 43<ax> | 4.50 | 1 | d | 7.83 | M17 | [4.48 .. 4.53] |
| 18 | 24<ax>, 70<>, 56<ax>, 81<> | 3.73 | 4 | m | - | M18 | [3.68 .. 3.79] |
| 19 | 19<ax> | 4.79 | 1 | d | 7.83 | M19 | [4.78 .. 4.80] |
| 20 | 25<ax> | 4.88 | 1 | d | 8.07 | M20 | [4.86 .. 4.90] |
| 21 | 17<ax> | 4.95 | 1 | s | - | M21 | [4.94 .. 4.97] |
| 22 | 17<eq> | 5.16 | 1 | br s | - | M22 | [5.14 .. 5.18] |
| 23 | 67<ax> | 5.61 | 2 | d | 7.83 | M23 | [5.60 .. 5.62] |
| 24 | 78<ax> | 4.79 | 1 | m | - | M24 | [4.78 .. 4.80] |
| 25 | 29<> | 3.66 | 1 | dd | 12.23, 7.09 | M25 | [3.64 .. 3.68] |
| 26 | 69<ax> | 3.59 | 1 | ddd | 9.72, 5.07, 2.32 | M26 | [3.57 .. 3.61] |
| 27 | 48<ax>, 85<ax> | 3.48 | 8 | m | - | M27 | [3.38 .. 3.57] |
| 28 | 83<ax> | 3.36 | 1 | m | - | M28 | [3.34 .. 3.38] |
| 29 | 38<ax> | 4.77 | 1 | m | - | M29 | [4.75 .. 4.78] |
| 30 | 35<ax> | 3.27 | 1 | m | - | M30 | [3.25 .. 3.29] |
| 31 | 72<ax> | 3.51 | 1 | m | - | M31 | [3.49 .. 3.53] |
| 32 | 22<ax>, 58<ax> | 3.42 | 1 | m | - | M32 | [3.38 .. 3.46] |
| 33 | 33<ax>, 28<ax> | 3.47 | 1 | m | - | M33 | [3.46 .. 3.48] |
| 34 | 80<ax> | 3.55 | 1 | m | - | M34 | [3.53 .. 3.56] |
| 35 | 14<*> | 1.85 | 1 | m | - | M35 | [1.83 .. 1.87] |
| 36 | 64<ax> | 3.53 | 1 | m | - | M36 | [3.51 .. 3.55] |
| 37 | 74<ax> | 3.85 | 1 | m | - | M37 | [3.83 .. 3.87] |
| 38 | 70<*> | 3.91 | 1 | m | - | M38 | [3.87 .. 3.94] |
| 39 | 46<*>, 61<*> | 3.90 | 1 | m | - | M39 | [3.85 .. 3.94] |
| 40 | 23<ax>, 29<*> | 3.90 | 1 | m | - | M40 | [3.85 .. 3.94] |
| 41 | 81<*> | 3.90 | 1 | m | - | M41 | [3.85 .. 3.94] |
| 42 | 31<ax> | 3.24 | 1 | m | - | M42 | [3.23 .. 3.26] |
| 43 | 45<ax> | 3.46 | 1 | m | - | M43 | [3.44 .. 3.48] |
| 44 | 50<ax>, 40<ax> | 3.41 | 1 | m | - | M44 | [3.38 .. 3.43] |
| 45 | 48<*> | 3.74 | 1 | m | - | M47 | [3.71 .. 3.77] |
| 46 | 81<> | 3.76 | 1 | m | - | M49 | [3.74 .. 3.78] |
| 47 | 13<*>, 9<*> | 1.57 | 2 | m | - | M51 | [1.54 .. 1.61] |

Sugar VI
Sugar V
Sugar IV
Sugar III
Sugar I
Sugar II

= $^{1}H$-$^{13}C$ HMBC

= $^{1}H$-$^{1}H$ COSY

= $^{1}H$-$^{1}H$ TOCSY spin system

= $^{1}H$-$^{1}H$ dipolar correlation (ROESY)

Assigments were made on the basis of $^{1}H$-$^{1}H$ COSY, $^{1}H$-$^{1}H$ TOCSY, $^{1}H$-$^{13}C$ HSQC-DEPT, $^{1}H$-$^{13}C$ HMBC and $^{1}H$-$^{1}H$ ROESY.

Numbering following IUPAC

OPS1-5

FIG. 7B

| No. | Atom1 | Shift1 (ppm) | H's | Type | J (Hz) | Multiplet1 | (ppm) |
|---|---|---|---|---|---|---|---|
| 1 | 6<'>, 100 | 0.90 | 6 | s | - | M01 | [0.86 .. 0.94] |
| 2 | 101 | 1.28 | 6 | s | - | M02 | [1.26 .. 1.31] |
| 3 | 9<'>, 1<'>, 11<'> | 1.50 | 8 | m | - | M03 | [1.46 .. 1.53] |
| 4 | 9<'>, 13<'> | 1.57 | 3 | m | - | M04 | [1.54 .. 1.60] |
| 5 | 2<'>, 1<'>, 10<'> | 1.92 | 4 | m | - | M05 | [1.87 .. 1.96] |
| 6 | 35<ax>, 98<ax> | 3.27 | 2 | q | 8.31 | M06 | [3.25 .. 3.30] |
| 7 | 85<ax>, 93<ax>, 78<ax>, 91<ax>, 28<ax>, 58<ax>, 23<ax>, 21<ax>, 46<a | 3.43 | 13 | m | - | M07 | [3.39 .. 3.48] |
| 8 | 45<ax>, 54<ax>, 81<ax>, 55<ax> | 3.54 | 6 | m | - | M08 | [3.53 .. 3.56] |
| 9 | 72<ax>, 85<ax> | 3.62 | 3 | br d | 4.49 | M09 | [3.60 .. 3.64] |
| 10 | 49<'>, 82<'>, 79<'>, 81<'>, 24<ax>, 40<ax>, 70<'> | 3.73 | 11 | m | - | M10 | [3.69 .. 3.78] |
| 11 | 29<'>, 61<'>, 92<'>, 70<'>, 22<ax>, 79<'>, 49<'>, 41<'> | 3.90 | 18 | m | - | M11 | [3.83 .. 3.97] |
| 12 | 67<ax> | 5.63 | 1 | d | 7.34 | M13 | [5.61 .. 5.66] |
| 13 | 17<b> | 5.18 | 1 | br s | - | M14 | [5.13 .. 5.20] |
| 14 | 85<ax>, 17<a> | 4.95 | 3 | m | - | M15 | [4.92 .. 4.98] |
| 15 | 76<ax> | 4.81 | 1 | br s | - | M16 | [4.81 .. 4.88] |
| 16 | 26<ax> | 4.86 | 2 | br d | 7.82 | M17 | [4.85 .. 4.88] |
| 17 | 38<ax> | 4.77 | 2 | br d | 7.83 | M18 | [4.75 .. 4.78] |
| 18 | 43<ax> | 4.50 | 1 | d | 7.83 | M19 | [4.48 .. 4.52] |
| 19 | 19<ax> | 4.79 | 2 | br d | 9.31 | M20 | [4.78 .. 4.80] |
| 20 | 41<'> | 4.23 | 1 | br d | 10.78 | M21 | [4.20 .. 4.28] |
| 21 | 74<ax> | 4.15 | 1 | br d | 3.91 | M22 | [4.13 .. 4.17] |
| 22 | 87<ax> | 4.11 | 1 | m | - | M23 | [4.09 .. 4.13] |
| 23 | 29<'> | 3.66 | 2 | br dd | 12.23, 7.34 | M24 | [3.64 .. 3.68] |
| 24 | 47<ax>, 33<ax>, 96<ax> | 3.50 | 5 | m | - | M25 | [3.48 .. 3.53] |
| 25 | 31<ax> | 3.21 | 1 | t | 9.29 | M26 | [3.19 .. 3.23] |
| 26 | 94<ax>, 44<ax> | 3.33 | 3 | m | - | M27 | [3.30 .. 3.35] |
| 27 | 8<'> | 2.28 | 1 | br d | 12.72 | M28 | [2.26 .. 2.30] |
| 28 | 11<'>, 16<'> | 2.20 | 3 | m | - | M29 | [2.17 .. 2.23] |
| 29 | 16<'> | 2.11 | 2 | br d | 16.14 | M30 | [2.07 .. 2.14] |
| 30 | 13<'> | 2.00 | 2 | br d | 6.95 | M31 | [1.97 .. 2.04] |
| 31 | 14<'> | 1.84 | 2 | br d | 5.29 | M32 | [1.81 .. 1.86] |
| 32 | 10<'> | 1.72 | 3 | m | - | M33 | [1.67 .. 1.77] |
| 33 | 14<'> | 1.63 | 2 | m | - | M34 | [1.60 .. 1.67] |
| 34 | 4 | 1.17 | 2 | br d | 12.23 | M35 | [1.15 .. 1.20] |
| 35 | 2<'> | 1.11 | 2 | m | - | M36 | [1.08 .. 1.14] |
| 36 | 7a | 1.04 | 2 | br d | 7.83 | M37 | [1.01 .. 1.06] |

FIG. 7C

| F2 Atom | F2 (ppm) | F1 Atom | F1 (ppm) |
|---|---|---|---|
| 1<"> | 1.9 | 1 | 21.7 |
| 1<'> | 1.48 | | |
| 2<"> | 2.28 | 2 | 33.7 |
| 2<'> | 1.11 | | |
| | | 3 | 46.8 |
| 4 | 1.17 | 4 | 99.5 |
| | | 5 | 41.9 |
| 6<"> | 1.91 | 6 | 43.7 |
| 6<'> | 0.89 | | |
| 7a | 1.04 | 7 | 55.9 |
| | | 8 | 44.1 |
| 9<"> | 1.37 | 9 | 43.9 |
| 9<'> | 1.48 | | |
| 10<"> | 1.94 | 10 | 34.5 |
| 10<'> | 1.72 | | |
| 11<"> | 2.2 | 11 | 46.7 |
| 11<'> | 1.81 | | |
| | | 12 | 92.7 |
| 13<"> | 2 | 13 | 33.9 |
| 13<'> | 1.58 | | |
| 14<"> | 1.84 | 14 | 22.7 |
| 14<'> | 1.63 | | |
| | | 15 | 155.7 |
| 16<"> | 2.2 | 16 | 49.4 |
| 16<'> | 2.11 | | |
| 17<a> | 4.95 | 17 | 107.1 |
| 17<b> | 5.16 | | |
| 19<ax> | 4.79 | 19 | 98.3 |
| 21<ax> | 3.72 | 21 | 77.6 |
| 22<ax> | 3.58 | 22 | 71.5 |
| 23<ax> | 3.83 | 23 | 83.1 |
| 24<ax> | 3.71 | 24 | 81.4 |
| 26<ax> | 4.87 | 26 | 105 |
| 28<ax> | 3.47 | 28 | 78.8 |
| 29<"> | 3.9 | 29 | 64.5 |
| 29<'> | 3.65 | | |
| 31<ax> | 3.21 | 31 | 73.4 |
| 33<ax> | 3.99 | 33 | 78 |
| 35<ax> | 3.27 | 35 | 77 |
| 38<ax> | 4.77 | 38 | 106.2 |
| 40<ax> | 3.47 | 40 | 78.8 |
| 41<"> | 4.23 | 41 | 71.6 |
| 41<'> | 3.87 | | |
| 43<ax> | 4.3 | 43 | 105.4 |
| 44<ax> | 3.33 | 44 | 76 |
| 45<ax> | 3.55 | 45 | 78.8 |
| 46<ax> | 3.41 | 46 | 72.5 |
| 47<ax> | 3.5 | 47 | 78.6 |
| 49<"> | 3.92 | 49 | 63.6 |
| 49<'> | 3.55 | | |
| 54<ax> | 3.53 | 54 | 72.4 |
| 56<ax> | 3.5 | 56 | 78.6 |
| 58<ax> | 3.42 | 58 | 79.1 |
| 61<'> | 3.73 | 61 | 63.7 |
| 61<"> | 3.85 | | |
| | | 64 | 181.2 |
| 67<ax> | 5.63 | 67 | 95.6 |
| 69<ax> | 3.52 | 69 | 79.1 |
| 70<"> | 3.74 | 70 | 63.6 |
| 70<'> | 3.73 | | |

STEVIOL GLYCOSIDE COMPOUNDS, COMPOSITIONS FOR ORAL INGESTION OR USE, AND METHOD FOR ENHANCING STEVIOL GLYCOSIDE SOLUBILITY

CROSS REFERENCE TO RELATED APPLICATION

This application is a continuation of U.S. patent application Ser. No. 17/120,739, filed on Dec. 14, 2020 and issued as U.S. Pat. No. 11,407,780 on Aug. 9, 2022, which is a continuation of U.S. patent application Ser. No. 16/553,200, filed Aug. 28, 2019 and issued as U.S. Pat. No. 10,906,927 on Feb. 2, 2021, which is a continuation of the U.S. patent application Ser. No. 15/536,385, filed Jun. 15, 2017 and issued as the U.S. Pat. No. 10,711,024 on Jul. 14, 2020, which is a U.S. National Stage Application of International Application No. PCT/US2015/066419, filed on Dec. 17, 2015, which claims the benefit of U.S. Provisional Application No. 62/093,213, filed on Dec. 17, 2014, the disclosures of each of which are explicitly incorporated by reference herein in their entirety.

FIELD

The present invention relates to novel steviol glycosides, compositions including these steviol glycosides, and methods for improving solubility of known steviol glycosides compounds using these isomers. The present invention also relates to sweetener compositions and sweetened compositions including one or a combination of these isomers, and uses of such sweetener compositions to prepare sweetened compositions including food, beverages, dental products, pharmaceuticals, nutraceuticals, and the like.

BACKGROUND

Sugars, such as sucrose, fructose and glucose, are utilized to provide a pleasant taste to beverages, foods, pharmaceuticals, and oral hygienic/cosmetic products. Sucrose, in particular, imparts a taste preferred by consumers. Although sucrose provides superior sweetness characteristics, it is caloric. Non-caloric or lower caloric sweeteners have been introduced to satisfy consumer demand, and there is desire for these types of sweeteners that have favorable taste characteristics.

*Stevia* is a genus of about 240 species of herbs and shrubs in the sunflower family (Asteraceae), native to subtropical and tropical regions from western North America to South America. The species *Stevia rebaudiana*, commonly known as sweetleaf, sweet leaf, sugarleaf, or simply *stevia*, is widely grown for its sweet leaves. *Stevia*-based sweeteners may be obtained by extracting one or more sweet compounds from the leaves. Many of these compounds are steviol glycosides, which are glycosides of steviol, a diterpene compound. These diterpene glycosides are about 150 to 450 times sweeter than sugar.

Examples of steviol glycosides are described in WO 2013/096420 (see, e.g., listing in FIG. 1); and in Ohta et. al., "Characterization of Novel Steviol Glycosides from Leaves of *Stevia rebaudiana* Morita," J. Appl. Glycosi., 57, 199-209 (2010) (See, e.g., Table 4 at p. 204). Structurally, the diterpene glycosides are characterized by a single base, steviol, and differ by the presence of carbohydrate residues at positions C13 and C19, as presented in FIGS. 2*a*-2*k*. See also PCT Patent Publication WO 20013/096420.

Typically, on a dry weight basis, the four major steviol glycosides found in the leaves of *Stevia* are dulcoside A (0.3%), rebaudioside C (0.6-1.0%), rebaudioside A (3.8%) and stevioside (9.1%). Other glycosides identified in *Stevia* extract include one or more of rebaudioside B, D, E, F, G, H, I, J, K, L, M, N, O, steviolbioside and rubusoside.

While the major steviol glycoside Reb A is commonly used as sweetener in beverage applications it has off-taste issues. More recently, there has been focus on certain minor steviol glycosides which have better taste properties. For example, rebaudioside M has higher sweetness intensity and is more potent than other steviol glycosides (e.g., see Prakash, I., et al. (2013) *Nat. Prod. Commun.,* 8: 1523-1526, and WO 2013/096420). Rebaudioside D tastes about 200-220 times sweeter than sucrose and in a sensory evaluation it had a slow onset of sweetness and was very clean (e.g., see Prakash, I., et al. (2012) *Int. J. Mol. Sci.,* 13:15126-15136).

Some minor rebaudiosides can be challenging to use because they have less than desirable water solubility properties. For example, it has been reported that Reb D is difficult to use in food products because of its low solubility in water at room temperature. For instance, Reb D needs to be heated to near boiling water temperature for 2 hours in order to achieve complete dissolution at 0.8% concentration. At most only 300 to 450 ppm can be solubilized in water at 23° C. (e.g., see US 2013/0251881). As another example, rebaudioside M obtained from *Stevia rebaudiana* has poor aqueous solubility and dissolution qualities in beverage formulations (e.g., see US 2014/0171519).

Certain methods to improve rebaudioside solubility are less than desirable because they are labor intensive, requiring high processing temperatures and the use excipient compounds. For example, see WO 2013148177.

SUMMARY

The present invention generally relates to novel steviol glycosides, and also relates to using these isomers for improving the solubility of other steviol glycosides compounds in a composition. The invention also relates to uses of the novel steviol glycosides, such as along with other minor and/or major steviol glycosides compounds, as sweetener compositions. The sweetener compositions can be used to prepare sweetened compositions including food, beverages, dental products, pharmaceuticals, nutraceuticals, and the like.

In one embodiment, the invention provides steviol glycosides (compounds 1, 2, 3, and 4) having to the following structures:

(compound 1)

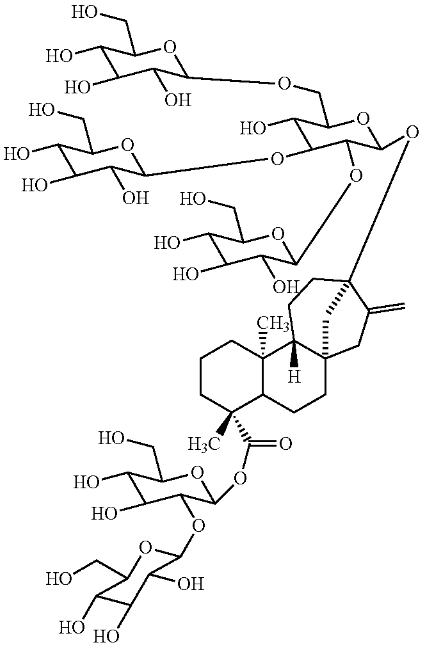

(compound 2)

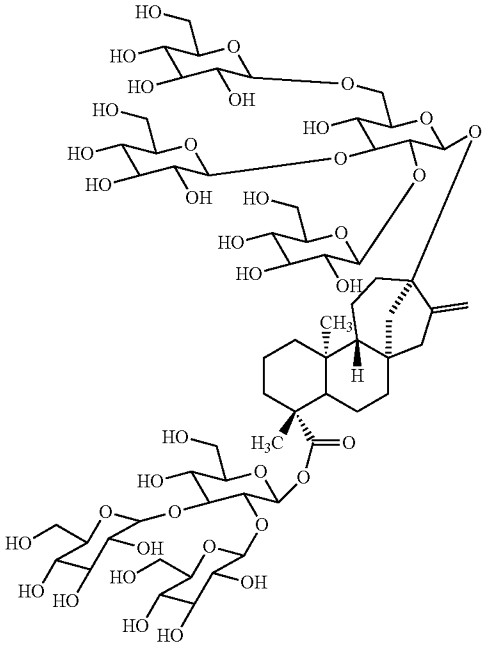

-continued (compound 3)

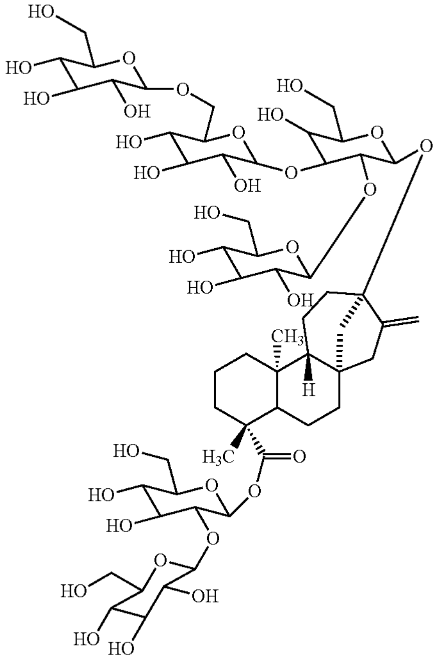

(compound 4)

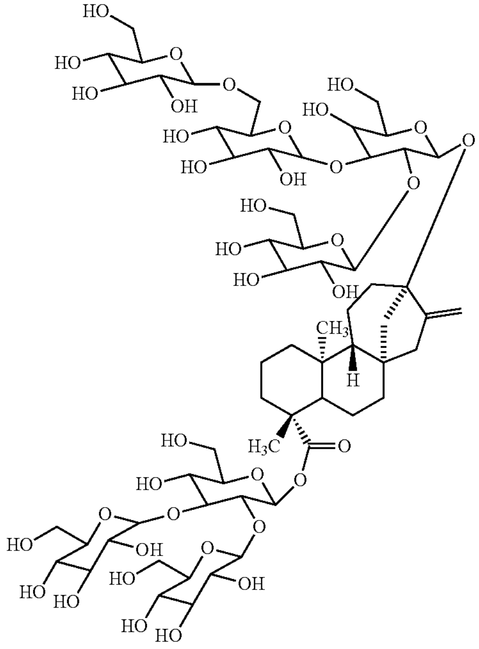

Compounds 1, 2, 3, and 4 can be, individually, in purified form. Compounds 1, 2, 3, and 4 can also be in mixture with each other. This mixture can be purified from other components (i.e., other components that are different than compounds), or the mixture can include one or more other component(s), such as other steviol glycosides (e.g., rebaudioside M and/or rebaudioside D), that are different from compounds 1, 2, 3, and 4.

Accordingly, other embodiments of the invention are directed to fermentation media comprising one or more of compound(s) 1, 2, 3, and 4, optionally with one or more other component(s), such as other steviol glycosides, such as rebaudioside M and/or rebaudioside D. A recombinant host cell can be used to metabolically produce compound(s) 1, 2, 3, and 4. The fermentation media can be enriched steviol glycosides or refined to select for certain steviol glycosides.

Other embodiments of the invention are directed of providing or enhancing sweetness to a composition suitable for oral ingestion or oral use comprising adding one or more of the compounds 1, 2, 3, or 4, such as along with one or more other steviol glycosides (e.g., rebaudioside M and/or rebaudioside D), to a material or composition suitable for oral ingestion or use. Accordingly the invention also provides a composition suitable for oral ingestion or oral use comprising one or more of the compounds 1, 2, 3, or 4, such as beverages, beverage concentrates, frozen beverage, powders, foodstuffs, confections, condiments, chewing gum, dairy products, sweeteners, pharmaceutical compositions, and dental compositions.

In another embodiment, the invention provides a method for enhancing the solubility of a steviol glycoside in an aqueous composition. The method comprises a step of providing an aqueous composition comprising first and second steviol glycosides. The first steviol glycoside has a branched chain of four glucose units attached to an atom of a cyclooctane group of a steviol moiety of the first steviol glycoside. The second steviol glycoside is different than the first steviol glycoside and has a solubility in an aqueous composition (that lacks the first steviol glycoside) that is lower than its solubility in an aqueous composition that includes the first steviol glycoside. Compounds 1, 2, 3, and 4 exemplify the first steviol glycoside.

As an example, the solubility of the (second) steviol glycoside can be enhanced by producing the first and second glycosides together, such as by a recombinant organism under fermentation conditions. As another example, the solubility of the (second) steviol glycoside can be enhanced by adding the first steviol glycoside to a composition that has the second steviol glycoside.

In another embodiment, the invention provides another method for enhancing the solubility of a steviol glycoside in an aqueous composition. The method includes a step of providing an aqueous composition comprising first and second steviol glycosides, wherein the second steviol glycoside is selected from the group consisting of rebaudioside A, rebaudioside B, rebaudioside M, rebaudioside D, rebaudioside I, rebaudioside Q, rebaudioside N, and stevioside. The first steviol glycoside is different from the second steviol glycoside, and has a higher or equal molecular weight than the rebaudioside M, and the second steviol glycoside has a solubility in an aqueous composition that lacks the first steviol glycoside that is lower than a solubility of the second steviol glycoside in an aqueous composition that includes the first steviol glycoside.

DESCRIPTION OF THE FIGURES

FIG. 1 shows structures of known steviol glycosides.

FIGS. 5A-5D constitute a graph showing the position and number of chemical shifts from NMR spectroscopy for compound 2 (OPS 1-2), $^{1}$H NMR (FIG. 5B: $^{1}$H NMR (800 MHz, DEUTERIUM OXIDE) δ ppm 0.87 (s, 4H) 0.96-1.02 (m, 1H) 1.02-1.09 (m, 1H) 1.09-1.15 (m, 1H) 1.24 (s, 3H) 1.44 (br s, 2H) 1.47-1.65 (m, 4H) 1.65-1.75 (m, 1H) 1.88 (br d, J=10.51 Hz, 5H) 2.00-2.09 (m, 1H) 2.10-2.22 (m, 2H) 2.23-2.30 (m, 1H) 3.14 (br t, J=9.41 Hz, 1H) 3.19-3.30 (m, 4H) 3.32-3.47 (m, 12H) 3.47-3.54 (m, 5H) 3.54-3.63 (m, 4H) 3.63-3.74 (m, 5H) 3.77-3.95 (m, 8H) 4.04-4.16 (m, 3H) 4.45 (d, J=7.82 Hz, 1H) 4.77 (br d, J=8.07 Hz, 1H) 4.78 (br d, J=8.01 Hz, 1H) 4.80 (br d, J=8.01 Hz, 1H) 4.83 (br d J=7.83 Hz, 1H) 4.88-4.95 (m, 2H) 5.13 (br s, 1H) 5.61 d, J=7.83 Hz, 1H) and $^{13}$C NMR (FIG. 5C: $^{13}$C NMR (201 MHz, DEUTERIUM OXIDE) ppm 16.4, 19.3, 20.3, 22.1, 28.6, 37.1, 37.5, 398, 40.3, 41.5, 42.0, 44.0, 44.3, 47.0, 53.5, 57.1, 61.1, 61.1, 61.1, 61.1, 62.0, 62.0, 68.5, 68.5, 68.9, 69.9, 69.9, 69.9, 70.9, 70.9, 73.5, 73.8, 74.2, 74.6, 74.8, 76.2, 76.2, 76.2, 76.2, 76.3, 76.3, 76.3, 76.3, 76.6, 76.6, 76.6, 78.9, 85.1, 85.4, 88.6, 92.9, 95.7, 101.9, 102.4, 102.4, 102.4, 103.1, 104.9, 153.1, 178.8) spectroscopy data and atom numbering for compound 2, and chemical assignments for compound 2 made based on COSY, TOCSY, HSQC-DEPT, and HMBC correlations. The chemical structure shown in FIG. 5B is the same as that shown in FIG. 5C, where it is more legible.

FIGS. 6A-6D constitute a graph showing the position and number of chemical shifts from NMR spectroscopy for compound 3 (OPS 1-4), $^{1}$H NMR (FIG. 6B: $^{1}$H NMR (800 MHz, DEUTERIUM OXIDE) δ ppm 0.85-0.93 (m, 4H) 1.04 (br d, J=8.07 Hz, 1H) 1.08-1.14 (m, 1H) 1.17 (br d, J=12.47 Hz, 1H) 1.28 (s, 3H) 1.45-1.54 (m, 3H) 1.54-1.61 (m, 2H) 1.61-1.67 (m, 1H) 1.71-1.78 (m, 1H) 1.83-1.87 (m, 1H) 1.83-1.94 (m, 3H) 1.98 (td, J=12.10, 6.11 Hz, 1H) 2.10 (br d, J=17.12 Hz, 1H) 2.18-2.24 (m, 2H) 2.28-2.33 (m, 1H) 3.23-3.26 (M, 1H) 3.26-3.29 (m, 1H) 3.29-3.34 (m, 2H), 3.34-3.38 (m, 1H) 3.38-3.57 (m, 5H) 3.38-3.46 (m, 1H) 3.53-3.56 (m, 1H) 3.59 (ddd, J=9.72, 5.07, 2.32 Hz, 1H) 3.66 (dd, J=12.23, 7.09 Hz, 1H) 3.68-3.79 (m, 4H) 3.71-3.77 (m, 1H) 3.74-3.78 (m, 1H), 3.87-3.94 (m, 1H) 4.22 (br d, J=9.54 Hz, 1H) 4.50 (d, J=7.83 Hz, 1H) 4.75-4.78 (m, 1H) 4.79 (d, J=7.83 Hz, 1H) 4.78-4.80 (m, 1H) 4.88 (d, J=8.07 Hz, 1H) 4.95 (s, 1H) 5.16 (br s, 1H) 5.61 (d, J=7.82 Hz, 2H) and $^{13}$C NMR (FIG. 6C: $^{13}$C NMR (201 MHz, DEUTERIUM OXIDE) δ ppm 18.8, 21.8, 22.6, 24.2, 31.1, 39.6, 39.6, 42.0, 42.7, 43.7, 44.1, 46.8, 46.8, 49.5, 55.8, 59.5, 63.3, 63.5, 63.7, 64.3, 64.3, 71.3, 71.5, 72.2, 72.3, 72.5, 72.8, 73.3, 75.9, 76.1, 77.0, 77.5, 78.0, 78.4, 78.4, 78.5, 78.6, 78.7, 78.7, 78.8, 79.0, 79.3, 80.8, 81.3, 89.0, 90.5, 95.4, 98.4, 104.8, 105.2, 105.3, 105.3, 107.1, 155.9, 181.1) spectroscopy data and atom numbering for compound 3, and chemical assignments for compound 3 made based on COSY, TOCSY, HSQC-DEPT, and HMBC correlations. The chemical structure shown in FIG. 6A is the same as that shown in FIG. 6C, where it is more legible.

DETAILED DESCRIPTION

Figure 2:
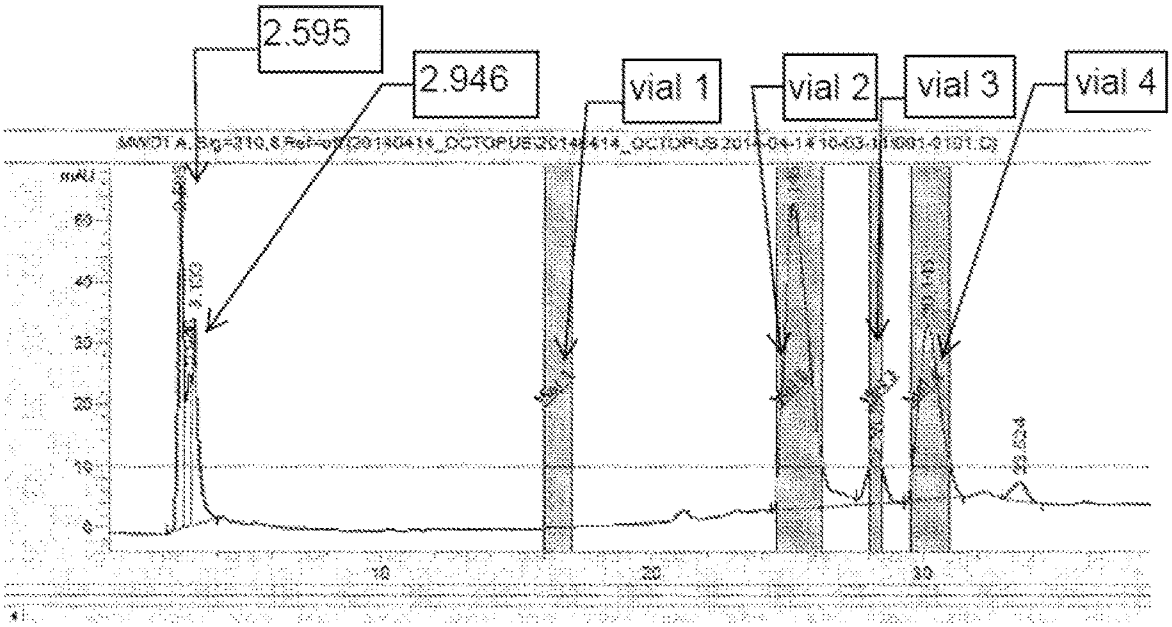
FIG. 2 is a purification chromatogram of compound 1 (OPS 1-1) and compound 2 (OPS 1-2). OPS 1-1 and OPS 1-2 purification chromatogram. Vial 2 is OPS 1-1 and vial 4 is OPS 1-2. Purified fractions of each compound from multiple injections were pooled together and dried under nitrogen at room temperature, producing the solid material that was characterized by NMR.

Embodiments of the disclosure described herein are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

For example, some embodiments of the disclosure are directed to the following compounds:

(compound 1)

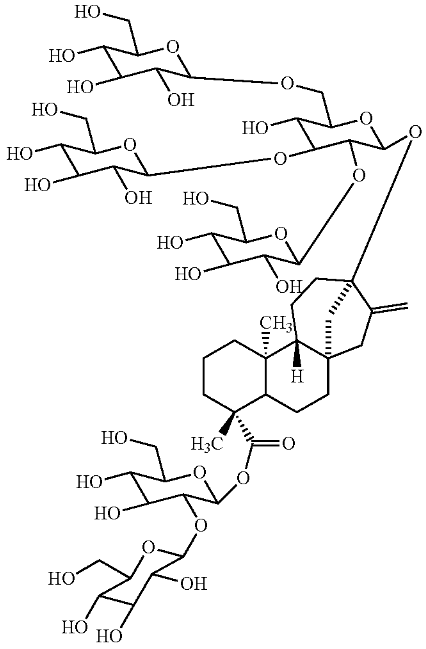

(compound 2)

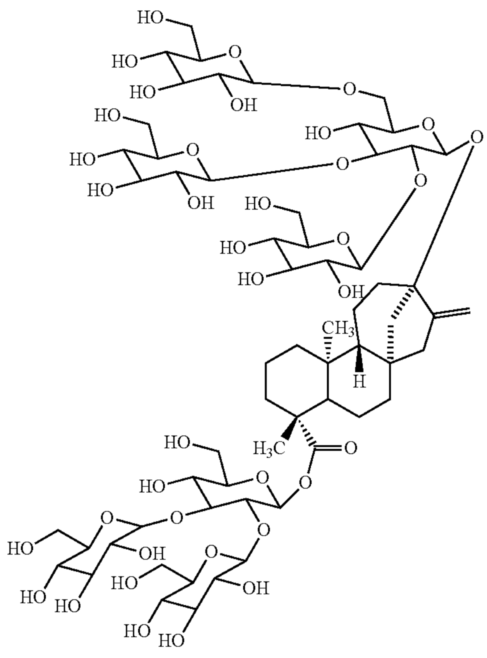

-continued (compound 3)

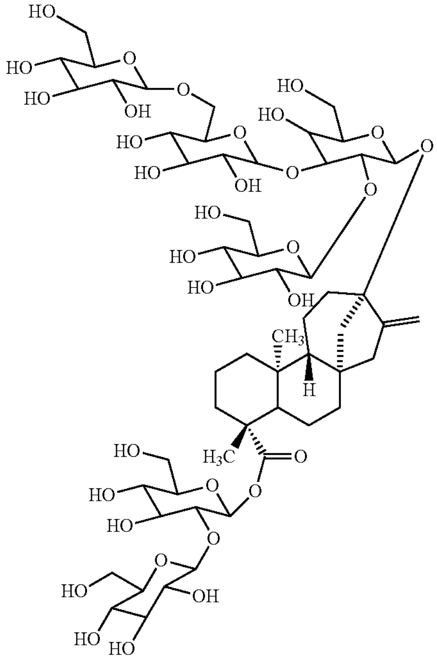

(compound 4)

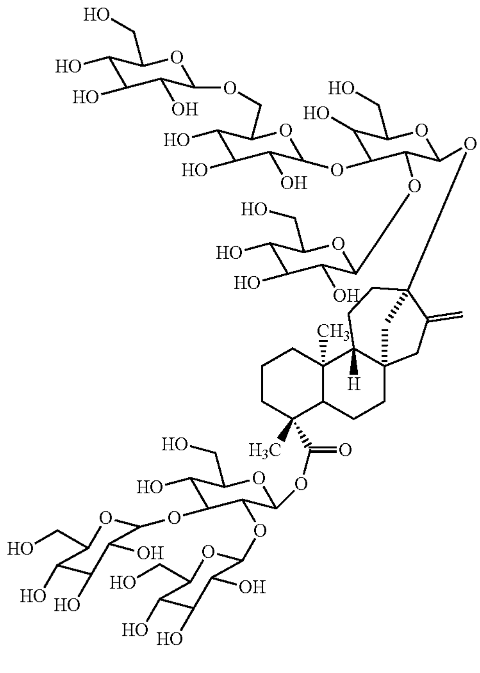

Compounds 1, 2, 3, and 4 are not known to be produced in the *Stevia* plant. Rather, it has been found that these compounds 1, 2, 3, and 4 can be produced by microorganisms engineered for the synthesis of other steviol glycosides.

Structurally, compounds 1-4 have a central molecular moiety, which is a single steviol base, and glucopyranosyl residues attached to the C13 and C19 atoms of the steviol base, according to the atom numbering on the base shown below. That is, glucopyranosyl residues represent groups $R_2$ and $R_1$ in the following formula:

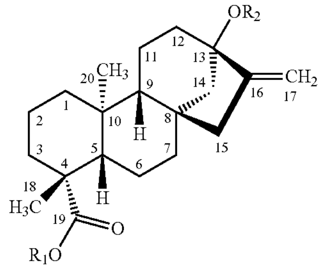

Compounds 1-4 can be characterized by having a first group of four glucopyranose residues attached via the number 13 carbon (C13) of the steviol moiety. That is, $R_2$ is a group (first group) having four glucopyranosyl residues. The first group of four glucopyranose residues can have a branched (non-linear) structure, meaning that at least two glucopyranose residues are connected to a single glucopyranose residue. Compounds 1-4 can also be characterized by having a second group of two or three glucopyranose residues attached via the number 19 carbon (C19) of the steviol moiety. That is, $R_1$ is a group having two or three glucopyranosyl residues. The second group of two or three glucopyranose residues can have a linear or branched structure. In this regard, the compounds can be characterized as having a total of six glucopyranose residue (as in compounds 1 and 2), or a total of seven glucopyranose residues (as in compounds 3 and 4).

The molecular weight of the fully protonated forms of compounds 1 and 2 ($C_{56}H_{90}O_{33}$) is 1291.29, and the molecular weight of the fully protonated forms of compounds 3 and 4 ($C_{62}H_{100}O_{38}$) is 1453.43.

Glucopyranose units of the first and second groups can be described in relation to their positions relative to the steviol moiety, using terms such as primary, secondary, tertiary, etc. For example, in the first group ($R_2$), an ether linkage can attach the 1C of the primary glucopyranose residue to the C13 of the steviol moiety. A secondary glucopyranose residue can be attached to the primary glucopyranose. That is, one glucopyranose residue can be present between the secondary glucopyranose residue and the C13 of the steviol moiety. Compounds 2 and 4 exemplify compounds having two secondary glucopyranose residues attached to the primary glucopyranose residue. Compounds 1 and 3 exemplify compounds having three secondary glucopyranose residues attached to the primary glucopyranose residues. A tertiary glucopyranose residue can be attached to a secondary glucopyranose. That is, two glucopyranose residues can be present between a tertiary glucopyranose residue and the C13 of the steviol moiety. Compounds 2 and 4 exemplify compounds having one tertiary glucopyranose residue attached to a secondary glucopyranose residue.

Glucopyranose units of the first group ($R_2$) can also be described by their chemical linkages to each other. Chemical linkages in the first group can include 1→2 glycosidic, 1→3 glycosidic linkage, and 1→6 glycosidic linkages. Compounds 1 and 3 exemplify compounds having 1→2 glycosidic, 1→3 glycosidic linkage, and 1→6 glycosidic linkages between the secondary glucopyranose residues and the primary glucopyranose residue. Compounds 2 and 4 exemplify compounds having 1→2 glycosidic, and 1→3 glycosidic linkage, between the secondary glucopyranose residues and the primary glucopyranose residue, and a 1→6 glycosidic linkage between the tertiary glucopyranose residue and a secondary glucopyranose residue.

In the second group ($R_1$), an ether linkage can attach the 1C of the primary glucopyranose residue to the C19 of the steviol moiety. One or more secondary glucopyranose(s) residue can be attached to the primary glucopyranose in the second group. Compounds 1 and 2 exemplify compounds having one secondary glucopyranose residue attached to the primary glucopyranose residue. Compounds 3 and 4 exemplify compounds having two secondary glucopyranose residues attached to the primary glucopyranose residues.

Glucopyranose units of the second group ($R_1$) can also be described by their chemical linkages to each other. Chemical linkages in the second group can include 1→2 glycosidic and 1→3 glycosidic linkage linkages. Compounds 1 and 2 exemplify compounds having 1→2 glycosidic linkages, and compounds 3 and 4 exemplify compounds having 1→2 glycosidic and 1→3 glycosidic linkages, between the secondary glucopyranose residue(s) and the primary glucopyranose residue.

In some modes of practice, compounds 1-4 can be produced in a fermentation process. For example, the fermentation process can use a genetically modified organism that is engineered for the production of one or more steviol glycosides, such as RebM and RebD. In particular, compounds 1-4 can be carried out using an engineered microbial strain having a set of enzymes that provide a pathway for the synthesis of one or more of compounds 1-4. One or more other steviol glycosides that are different than compounds 1-4 can also be produced by the engineered microbial strains or enzymatic preparations from the engineered microbial strains.

An engineered microbe useful for the production of compounds 1-4 expresses the following enzymes: geranylgeranyl diphosphate synthase (GGPPS), ent-copalyl diphosphate synthase (CDPS), kaurene oxidase (KO), kaurene synthase (KS); steviol synthase (KAH), cytochrome P450 reductase (CPR), UGT74G1, UGT76G1, UGT91 d2, and a EUGT11. WO 2014/122227 describes an engineered yeast strain that express these enzymes. The UGT74G1 enzyme functions as a uridine 5'-diphospho glucosyl: steviol 19-COOH transferase and a uridine 5'-diphospho glucosyl: steviol-13-O-glucoside 19-COOH transferase. The UGT76G1 enzyme is a *stevia* uridine diphosphate dependent glycosyltransferase that catalyzes several glycosylation reactions on the steviol backbone. The UGT76G1 enzyme can catalyze glycosylation of steviol and steviol glycosides at the 19-0 position or the 13-0 position. The UGT91 D2 and EUGT11 enzymes can function as a uridine 5'-diphospho glucosyl: steviol-13-O-glucoside transferases (also referred to as a steviol-13-monoglucoside 1,2-glucosylase), transferring a glucose moiety to the C-2' of the 13-O-glucose of the acceptor molecule, steviol-13-O-glucoside, or as uridine 5'-diphospho glucosyl: rubusoside transferases transferring a glucose moiety to the C-2' of the 13-O-glucose of the acceptor molecule, rubusoside, to produce stevioside. The EUGT11 enzyme also can transfer a glucose moiety to the C-2' of the 19-O-glucose of the acceptor molecule, rubusoside, to produce a 19-0-1,2-diglycosylated rubusoside.

Fermentation can be carried out under conditions and in medium suitable for production of compounds 1-4. Other steviol glycosides can be produced by the engineered microbe, such as rebaudioside M, rebaudioside D, rebaudioside A, and rebaudioside B. Compounds 1-4 can be produced in amounts less than the amounts of steviol glycosides such as rebaudioside M and rebaudioside D. Fermentation conditions generally use oxygen (aerobic conditions), a lower pH, a carbon source, and a nutrient (nitrogen) base. Fermentation can be carried out using a fed batch or continuous process.

Fermentation can be carried out using a first growth phase in base medium, followed by a longer feeding phase using a glucose-containing defined feed medium (with trace metals, vitamins, and salts). The fermentation minimal medium includes glucose (5 g/L), ammonium sulfate (5 g/L), potassium dihydrogenphosphate (3 g/L), magnesium sulphate (0.5 g/L), trace elements, and vitamins (e.g., see, Verduyn, C. et al. (1992) Yeast 8, 501-517). The pH of the fermentation media can kept at about pH 5 and the temperature at about 30° C.

Optionally, fermentation can be carried out in media containing steviol-13-O-glucoside or steviol-19-O-glucoside. Using this media, the microorganism contains and expresses genes encoding a functional EUGT1 1, a functional UGT74G1, a functional UGT85C2, a functional UGT76G1, and a functional UGT91 D2. Compounds 1-4, rebaudioside A, rebaudioside D, and rebaudioside M may be obtained from the fermentation media.

As another option, fermentation can be carried out in media containing rubusoside. Using this media, the microorganism contains and expresses genes encoding a functional EUGT1 1, a functional UGT76G1, and a functional UGT91 D2. Compounds 1-4, rebaudioside A, D, and M may be obtained from the fermentation media.

As another option, preparation of compounds 1-4 can be carried out using an enzyme preparation from one or more genetically engineered organism(s), such as an organism described herein. For example, in one mode of practice, a genetically engineered microbe expressing geranylgeranyl diphosphate synthase (GGPPS), ent-copalyl diphosphate synthase (CDPS), kaurene oxidase (KO), kaurene synthase (KS); steviol synthase (KAH), cytochrome P450 reductase (CPR), UGT74G1, UGT76G1, UGT91 d2, and EUGT11 enzymes is used to make an enzyme composition. For example, the organism can be treated with reagents that disrupt cell membranes to release the enzymes into a composition, or if enzymes are secreted into a growth media for the organism, the media can be used to prepare the composition. The enzyme-containing composition is then contacted with one or more precursor compounds (e.g., a steviol glycoside precursor) which is subjected to at least one enzymatic reaction, or typically multiple enzymatic reactions through a series of intermediates, to provide a composition that includes compounds 1-4.

Alternatively, an enzyme composition is prepared by combining cellular extracts from multiple engineered organisms, each organism expressing less than a desired number of enzymes (e.g., one or two) for the enzymatic conversion of a steviol glycoside precursor to compounds 1-4. Extracts from the multiple organisms can be combined for preparation of the enzymatic composition.

Following a period of fermentation a composition containing steviol glycosides including one or more of compounds 1-4 can be obtained from the culture media using various techniques. In some embodiments, a compound such as permeabilizing agent can be added to the fermentation media to enhance removal of the steviol glycosides from the cell and into the media.

The fermentation media can then be centrifuged or filtered to remove the engineered cells. The fermentation media can optionally be treated to remove low molecular weight components (glucose, basic nutrients, and salts), such as by membrane dialysis. Depending on a desired use, a composition comprising compounds 1-4, optionally with other steviol glycosides, can be used.

If it is desired to provide a composition with steviol glycosides including compounds 1-4 in enriched or purified form, or where compounds 1-4 are separated from other steviol glycosides, or separated from one another, further purification can be carried out. Such enrichment or purification of steviol glycoside components can be carried out on liquid fermentation media, or the fermentation media can then be dried down prior to purification. For example, fermentation media can be dried down using lyophilization to form a dry composition (e.g., powder or flakes) including steviol glycosides with compounds 1-4 that can be subsequently processed.

In some modes of practice, dried fermentation broth enriched for steviol glyosides including compounds 1-4, is used as the starting material for purification. For example, a solvent or solvent combination can be added to the dried fermentation broth to dissolve or suspend material that includes the steviol glycosides. An exemplary combination for dissolving the steviol glycosides is a mixture of water and an alcohol (e.g., 50:50 ethanol:water). To facilitate dissolving or suspending, the dried broth materials can be heated at a temperature above room temperature, such as in the range of 40° C.-60° C. Mechanical disruption of the dried broth materials can also be performed, such as by sonication. The dissolved or suspended broth materials can be filtered using a micron or sub-micron prior to further purification, such as by preparative chromatography.

Dried fermentation broth enriched for steviol glycoside compounds can be subjected to purification, such as by reverse phase liquid chromatography. A suitable resin can be used to retain steviol glycoside compounds in the column, with removal of hydrophilic compounds which get washed through the column with a liquid such as water. Elution of steviol glycosides including compounds 1-4 from the column can be accomplished a suitable solvent or solvent combination such as acetonitrile or methanol.

Elution of steviol glycosides including compounds 1-4 from a reverse phase column can yield a composition which can be useful for any one of a variety of purposes. For example, the a purified composition with compounds 1-4 can be sued as a sweetener composition for oral ingestion or oral use. The composition can be defined with regards to the steviol glycosides in the composition.

For example, compounds 1, 2, 3, and 4 can be defined with regards to the "total steviol glycosides" present in the composition. The "total steviol glycosides" refers all the steviol glycosides present in the composition, including steviol glycosides compounds 1, 2, 3, and 4, and steviol glycosides that are different than compounds 1, 2, 3, and 4. Total steviol glycosides can be defined in terms of steviol glycoside type and amount.

Exemplary steviol glycosides that are different than compounds 1, 2, 3, and 4 include, but are not limited to, rebaudioside M, rebaudioside D, rebaudioside A, rebaudioside B, rebaudioside N, and stevioside. These other steviol glycosides may be produced in a fermentation process along with compounds 1-4. The amounts of steviol glycosides in the composition can be expressed in relation to one another, or to the total amount of steviol glycosides, such as by a weight percentage of the total amount of steviol glycosides, or a ratio, or range of ratios, expressed as weight percent, or molar percent.

Total steviol glycosides (TSG) is calculated as the sum of the content of all steviol glycosides in a composition on a dry (anhydrous) basis. Unless expressed herein otherwise, an "amount" of steviol glycoside will refer to the percentage by weight (% wt) of the steviol glycoside, or combination thereof.

In some preparations, any one of compounds 1, 2, 3, or 4 is present in the composition in the range of about 0.05% to about 5% (wt) of the total amount steviol glycosides in the composition. Compound 1 can be the most abundant of compounds 1, 2, 3, and 4, and can be present in the range of about 2% to about 4.5%, about 3% to about 4.25%, or about 3.5% to about 4.0% of the total amount steviol glycosides in the composition. Compound 4 can be the least abundant of compounds 1, 2, 3, and 4, and be present in the range of about 0.05% to about 1%, about 0.1% to about 0.5%, or about 0.15% to about 0.25% of the total amount of steviol glycosides in the composition. Compounds 2 and 3 can present in amounts, individually, between the amounts of compounds 1 and 4, such as in the range of about 0.1% to about 1.5%, about 0.25% to about 0.1%, or about 0.4% to about 0.8% of the total amount steviol glycosides in the composition.

The combined amount of compounds 1, 2, 3, or 4 can also be expressed in relation to the total amount steviol glycosides in the composition. For example the combined amount of compounds 1, 2, 3, and 4, can be present in the range of about 0.5% to about 10%, about 1% to about 8%, about 2% to about 7%, or about 4% to about 6% of the total amount steviol glycosides in the composition.

As discussed herein, the composition can include one or more other steviol glycosides that are different than compounds 1, 2, 3, or 4. These other steviol glycosides can be retained in a composition if they are not purified away from the compounds 1, 2, 3, and 4. For example, other steviol glycosides can be present along with compounds 1, 2, 3, and 4 if the other steviol glycosides are produced in a common fermentation process. Exemplary steviol glycosides include those such as rebaudioside M, rebaudioside D, rebaudioside A, rebaudioside B, rebaudioside N, and stevioside. In some embodiments, the steviol glycosides rebaudioside M and rebaudioside D can be produced by an engineered organism as the predominant steviol glycosides, and therefore can represent the major portion of the steviol glycosides in the composition that includes compounds 1, 2, 3, or 4. Rebaudioside M or rebaudioside D can, in some embodiments, be present in the composition an amount greater than any one of compounds 1, 2, 3, or 4. For example, rebaudioside M or rebaudioside D can be present in an amount in the range of about 10 times to about 500 times, about 25 times to about 250 times, or about 50 times to about 200 times greater than any one of compounds 1, 2, 3, or 4.

A steviol glycoside composition that includes compounds 1, 2, 3, or 4. can optionally be expressed in terms of amounts of rebaudioside M and rebaudioside D. For example, rebaudioside M and rebaudioside D can be present in the composition in a total amount of about 90% (wt) or greater, about 92.5% (wt) or greater, or 95% (wt) or greater, of a total amount steviol glycosides in the composition. Rebaudioside M can be the predominant steviol glycoside in the composition, and can be present, for example, in an amount in the range of about 45% to about 70%, about 50% to about 65%, or about 52.5% to about 62.5% of the total amount steviol glycosides in the composition. Rebaudioside D can be in an amount less than Rebaudioside M, such as in an amount in the range of about 25% to about 50%, about 30% to about 45%, or about 32.5% to about 42.5% of the total amount steviol glycosides in the composition.

The composition can optionally be expressed in terms of amounts of other known steviol glycosides that are present in minor amounts. For example, composition can include one or more of rebaudioside A, rebaudioside B, or stevioside in an amount of about 1% (wt) or less, about 0.5% (wt) or less, or about 0.25% (wt) or less, of a total amount steviol glycosides in the composition.

The composition can optionally be expressed in terms of the concentration of one or more steviol glycoside(s). Beneficially, it has been founds that compound(s) 1, 2, 3, and/or 4, can improve solubility of steviol glycosides in an aqueous solution, and therefore compositions can be prepared having a greater concentration of steviol glycosides in solution. As used herein "instantaneous solubility" refers to the solubility of a steviol glycoside, or mixture of steviol glycosides, that are vigorously mixed with deionized water at room temperature (25° C.). As used herein "equilibrium solubility" refers to the solubility of a steviol glycoside, or mixture of steviol glycosides, that are vigorously mixed with deionized water at 80° C. for 15 minutes, cooled to room temperature (25° C.), and then observed up to 4 days. Clear solutions without precipitates are considered soluble. Unless indicated otherwise herein, the term "solubility" refers to "equilibrium solubility."

In the absence of compound(s) 1, 2, 3, and/or 4, rebaudioside D has a very low instantaneous solubility (less than 0.08% at room temperature) in water. Upon heating to 80° C. for 15 minutes, rebaudioside D has an equilibrium solubility 0.08% for at least 4 days at room temperature. Rebaudioside M has a higher solubility than rebaudioside D. The instantaneous solubility of rebaudioside M is about 0.13%, and its equilibrium solubility is about 0.2% at room temperature.

In experimental studies associated with the disclosure, the addition of compounds 1-4, significantly improves the aqueous solubility of rebaudioside M and rebaudioside D in a composition. For example, a steviol glycoside composition having a mixture of rebaudioside M, rebaudioside D, and 1, 2, 3, and 4, is at least 0.37% (wt) instantaneously soluble at room temperature in water. In some preparations, composition may contain about 0.14% rebD and about 0.21% rebM in soluble form. It is understood that steviol glycoside other than rebaudioside M and rebaudioside D have poor solubility in an aqueous composition, and therefore, it is also within the scope of the invention to use one or more of compounds 1-4 to improve the solubility of other steviol glycosides other than rebaudioside M and rebaudioside D.

Therefore, the presence of compound(s) 1, 2, 3, and/or 4 can improve the solubility of one or more steviol glycosides by 5% or greater, 10% or greater, 15% or greater, 20% or greater, 25% or greater, 30% or greater, 35% or greater, 40% or greater, 45% or greater, 50% or greater, 55% or greater, 60% or greater, 65% or greater, or 70% or greater, such as about 75%. While compound 1, 2, 3, and/or 4, can improve the solubility of one or more other steviol glycosides when the compounds are present in small amounts, for example, less than 6%, of the total amount steviol glycosides in the composition, such as from about 0.5% to about 6%, or about 4% to about 6%, they can be present in amounts greater than 6%, such as greater than 6%, greater than about 8% or greater than about 10%, to provide an even greater enhancement of solubility of steviol glycosides that are different than compounds 1, 2, 3, and 4.

In some modes of practice, compound(s) 1, 2, 3, and/or 4, can be enriched in a composition. The term "enriched" refers to an increase in the amount of compound 1, 2, 3, and/or 4, relative to one or more other compounds that are present in a composition. For example, compound 1, 2, 3, and/or 4, can be enriched from a fermentation media in which the compounds were produced. In modes of practice, compound 1, 2, 3, and/or 4, can be enriched by the reduction or elimination of components that are not steviol glycosides from the fermentation composition, such as by using enrichment methods as described herein. A composition that is enriched for compound 1, 2, 3, and/or 4 can be combined with another steviol glycoside composition to improve solubility of those steviol glycosides that are not compounds 1, 2, 3, or 4.

In other modes of practice, compound(s) 1, 2, 3, and/or 4, can be enriched in a composition relative to other steviol glycosides. For example, a composition of steviol glycosides can be enriched to increase the amount(s) of compound 1, 2, 3, and/or 4 relative to one or more other steviol glycosides in the composition. Compound 1, 2, 3, and/or 4 may be enriched on the basis of their molecular weight, which can be higher than other steviol glycosides, such as Reb D and Reb M.

In exemplary modes of practice, high pressure liquid chromatography is used to prepare a steviol glycoside composition that is enriched for compound(s) 1, 2, 3, and/or 4 relative to other steviol glycosides in comparison to the amounts of steviol glycosides produced during fermentation. For example, a steviol glycoside composition can include compound 1, 2, 3, and/or 4 in an amount greater than 6%, greater than about 8%, greater than about 10%, greater than about 15%, greater than about 20%, greater than about 20%, greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95%, relative to the total amount of steviol glycosides in the composition.

For example, following an enrichment process, the steviol glycoside composition can have a combined amount of Compounds 1, 2, 3, and/or 4 in the range of about 10-30%, and a combined amount of other steviol glycosides, such as Reb D and Reb M in the range of about 70-90%.

In yet other modes of practice, compounds 1, 2, 3, and/or 4 are purified from other steviol glycosides to provide a composition comprising compounds 1, 2, 3, and/or 4 essentially free of other components (i.e., essentially free of other steviol glycoside and non-steviol glycoside compounds). Such a purified composition can be useful as an additive to other steviol glycoside composition(s), such as to increase the aqueous solubility of the other steviol glycosides to form a composition with higher steviol glycoside concentration.

Accordingly, embodiments of the invention provide a method of enhancing the solubility of a steviol glycoside in an aqueous composition which includes a step of providing an aqueous composition comprising first and second steviol glycosides. In the composition the first steviol glycoside has a branched chain of four glucose units attached to an atom of a cyclooctane group of a steviol moiety of the first steviol glycoside. Also the second steviol glycoside is different than the first steviol glycoside. For example, in the step of providing, the first steviol glycoside can be produced along with the second steviol glycoside, such as when the first and second steviol glycosides are prepared by an enzymatic process (e.g., within a cell, or in a cell-free system) Alternatively, the first steviol glycoside can be added to a composition that has the second steviol glycoside. The second steviol glycoside has a solubility in an aqueous composition that lacks the first steviol glycoside that is lower than a solubility of the second steviol glycoside in an aqueous composition that includes the first steviol glycoside.

In other words, the solubility of the second steviol glycoside increases when the first steviol glycoside is present.

Accordingly, other embodiments of the invention provides a method of enhancing the solubility of a steviol glycoside in an aqueous composition comprising a step of providing an aqueous composition comprising first and second steviol glycosides, wherein the second steviol glycoside is selected from the group consisting of rebaudioside A, rebaudioside B, rebaudioside M, rebaudioside D, rebaudioside I, rebaudioside Q, rebaudioside N, and stevioside. For example, in the step of providing, the first steviol glycoside can be produced along with the second steviol glycoside, such as when the first and second steviol glycosides are prepared by an enzymatic process (e.g., within a cell, or in a cell-free system). Alternatively, the first steviol glycoside can be added to a composition that has the second steviol glycoside. The first steviol glycoside is different from the second steviol glycoside, and has a higher molecular weight than rebaudioside M. Compounds 1-4 exemplify the first steviol glycoside. Also, the second steviol glycoside has a solubility in an aqueous composition that lacks the first steviol glycoside that is lower than a solubility of the second steviol glycoside in an aqueous composition that includes the first steviol glycoside. In other words, the solubility of the second steviol glycoside increases when the first steviol glycoside is present.

Compounds 1-4 can be purified using with preparative liquid chromatography, such as high pressure liquid chromatography (HPLC) or ultra-high pressure liquid chromatography (UHPLC). A steviol glycoside composition with compounds 1-4 can be dissolved in a mobile phase, such as a mixture of water and an alcohol (e.g., methanol) at a desired ratio (e.g., 60% water, 40% methanol, v/v). The composition can also be heated to enhance dissolution of the steviol glycoside material, such as heating at about 50° C. The solution can also be filtered prior to injection into the column, such as using a 0.2 μm filter. Phenomenex Kinetex XB-C18 5 μm, core-shell silica solid support, and stationary phase of C18 with iso-butyl side chains and TMS endcapping. The flow rate through the column can be based on column properties (such as about 20 mL/min), with a maximum pressure of 400 bar. Compounds 1-4 can be identified by their elution times from the column. In exemplary flow conditions Compounds 1-4 can elute from the column within 60 minutes. One of skill in the art will appreciate that the elution times for the Compounds 1-4 can vary with changes in solvent and/or equipment. Those experienced in art will also understand that although the process described below assumes certain order of the described steps, this order can be altered in some cases.

Sweetener compositions (also referred to as sweetening compositions), as used herein, refers to compositions that include one or more steviol glycosides, including one or more of compounds 1, 2, 3, and/or 4. For example, a sweetener composition can include compound(s) 1, 2, 3, and/or 4 along with another steviol glycoside such as RebM and/or RebD. If multiple steviol glycosides are present in the sweetener compositions, in some embodiments compounds 1, 2, 3, and/or 4 can be present in minor amounts in the composition (e.g., less than about 25%, less than about 20%, less than about 15%, or less than about 10%), of the total amount of steviol glycosides in the composition. One or more other steviol glycoside(s) such as RebM and/or RebD can be present in a major amount in the composition, such as greater than about 75%, greater than about 80%, greater than about 85%, greater than about 90%, or greater than about 95%, of the total amount of steviol glycosides in the composition.

The sweetener composition can optionally include another sweetener, an additive, a liquid carrier, or combinations thereof. Sweetener compositions are used to sweeten other compositions (sweetenable compositions) such as foods, beverages, medicines, oral hygiene compositions, nutraceuticals, and the like.

Sweetenable compositions, as used herein, mean substances which are contacted with the mouth of man or animal, including substances which are taken into but subsequently ejected from the mouth (such as a mouthwash rinse) and substances which are drunk, eaten, swallowed or otherwise ingested, and are suitable for human or animal consumption when used in a generally acceptable range. Sweetenable compositions are precursor compositions to sweetened compositions and are converted to sweetened compositions by combining the sweetenable compositions with at least one sweetening composition and optionally one or more other sweetenable compositions and/or other ingredients.

Sweetened compositions, as used herein, mean substances that are derived from constituents including at least one sweetenable composition and at least one sweetener composition. In some modes of practice, a sweetened composition may be used itself as a sweetening composition to sweeten still yet further sweetenable compositions. In some modes of practice, a sweetened composition may be used as a sweetenable composition that is further sweetened with one or more additional sweetening compositions. For example, a beverage with no sweetener component is a type of sweetenable composition. A sweetener composition comprising at least one of compounds 1, 2, 3, and/or 4, optionally along with another steviol glycoside, such as RebM and/or RebD, can be added to the un-sweetened beverage, thereby providing a sweetened beverage. The sweetened beverage is a type of sweetened composition.

In some preparations, steviol glycosides, including compounds 1, 2, 3, and/or 4, provide the sole sweetener component in a sweeteneing composition.

In some embodiments, a sweetening composition comprises steviol glycosides, including compounds 1, 2, 3, and/or 4, in an amount effective to provide a sweetness strength equivalent to a specified amount of sucrose. The amount of sucrose in a reference solution may be described in degrees Brix (° Bx). One degree Brix is 1 gram of sucrose in 100 grams of solution and represents the strength of the solution as percentage by weight (% w/w). For example, a sweetener composition contains one or more steviol glycosides, including compounds 1, 2, 3, and/or 4, in an amount effective to provide a sweetness equivalent from about 0.50 to 14 degrees Brix of sugar when present in a sweetened composition, such as, for example, from about 5 to about 11 degrees Brix, from about 4 to about 7 degrees Brix, or about 5 degrees Brix.

The amount of steviol glycosides in the sweetener composition may vary. Steviol glycosides, including compounds 1, 2, 3, and/or 4, can be present in a sweetener composition in any amount to impart the desired sweetness when the sweetener composition is incorporated into a sweetened composition. For example, Reb M and/or Reb D, along with one or more of compounds 1, 2, 3, and/or 4, are present in the sweetener composition in an amount effective to provide total steviol glycoside concentration from about 1 ppm to about 10,000 ppm when present in a sweetened composition, In another embodiment, the steviol glycosides are present in the sweetener composition in an amount effective to provide a steviol glycoside concentration in the range of about 10 ppm to about 1,000 ppm, more specifically about 10 ppm to about 800 ppm, about 50 ppm to about 800 ppm, about 50 ppm to about 600 ppm, or about 200 ppm to about 500 ppm. Unless otherwise expressly stated, ppm is on a weight basis.

In some embodiments, a sweetener composition having the steviol glycosides, including compounds 1, 2, 3, and/or 4, also contain one or more additional non-steviol glycoside sweetener compound(s). The non-steviol glycoside sweetener compounds can be any type of sweetener, for example, a sweetener obtained from a plant or plant product, or a physically or chemically modified sweetener obtained from a plant, or a synthetic sweetener.

For example, exemplary non-steviol glycoside sweeteners include sucrose, fructose, glucose, erythritol, maltitol, lactitol, sorbitol, mannitol, xylitol, tagatose, trehalose, galactose, rhamnose, cyclodextrin (e.g., α-cyclodextrin, β-cyclodextrin, and γ-cyclodextrin), ribulose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, glucosamine, mannosamine, fucose, fuculose, glucuronic acid, gluconic acid, glucono-lactone, abequose, galactosamine, xylo-oligosaccharides (xylotriose, xylobiose and the like), gentio-oligoscaccharides (gentiobiose, gentiotriose, gentiotetraose and the like), galacto-oligosaccharides, sorbose, ketotriose (dehydroxyacetone), aldotriose (glyceraldehyde), nigero-oligosaccharides, fructooligosaccharides (kestose, nystose and the like), maltotetraose, maltotriol, tetrasaccharides, mannan-oligosaccharides, malto-oligosaccharides (maltotriose, maltotetraose, maltopentaose, maltohexaose, maltoheptaose and the like), dextrins, lactulose, melibiose, raffinose, rhamnose, ribose, isomerized liquid sugars such as high fructose corn/starch syrup (HFCS/HFSS) (e.g., HFCS55, HFCS42, or HFCS90), coupling sugars, soybean oligosaccharides, glucose syrup and combinations thereof. D- or L-configurations can be used when applicable.

The steviol glycosides (including compounds 1, 2, 3, and/or 4), and carbohydrate sweetener may be present in any weight ratio, such as, for example, from about 1:14,000 to about 100:1, such as, for example, about 1:100. Carbohydrates are present in the sweetener composition in an amount effective to provide a concentration from about 100 ppm to about 140,000 ppm when present in a sweetened composition, such as, for example, a beverage.

In other embodiments, the sweetener composition including the steviol glycosides (including compounds 1, 2, 3, and/or 4), additionally include one or more synthetic sweeteners. Preferably, a synthetic has a sweetness potency greater than sucrose, fructose, and/or glucose, yet has less calories than sucrose, fructose, and/or glucose. Exemplary synthetic non-steviol glycoside sweeteners include sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof. In embodiments where the sweetener composition includes the steviol glycosides (including compounds 1, 2, 3, and/or 4) and synthetic sweetener, the synthetic sweetener can be present in an amount effective to provide a concentration from about 0.3 ppm to about 3,500 ppm when present in a sweetened composition, such as, for example, a beverage.

The sweetener compositions can be customized to provide a desired calorie content. For example, sweetener compositions can be "full-calorie", such that they impart the desired sweetness when added to a sweetenable composition (such as, for example, a beverage) and have about 120 calories per 8 oz serving. Alternatively, sweetener compositions can be "mid-calorie", such that they impart the desired sweetness when added to a sweetenable composition (such as, for example, as beverage) and have less than about 60 calories per 8 oz serving. In other embodiments, sweetener compositions can be "low-calorie", such that they impart the desired sweetness when added to a sweetenable composition (such as, for example, as beverage) and have less than 40 calories per 8 oz serving. In still other embodiments, the sweetener compositions can be "zero-calorie", such that they impart the desired sweetness when added to a sweetenable composition (such as, for example, a beverage) and have less than 5 calories per 8 oz. serving.

The weight ratio of the total amount of sweetener compositions used to sweeten a sweetened composition can vary over a wide range. In many embodiments, this weight ratio is in the range from 1:10,000 to 10:1.

In addition to the steviol glycosides (including compounds 1, 2, 3, and/or 4) the sweetener compositions can optionally include a liquid carrier, binder matrix, additional additives, and/or the like. In some embodiments, the sweetener composition contains additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, weighing agents, gums, antioxidants, colorants, flavonoids, alcohols, polymers and combinations thereof. In some embodiments, the additives act to improve the temporal and flavor profile of the sweetener to provide a sweetener composition with a favorable taste, such as a taste similar to sucrose.

In one embodiment, the sweetener compositions with steviol glycosides (including compounds 1, 2, 3, and/or 4) contain one or more polyols. The term "polyol", as used herein, refers to a molecule that contains more than one hydroxyl group. In some embodiments, a polyol may be a diol, triol, or a tetraol which contains 2, 3, and 4 hydroxyl groups respectively. A polyol also may contain more than 4 hydroxyl groups, such as a pentaol, hexaol, heptaol, or the like, which contain 5, 6, 7, or even more hydroxyl groups, respectively. Additionally, a polyol also may be a sugar alcohol, polyhydric alcohol, polymer comprising OH functionality, or polyalcohol which is a reduced form of a carbohydrate, wherein a carbonyl group (aldehyde or ketone, reducing sugar) has been reduced to a primary or secondary hydroxyl group.

Exemplary polyols include erythritol, maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect the taste of the sweetener composition.

Exemplary amounts of polyol provide a concentration in the range of about 100 ppm to about 250,000 ppm when present in a sweetened composition, more specifically about 400 ppm to about 80,000 ppm, or about 5,000 ppm to about 40,000 ppm, based on the total weight of the sweetened composition.

Exemplary amino acid additives include any compound comprising at least one amino functionality and at least one acid functionality. Examples include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid (α-, β-, and/or δ-isomers), glutamine, hydroxyproline, taurine, norvaline, sarcosine, and their salt forms such as sodium or potassium salts or acid salts.

Exemplary amounts of amino acid provide a concentration in the range of about 10 ppm to about 50,000 ppm, or more specifically about 1,000 ppm to about 10,000 ppm, about 2,500 ppm to about 5,000 ppm, or about 250 ppm to about 7,500 ppm, based on the total weight of the sweetened composition.

Exemplary sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

Exemplary nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil). In some embodiments, a nucleotide can be present in the sweetener composition to provide a concentration in the range of about 5 ppm to about 1,000 ppm based on the total weight of the sweetened composition.

Exemplary organic acid additives include any compound which comprises a —COOH moiety, such as, for example, C2-C30 carboxylic acids, substituted hydroxyl C2-C30 carboxylic acids, butyric acid (ethyl esters), substituted butyric acid (ethyl esters), benzoic acid, substituted benzoic acids (e.g., 2,4-dihydroxybenzoic acid), substituted cinnamic acids, hydroxyacids, substituted hydroxybenzoic acids, anisic acid substituted cyclohexyl carboxylic acids, tannic acid, aconitic acid, lactic acid, tartaric acid, citric acid, isocitric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration. Salts of organic acids are also contemplated. In exemplary embodiments, an organic acid or salt thereof is present in the sweetener composition in an amount from about 10 ppm to about 5,000 ppm, based on the total weight of the sweetener composition.

Exemplary inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

Exemplary bitter compound additives include, but are not limited to, caffeine, quinine, urea, bitter orange oil, naringin, quassia, and salts thereof.

Exemplary flavorant and flavoring ingredient additives, but are not limited to, vanillin, vanilla extract, mango extract, cinnamon, citrus, coconut, ginger, viridiflorol, almond, menthol (including menthol without mint), grape skin extract, and grape seed extract. In some embodiments, a flavorant is present in the sweetener composition in an amount effective to provide a concentration from about 0.1 ppm to about 4,000 ppm when present in a sweetened composition, such as, for example, a beverage, based on the total weight of the sweetened composition.

Exemplary polymer additives include, chitosan, pectin, pectic, pectinic, polyuronic, polygalacturonic acid, starch, food hydrocolloid or crude extracts thereof (e.g., gum acacia Senegal (Fibergum™), gum acacia seyal, carageenan), poly-L-lysine (e.g., poly-L-a-lysine or poly-L-e-lysine), poly-L-ornithine (e.g., poly-L-a-ornithine or poly-L-e-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers. In some embodiments, a polymer additive is present in the sweetener composition in an amount effective to provide a concentration from about 30 ppm to about 2,000 ppm when present in a sweetened composition, such as, for example, a beverage, based on the total weight of the sweetened composition.

Exemplary protein or protein hydrolysate additives include, but are not limited to, bovine serum albumin (BSA), whey protein, soluble rice protein, soy protein, protein isolates, protein hydrolysates, reaction products of protein hydrolysates, glycoproteins, and/or proteoglycans containing amino acids, collagen (e.g., gelatin), partially hydrolyzed collagen (e.g., hydrolyzed fish collagen), and collagen hydrolysates (e.g., porcine collagen hydrolysate). In some embodiments, a protein hydrosylate is present in the sweetener composition in an amount effective to provide a concentration from about 200 ppm to about 50,000 ppm when present in a sweetened composition, such as, for example, a beverage, based on the total weight of the sweetened composition.

Exemplary surfactant additives include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like. In some embodiments, a surfactant additive is present in the sweetener composition in an amount effective to provide a concentration from about 30 ppm to about 2,000 ppm when present in a sweetened composition, such as, for example, a beverage, based on the total weight of the sweetened composition.

Exemplary flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like. In some embodiments, a flavonoid additive is present in the sweetener composition in an amount effective to provide a concentration from about 0.1 ppm to about 1,000 ppm when present in sweetened composition, such as, for example, a beverage, based on the total weight of the sweetened composition.

Exemplary alcohol additives include, but are not limited to, ethanol. In some embodiments, an alcohol additive is present in the sweetener composition in an amount effective to provide a concentration from about 625 ppm to about 10,000 ppm when present in a sweetened composition, such as, for example, a beverage, based on the total weight of the sweetened composition.

The sweetener composition can also contain one or more functional ingredients, which provide a real or perceived heath benefit to the composition. Functional ingredients include, but are not limited to, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

Saponins are glycosidic plant products comprising an aglycone ring structure and one or more sugar moieties. The combination of the nonpolar aglycone and the water soluble sugar moiety gives saponins surfactant properties, which allow them to form a foam when shaken in an aqueous solution.

As used herein "antioxidant" refers to any substance which inhibits, suppresses, or reduces oxidative damage to cells and biomolecules. Without being bound by theory, it is believed that antioxidants inhibit, suppress, or reduce oxidative damage to cells or biomolecules by stabilizing free radicals before they can cause harmful reactions. As such, antioxidants may prevent or postpone the onset of some degenerative diseases.

Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, a-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-a-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), aronia extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolf erry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains, or cereal grains.

Particular antioxidants belong to the class of phytonutrients called polyphenols (also known as "polyphenolics"), which are a group of chemical substances found in plants, characterized by the presence of more than one phenol group per molecule. A variety of health benefits may be derived from polyphenols, including prevention of cancer, heart disease, and chronic inflammatory disease and improved mental strength and physical strength, for example. Suitable polyphenols for embodiments of this invention, include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials, and combinations thereof.

Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins, and combinations thereof.

As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

As used herein, the at least one vitamin may be single vitamin or a plurality of vitamins as a functional ingredient for the sweetener and sweetened compositions provided herein. Generally, according to particular embodiments of this invention, the at least one vitamin is present in the sweetener composition or sweetened composition in an amount sufficient to promote health and wellness.

Vitamins are organic compounds that the human body needs in small quantities for normal functioning. The body uses vitamins without breaking them down, unlike other nutrients such as carbohydrates and proteins. To date, thirteen vitamins have been recognized, and one or more can be used in the functional sweetener and sweetened compositions herein. Suitable vitamins include, vitamin A, vitamin D, vitamin E, vitamin K, vitamin B1, vitamin B2, vitamin B3, vitamin B5, vitamin B6, vitamin B7, vitamin B9, vitamin B 12, and vitamin C. Many of vitamins also have alternative chemical names, non-limiting examples of which are provided below.

In certain embodiments, the functional ingredient comprises glucosamine or chondroitin sulfate. Glucosamine, also called chitosamine, is an amino sugar that is believed to be an important precursor in the biochemical synthesis of glycosylated proteins and lipids. D-glucosamine occurs in the cartilage in the form of glucosamine-6-phosphate, which is synthesized from fructose-6-phosphate and glutamine. However, glucosamine also is available in other forms, non-limiting examples of which include glucosamine hydrochloride, glucosamine sulfate, N-acetyl-glucosamine, or any other salt forms or combinations thereof.

In certain embodiments, the functional ingredient comprises at least one mineral. Minerals comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages. In particular embodiments of this invention, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In certain embodiments, the functional ingredient comprises at least one preservative. In particular embodiments of this invention, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone.

In certain embodiments, the functional ingredient is at least one hydration agent. Hydration products help the body to replace fluids that are lost through excretion. In a particular embodiment, the hydration product is a composition that helps the body replace fluids that are lost during exercise. Accordingly, in a particular embodiment, the hydration product is an electrolyte, non-limiting examples of which include sodium, potassium, calcium, magnesium, chloride, phosphate, bicarbonate, and combinations thereof. In particular embodiments of this invention, the hydration product is a carbohydrate to supplement energy stores burned by muscles. In another particular embodiment, the hydration agent is at least one flavanol that provides cellular rehydration. Flavanols are a class of substances present in plants, and generally comprise a 2-phenylbenzopyrone molecular skeleton attached to one or more chemical moieties. In a particular embodiment, the hydration agent comprises a glycerol solution to enhance exercise endurance. The ingestion of a glycerol containing solution has been shown to provide beneficial physiological effects, such as expanded blood volume, lower heart rate, and lower rectal temperature.

In certain embodiments, the functional ingredient comprises at least one probiotic, prebiotic and combination thereof. Probiotics comprise microorganisms that benefit health when consumed in an effective amount. Desirably, probiotics beneficially affect the human body's gastrointestinal microflora and impart health benefits apart from nutrition. Probiotics may include, without limitation, bacteria, yeasts, and fungi. Examples of probiotics include, but are not limited to, bacteria of the genus Lactobacilli, Bifidobacteria, Streptococci, or combinations thereof, that confer beneficial effects to humans. Prebiotics are compositions that promote the growth of beneficial bacteria in the intestines.

In certain embodiments, the functional ingredient is at least one weight management agent. As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant" describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

In certain embodiments, the functional ingredient is at least one osteoporosis management agent. In certain embodiments, the osteoporosis management agent is at least one calcium source. According to a particular embodiment, the calcium source is any compound containing calcium, including salt complexes, solubilized species, and other forms of calcium. According to a particular embodiment, the osteoporosis management agent is a magnesium source. The magnesium source is any compound containing magnesium, including salt complexes, solubilized species, and other forms of magnesium. In other embodiments, the osteoporosis agent is chosen from vitamins D, C, K, their precursors and/or beta-carotene and combinations thereof.

In certain embodiments, the functional ingredient is at least one phytoestrogen. In one embodiment, a sweetener composition comprises at least one phytoestrogen. As used herein, "phytoestrogen" refers to any substance which, when introduced into a body causes an estrogen-like effect of any degree. Examples of suitable phytoestrogens for embodiments of this invention include, but are not limited to, isoflavones, stilbenes, lignans, resorcyclic acid lactones, coumestans, coumestrol, equol, and combinations thereof.

Isoflavones belong to the group of phytonutrients called polyphenols. In general, polyphenols (also known as "polyphenolics"), are a group of chemical substances found in plants, characterized by the presence of more than one phenol group per molecule. Suitable phytoestrogen isoflavones in accordance with embodiments of this invention include genistein, daidzein, glycitein, biochanin A, formononetin, their respective glycosides and glycoside conjugates, matairesinol, secoisolariciresinol, enterolactone, enterodiol, textured vegetable protein, and combinations thereof.

In certain embodiments, the functional ingredient is at least one long chain primary aliphatic saturated alcohol. Non-limiting examples of particular long-chain primary aliphatic saturated alcohols for use in particular embodiments of the invention include the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In certain embodiments, the functional ingredient is at least one phytosterol, phytostanol or combination thereof. As used herein, the phrases "stanol", "plant stanol" and "phytostanol" are synonymous. Sterols are a subgroup of steroids with a hydroxyl group at C-3. Generally, phytosterols have a double bond within the steroid nucleus, like cholesterol; however, phytosterols also may comprise a substituted sidechain (R) at C-24, such as an ethyl or methyl group, or an additional double bond. The structures of phytosterols are well known to those of skill in the art. Phytosterols well known to those or ordinary skill in the art include 4-desmethylsterols (e.g., β-sitosterol, campesterol, stigmasterol, brassicasterol, 22-dehydrobrassicasterol, and Δ5-avenasterol), 4-monomethyl sterols, and 4,4-dimethyl sterols (triterpene alcohols) (e.g., cycloartenol, 24-methylenecycloartanol, and cyclobranol). Examples of phytostanols include β-sitostanol, campestanol, cycloartanol, and saturated forms of other triterpene alcohols.

Generally, the amount of functional ingredient in the sweetener composition or sweetened composition varies widely depending on the particular sweetener composition or sweetened composition and the desired functional ingredient. Those of ordinary skill in the art will readily acertain the appropriate amount of functional ingredient for each sweetener composition or sweetened composition.

Steviol glycosides, including compounds 1, 2, 3, and/or 4, or sweetener compositions comprising teviol glycosides, including compounds 1, 2, 3, and/or 4, can be incorporated in any known edible material (referred to herein as a "sweetenable composition") or other composition intended to be ingested and/or contacted with the mouth of a human or animal, such as, for example, pharmaceutical compositions, edible gel mixes and compositions, dental and oral hygiene compositions, foodstuffs (confections, condiments, chewing gum, cereal compositions, baked goods, baking goods, cooking adjuvants, dairy products, and tabletop sweetener compositions), beverages, and other beverage products (e.g., beverage mixes, beverage concentrates, etc.).

In one embodiment, a sweetened composition is derived from ingredients comprising a sweetenable composition and additionally steviol glycosides, including compounds 1, 2, 3, and/or 4. In another embodiment, the sweetened composition is derived from ingredients comprising a sweetener composition comprising Steviol glycosides, including compounds 1, 2, 3, and/or 4. The sweetened compositions can optionally include one or more additives, liquid carriers, binders, sweeteners, functional ingredients, other adjuvants, and combinations thereof.

In one embodiment, a pharmaceutical composition contains a pharmaceutically active substance (including prodrug forms thereof) and steviol glycosides, including compounds 1, 2, 3, and/or 4. In another embodiment, a pharmaceutical composition contains a pharmaceutically active substance and a sweetener composition comprising steviol glycosides, including compounds 1, 2, 3, and/or 4. The steviol glycoside sweetener composition can be present as an excipient material in the pharmaceutical composition, which can mask a bitter or otherwise undesirable taste of a pharmaceutically active substance or another excipient material. The pharmaceutical composition may be in the form of a tablet, a capsule, a liquid, an aerosol, a powder, an effervescent tablet or powder, a syrup, an emulsion, a suspension, a solution, or any other form for providing the pharmaceutical composition to a patient. In particular embodiments, the pharmaceutical composition may be in a form for oral administration, buccal administration, sublingual administration, or any other route of administration as known in the art.

As referred to herein, "pharmaceutically active substance" means any drug, drug formulation, medication, prophylactic agent, therapeutic agent, or other substance having biological activity. Pharmaceutically active substances also include prodrug forms of these. As referred to herein, "excipient material" refers to any other ingredient used in a pharmaceutically active composition used in combination with pharmaceutically active substance(s) that are present (including prodrugs thereof. Excipients included but are not limited to inactive substances used as a vehicle for an active ingredient, such as any material to facilitate handling, stability, dispersibility, wettability, and/or release kinetics of a pharmaceutically active substance.

Suitable pharmaceutically active substances include, but are not limited to, medications for the gastrointestinal tract or digestive system, for the cardiovascular system, for the central nervous system, for pain or consciousness, for musculo-skeletal disorders, for the eye, for the ear, nose and oropharynx, for the respiratory system, for endocrine problems, for the reproductive system or urinary system, for contraception, for obstetrics and gynecology, for the skin, for infections and infestations, for immunology, for allergic disorders, for nutrition, for neoplastic disorders, for diagnostics, for euthanasia, or other biological functions or disorders.

Examples of suitable pharmaceutically active substances for embodiments of the present invention include, but are not limited to, antacids, reflux suppressants, antiflatulents, antidopaminergics, proton pump inhibitors, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, peripheral activators, ACE inhibitors, angiotensin receptor blockers, alpha blockers, anticoagulants, heparin, antiplatelet drugs, fibrinolytics, anti-hemophilic factors, haemostatic drugs, hypolipidaemic agents, statins, hynoptics, anaesthetics, antipsychotics, antidepressants, anti-emetics, anticonvulsants, antiepileptics, anxiolytics, barbiturates, movement disorder drugs, stimulants, benzodiazepines, cyclopyrrolones, dopamine antagonists, antihistamines, cholinergics, anticholinergics, emetics, cannabinoids, analgesics, muscle relaxants, antibiotics, aminoglycosides, anti-virals, anti-fungals, anti-inflammatories, anti-gluacoma drugs, sympathomimetics, steroids, ceruminolytics, bronchodilators, NSAIDS, antitussive, mucolytics, decongestants, corticosteroids, androgens, antiandrogens, gonadotropins, growth hormones, insulin, antidiabetics, thyroid hormones, calcitonin, diphosponates, vasopressin analogues, alkalizing agents, quinolones, anticholinesterase, sildenafil, oral contraceptives, Hormone Replacement Therapies, bone regulators, follicle stimulating hormones, luteinizings hormones, gamolenic acid, progestogen, dopamine agonist, oestrogen, prostaglandin, gonadorelin, clomiphene, tamoxifen, diethylstilbestrol, antileprotics, antituberculous drugs, antimalarials, anthelmintics, antiprotozoal, antiserums, vaccines, interferons, tonics, vitamins, cytotoxic drugs, sex hormones, aromatase inhibitors, somatostatin inhibitors, or similar type substances, or combinations thereof. Such components generally are recognized as safe (GRAS) and/or are U.S. Food and Drug Administration (FDA)-approved.

The pharmaceutical composition also may comprise other pharmaceutically acceptable excipient materials in addition to a sweetener composition comprising steviol glycosides, including compounds 1, 2, 3, and/or 4. Examples of other suitable excipient materials for embodiments of this invention include, but are not limited to, other sweetening compounds, antiadherents, binders (e.g., microcrystalline cellulose, gum tragacanth, or gelatin), liquid carriers, coatings, disintegrants, fillers, diluents, softeners, emulsifiers, flavoring agents, coloring agents, adjuvants, lubricants, functional agents (e.g., nutrients), viscosity modifiers, bulking agents, glidiants (e.g., colloidal silicon dioxide) surface active agents, osmotic agents, diluents, or any other non-active ingredient, or combinations thereof. For example, the pharmaceutical compositions of the present invention may include excipient materials selected from the group consisting of calcium carbonate, coloring agents, whiteners, preservatives, and flavors, triacetin, magnesium stearate, sterotes, natural or artificial flavors, essential oils, plant extracts, fruit essences, gelatins, or combinations thereof.

In one embodiment, an edible gel or edible gel mix comprises a sweetener composition comprising steviol glycosides, including compounds 1, 2, 3, and/or 4. The edible gel or edible gel mixes can optionally include additives, functional ingredients or combinations thereof. Compounds 1, 2, 3, and/or 4, or a mixture of compounds 1, 2, 3, and/or 4 with one or more other steviol glycosides, such as Reb D or Reb M, can constitute a sweetener composition of the present invention. However, in many embodiments, a sweetener compositions comprises compounds 1, 2, 3, and/or 4, or a mixture of compounds 1, 2, 3, and/or 4 with one or more other steviol glycosides, such as Reb D or Reb M and one or more other ingredient(s) that is not a steviol glycoside.

Edible gels are gels that can be eaten by a human or animal. Gels often appear to be solid, jelly-like materials. Non-limiting examples of edible gel compositions for use in particular embodiments include gel desserts, puddings, jellies, pastes, trifles, aspics, marshmallows, gummy candies, or the like. Edible gel mixes generally are powdered or granular solids to which a fluid may be added to form an edible gel composition. Because edible gel products found in the marketplace typically are sweetened with sucrose, it is desirable to sweeten edible gels with an alternative sweetener in order provide a low-calorie or non-calorie alternative.

Non-limiting examples of gelling ingredients for use in particular embodiments include gelatin, alginate, carageenan, gum, pectin, konjac, agar, food acid, rennet, starch, starch derivatives, and combinations thereof. It is well known to those having ordinary skill in the art that the amount of gelling ingredient used in an edible gel mix or an edible gel composition varies considerably depending on a number of factors, such as the particular gelling ingredient used, the particular fluid base used, and the desired properties of the gel.

Edible gel mixes and edible gels may be prepared using other ingredients in addition to the sweetener composition comprising steviol glycosides, including compounds 1, 2, 3, and/or 4, and the gelling agent. Non-limiting examples of other ingredients for use in particular embodiments include a food acid, a salt of a food acid, a buffering system, a bulking agent, a sequestrant, a cross-linking agent, one or more flavors, one or more colors, and combinations thereof.

In one embodiment, a dental composition comprises a sweetener composition comprising steviol glycosides, including compounds 1, 2, 3, and/or 4. Dental compositions generally comprise an active dental substance and a base material. A sweetener composition comprising steviol glycosides, including compounds 1, 2, 3, and/or 4, can be used as the base material to sweeten the dental composition. The dental composition may be in the form of any oral composition used in the oral cavity such as mouth freshening agents, gargling agents, mouth rinsing agents, toothpaste, tooth polish, dentifrices, mouth sprays, teeth-whitening agent, dental floss, compositions to treat one or more oral indications (e.g., gingivitis), and the like, for example.

As referred to herein, “active dental substance” means any composition which can be used to improve the aesthetic appearance and/or health of teeth or gums or prevent dental caries. As referred to herein, “base material” refers to any inactive substance used as a vehicle for an active dental substance, such as any material to facilitate handling, stability, dispersibility, wettability, foaming, and/or release kinetics of an active dental substance.

Suitable active dental substances for embodiments of this invention include, but are not limited to, substances which remove dental plaque, remove food from teeth, aid in the elimination and/or masking of halitosis, prevent tooth decay, and prevent gum disease (i.e., Gingiva). Examples of suitable active dental substances for embodiments of the present invention include, but are not limited to, anticaries drugs, fluoride, sodium fluoride, sodium monofluorophosphate, stannos fluoride, hydrogen peroxide, carbamide peroxide (i.e., urea peroxide), antibacterial agents, plaque removing agents, stain removers, anticalculus agents, abrasives, baking soda, percarbonates, perborates of alkali and alkaline earth metals, or similar type substances, or combinations thereof. Such components generally are recognized as safe (GRAS) and/or are U.S. Food and Drug Administration (FDA)-approved.

In a particular embodiment, a dental composition comprises a sweetener composition comprising steviol glycosides, including compounds 1, 2, 3, and/or 4, and an active dental substance. Generally, the amount of the sweetener varies widely depending on the nature of the particular dental composition and the desired degree of sweetness. Those skilled in the art will be able to discern a suitable amount of sweetener for such dental composition. In a particular embodiment, steviol glycosides, including compounds 1, 2, 3, and/or 4, is present in the dental composition in a total amount in the range of about 1 to about 5,000 ppm of the dental composition and the at least one additive is present in the dental composition in an amount in the range of about 0.1 to about 100,000 ppm of the dental composition.

Foodstuffs include, but are not limited to, confections, condiments, chewing gum, cereal, baked goods, and dairy products.

In one embodiment, a confection comprises a sweetener composition comprising steviol glycosides, including compounds 1, 2, 3, and/or 4. As referred to herein, “confection” can mean a sweet, a lollie, a confectionery, or similar term. The confection generally contains a base composition component and a sweetener component. A sweetener composition comprising steviol glycosides, including compounds 1, 2, 3, and/or 4 N can serve as the sweetener component. The confection may be in the form of any food that is typically perceived to be rich in sugar or is typically sweet. According to particular embodiments of the present invention, the confections may be bakery products such as pastries; desserts such as yogurt, jellies, drinkable jellies, puddings, Bavarian cream, blancmange, cakes, brownies, mousse and the like, sweetened food products eaten at tea time or following meals; frozen foods; cold confections, e. g. types of ice cream such as ice cream, ice milk, lacto-ice and the like (food products in which sweeteners and various other types of raw materials are added to milk products, and the resulting mixture is agitated and frozen), and ice confections such as sherbets, dessert ices and the like (food products in which various other types of raw materials are added to a sugary liquid, and the resulting mixture is agitated and frozen); general confections, e. g., baked confections or steamed confections such as crackers, biscuits, buns with bean-jam filling, halvah, alfajor, and the like; rice cakes and snacks; table top products; general sugar confections such as chewing gum (e.g. including compositions which comprise a substantially water-insoluble, chewable gum base, such as chicle or substitutes thereof, including jetulong, guttakay rubber or certain comestible plant derived or synthetic resins or waxes), hard candy, soft candy, mints, nougat candy, jelly beans, fudge, toffee, taffy, Swiss milk tablet, licorice candy, chocolates, gelatin candies, marshmallow, marzipan, divinity, cotton candy, and the like; sauces including fruit flavored sauces, chocolate sauces and the like; edible gels; cremes including butter cremes, flour pastes, whipped cream and the like; jams including strawberry jam, marmalade and the like; and breads including sweet breads and the like or other starch products, and combinations thereof. As referred to herein, “base composition” means any composition which can be a food item and provides a matrix for carrying the sweetener component.

In a particular embodiment, steviol glycosides including compounds 1, 2, 3, and/or 4, are present in the confection in an amount in the range of about 30 ppm to about 6000 ppm of the confection, or about 1 ppm to about 10,000 ppm of the confection.

In another embodiment, a condiment comprises steviol glycosides, including compounds 1, 2, 3, and/or 4. In another embodiment a condiment comprises a sweetener composition comprising steviol glycosides, including compounds 1, 2, 3, and/or 4. Condiments, as used herein, are compositions used to enhance or improve the flavor of a food or beverage. Non-limiting examples of condiments include ketchup (catsup); mustard; barbecue sauce; butter; chili sauce; chutney; cocktail sauce; curry; dips; fish sauce; horseradish; hot sauce; jellies, jams, marmalades, or preserves; mayonnaise; peanut butter; relish; remoulade; salad dressings (e.g., oil and vinegar, Caesar, French, ranch, bleu cheese, Russian, Thousand Island, Italian, and balsamic vinaigrette), salsa; sauerkraut; soy sauce; steak sauce; syrups; tartar sauce; and Worcestershire sauce.

In one embodiment, a chewing gum composition comprises a sweetener composition comprising steviol glycosides, including compounds 1, 2, 3, and/or 4. Chewing gum compositions generally comprise a water-soluble portion and a water-insoluble chewable gum base portion. The water soluble portion, which typically includes the sweetener or sweetener composition, dissipates with a portion of the flavoring agent over a period of time during chewing while the insoluble gum base portion is retained in the mouth. The insoluble gum base generally determines whether a gum is considered chewing gum, bubble gum, or a functional gum.

In a particular embodiment, a chewing gum composition comprises or a sweetener composition comprising steviol glycosides, including compounds 1, 2, 3, and/or 4 and a gum base. In a particular embodiment, steviol glycosides, including compounds 1, 2, 3, and/or 4 are present in the chewing gum composition in a total amount in the range of about 1 ppm to about 10,000 ppm of the chewing gum composition.

In one embodiment, a cereal composition comprises a sweetener composition comprising steviol glycosides, including compounds 1, 2, 3, and/or 4. Cereal compositions typically are eaten either as staple foods or as snacks. Non-limiting examples of cereal compositions for use in particular embodiments include ready-to-eat cereals as well as hot cereals. Ready-to-eat cereals are cereals which may be eaten without further processing (i.e. cooking) by the consumer. Examples of ready-to-eat cereals include breakfast cereals and snack bars. Breakfast cereals typically are processed to produce a shredded, flaky, puffy, or extruded form. Breakfast cereals generally are eaten cold and are often mixed with milk and/or fruit. Snack bars include, for example, energy bars, rice cakes, granola bars, and nutritional bars. Hot cereals generally are cooked, usually in either milk or water, before being eaten. Non-limiting examples of hot cereals include grits, porridge, polenta, rice, and rolled oats.

A sweetener composition comprising steviol glycosides, including compounds 1, 2, 3, and/or 4, can be is added to the cereal composition as a coating, such as, for example, by combining a sweetener comprising the steviol glycosides with a food grade oil and applying the mixture onto the cereal. In a different embodiment, a sweetener composition comprising the steviol glycosides and the food grade oil may be applied to the cereal separately, by applying either the oil or the sweetener first. A sweetener composition comprising steviol glycosides can also be added to the cereal composition as a glaze. Steviol glycosides can be added as a glaze by combining with a glazing agent and a food grade oil or fat and applying the mixture to the cereal. In yet another embodiment, a gum system, such as, for example, gum acacia, carboxymethyl cellulose, or algin, may be added to the glaze to provide structural support. In addition, the glaze also may include a coloring agent, and also may include a flavor. A sweetener composition comprising steviol glycosides can also be added to the cereal composition as a frosting. In one such embodiment, a sweetener composition comprising steviol glycosides is combined with water and a frosting agent and then applied to the cereal.

In a particular embodiment, steviol glycosides are present in the cereal composition in an amount in the range of about 0.02 to about 1.5 weight percent of the cereal composition.

In another embodiment, a baked good comprises a sweetener composition comprising steviol glycosides, including compounds 1, 2, 3, and/or 4. Baked goods, as used herein, include ready to eat and all ready to bake products, flours, and mixes requiring preparation before serving. Non-limiting examples of baked goods include cakes, crackers, cookies, brownies, muffins, rolls, bagels, donuts, strudels, pastries, croissants, biscuits, bread, bread products, and buns.

Exemplary baked goods can be classified into three groups: bread-type doughs (e.g., white breads, variety breads, soft buns, hard rolls, bagels, pizza dough, and flour tortillas), sweet doughs (e.g., danishes, croissants, crackers, puff pastry, pie crust, biscuits, and cookies), and batters (e.g., cakes such as sponge, pound, devil’s food, cheesecake, and layer cake, donuts or other yeast raised cakes, brownies, and muffins). Doughs generally are characterized as being flour-based, whereas batters are more water-based.

Baked goods in accordance with particular embodiments of this invention generally comprise a combination of sweetener, water, and fat. Baked goods made in accordance with many embodiments of this invention also contain flour in order to make a dough or a batter. The term “dough” as used herein is a mixture of flour and other ingredients stiff enough to knead or roll. The term “batter” as used herein consists of flour, liquids such as milk or water, and other ingredients, and is thin enough to pour or drop from a spoon.

In one embodiment, a dairy product comprises a sweetener composition comprising comprising steviol glycosides, including compounds 1, 2, 3, and/or 4. Dairy products and processes for making dairy products suitable for use in this invention are well known to those of ordinary skill in the art. Dairy products, as used herein, comprise milk or foodstuffs produced from milk. Non-limiting examples of dairy products suitable for use in embodiments of this invention include milk, milk cream, sour cream, creme fraiche, buttermilk, cultured buttermilk, milk powder, condensed milk, evaporated milk, butter, cheese, cottage cheese, cream cheese, yogurt, ice cream, frozen custard, frozen yogurt, gelato, via, piima, filmjOlk, kajmak, kephir, viili, kumiss, airag, ice milk, casein, ayran, lassi, khoa, or combinations thereof. Milk is a fluid secreted by the mammary glands of female mammals for the nourishment of their young. The female ability to produce milk is one of the defining characteristics of mammals and provides the primary source of nutrition for newborns before they are able to digest more diverse foods. In particular embodiments of this invention, the dairy products are derived from the raw milk of cows, goats, sheep, horses, donkeys, camels, water buffalo, yaks, reindeer, moose, or humans.

In a particularly desirable embodiment, the dairy composition comprises a sweetener composition comprising steviol glycosides, including compounds 1, 2, 3, and/or 4, in combination with a dairy product. In a particular embodiment, steviol glycosides, including compounds 1, 2, 3, and/or 4, are present in the dairy composition in an total amount in the range of about 200 to about 20,000 weight percent of the dairy composition.

Tabletop sweetener compositions containing steviol glycosides, including compounds 1, 2, 3, and/or 4, are also contemplated herein. The tabletop composition can further include a variety of other ingredients, including but not limited to at least one bulking agent, additive, anti-caking agent, functional ingredient or combination thereof.

Suitable "bulking agents" include, but are not limited to, maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and the like, and mixtures thereof. Additionally, in accordance with still other embodiments of the invention, granulated sugar (sucrose) or other caloric sweeteners such as crystalline fructose, other carbohydrates, or sugar alcohol can be used as a bulking agent due to their provision of good content uniformity without the addition of significant calories.

The tabletop sweetener compositions can be packaged in any form known in the art. Non-limiting forms include, but are not limited to, powder form, granular form, packets, tablets, sachets, pellets, cubes, solids, and liquids. The amount of steviol glycosides, including compounds 1, 2, 3, and/or 4, in a dry-blend tabletop sweetener formulation can vary. In a particular embodiment, a dry-blend tabletop sweetener formulation may contain steviol glycosides in an amount from about 1% (w/w) to about 10% (w/w) of the tabletop sweetener composition.

A tabletop sweetener composition also may be embodied in the form of a liquid, wherein a sweetener composition comprising steviol glycosides, including compounds 1, 2, 3, and/or 4, is combined with a liquid carrier. Suitable non-limiting examples of carrier agents for liquid tabletop functional sweeteners include water, alcohol, polyol, glycerin base or citric acid base dissolved in water, and mixtures thereof.

In one embodiment, the sweetened composition is a beverage product comprising steviol glycosides, including compounds 1, 2, 3, and/or 4. As used herein a "beverage product" is a ready-to-drink beverage, a beverage concentrate, a beverage syrup, frozen beverage, or a powdered beverage. Suitable ready-to-drink beverages include carbonated and non-carbonated beverages. Carbonated beverages include, but are not limited to, enhanced sparkling beverages, cola, lemon-lime flavored sparkling beverage, orange flavored sparkling beverage, grape flavored sparkling beverage, strawberry flavored sparkling beverage, pineapple flavored sparkling beverage, ginger-ale, soft drinks and root beer. Non-carbonated beverages include, but are not limited to fruit juice, fruit-flavored juice, juice drinks, nectars, vegetable juice, vegetable-flavored juice, sports drinks, energy drinks, enhanced water drinks, enhanced water with vitamins, near water drinks (e.g., water with natural or synthetic flavorants), coconut water, tea type drinks (e.g. black tea, green tea, red tea, oolong tea), coffee, cocoa drink, beverage containing milk components (e.g. milk beverages, coffee containing milk components, cafe au lait, milk tea, fruit milk beverages), beverages containing cereal extracts, smoothies and combinations thereof.

Examples of frozen beverages, include, but are not limited to, icees, frozen cocktails, daiquiris, pina coladas, margaritas, milk shakes, frozen coffees, frozen lemonades, granitas, and slushees.

Beverage concentrates and beverage syrups can be prepared with an initial volume of liquid matrix (e.g. water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water.

In one embodiment, a beverage contains a sweetener composition comprising steviol glycosides, including compounds 1, 2, 3, and/or 4. Any sweetener composition comprising steviol glycosides, including compounds 1, 2, 3, and/or 4 detailed herein can be used in the beverages. In another embodiment, a method of preparing a beverage comprises combining a liquid matrix and steviol glycosides, including compounds 1, 2, 3, and/or 4. The method can further comprise addition of one or more sweeteners, additives and/or functional ingredients. In still another embodiment, a method of preparing a beverage comprises combining a liquid matrix and a sweetener composition comprising steviol glycosides, including compounds 1, 2, 3, and/or 4.

In another embodiment, a beverage contains a sweetener composition containing steviol glycosides, including compounds 1, 2, 3, and/or 4, wherein the steviol glycosides are present in the beverage in an amount ranging from about 1 ppm to about 10,000 ppm, such as, for example, from about 25 ppm to about 800 ppm. In another embodiment, steviol glycosides are present in the beverage in an amount ranging from about 100 ppm to about 600 ppm. In yet other embodiments, steviol glycosides are present in the beverage in an amount ranging from about 100 to about 200 ppm, from about 100 ppm to about 300 ppm, from about 100 ppm to about 400 ppm, or from about 100 ppm to about 500 ppm. In still another embodiment, steviol glycosides are present in the beverage in an amount ranging from about 300 to about 700 ppm, such as, for example, from about 400 ppm to about 600 ppm. In a particular embodiment, steviol glycosides are present in the beverage in an amount of about 500 ppm A method for imparting a more sugar-like temporal profile, flavor profile, or both to a sweetenable composition comprises combining a sweetenable composition with the sweetener compositions of the present invention, i.e., sweetener compositions containing steviol glycosides, including compounds 1, 2, 3, and/or 4.

The method can further include the addition of other sweeteners, additives, functional ingredients and combinations thereof. Any sweetener, additive or functional ingredient detailed herein can be used.

As used herein, the "sugar-like" characteristics include any characteristic similar to that of sucrose and include, but are not limited to, maximal response, flavor profile, temporal profile, adaptation behavior, mouthfeel, concentration/response function, tastant/and flavor/sweet taste interactions, spatial pattern selectivity, and temperature effects.

In certain embodiments, an agglomerate of steviol glycosides, including compounds 1, 2, 3, and/or 4, sweetener composition is provided. As used herein, "sweetener agglomerate" means a plurality of sweetener particles clustered and held together. Examples of sweetener agglomerates include, but are not limited to, binder held agglomerates, extrudates, and granules. Methods for making agglomerates are known to those of ordinary skill in the art, and are disclosed in more detail in U.S. Pat. No. 6,180,157. Generally described, the process for preparing an agglomerate in accordance with a certain embodiment comprises the steps of preparing a premix solution comprising steviol glycosides, including compounds 1, 2, 3, and/or 4, sweetener composition and a binding agent in a solvent, heating the premix to a temperature sufficient to effectively form a mixture of the premix, applying the premix onto a fluidized carrier by a fluid bed agglomerator, and drying the resulting agglomerate. The sweetness level of the resulting agglomerate may be modified by varying the amount of the sweetener composition in the premix solution.

In some embodiments provided are substantially dustless and substantially free-flowing extrudates or extruded agglomerates of steviol glycosides, including compounds 1, 2, 3, and/or 4, for a sweetener composition. Such particles may be formed with or without the use of binders using extrusion and spheronization processes.

"Extrudates" or "extruded sweetener composition", as used herein, refers to cylindrical, free-flowing, relatively non-dusty, mechanically strong granules of steviol glycosides, including compounds 1, 2, 3, and/or 4. The terms "spheres" or "spheronized sweetener composition", as used herein, refer to relatively spherical, smooth, free-flowing, relatively non-dusty, mechanically strong granules. A process for making extrudates are described in U.S. Pat. No. 6,365,216.

In another embodiment, granulated forms of steviol glycosides, including compounds 1, 2, 3, and/or 4. are provided. As used herein, the terms "granules," "granulated forms," and "granular forms" are synonymous and refer to free-flowing, substantially non-dusty, mechanically strong agglomerates of the steviol glycoside sweetener composition. Methods of granulation are known to those of ordinary skill in the art and are described in more detail in the PCT Publication WO 01/60842.

Example 1

Fermentation for Steviol Glycoside Production Including Compounds 1-4

Steviol glycoside compounds, including compounds 1-4, Reb D and Reb M, were produced by genetically engineered *Saccharomyces cerevisiae*. *Saccharomyces* strains EFSC 3261 and EFSC 3841 are described in International Application No. WO2014/122227.

Fed-batch fermentation was carried out aerobically in 2 L (working volume) fermenters which included a ~16 hour growth phase in the base medium (minimal medium containing glucose, ammonium sulfate, trace metals, vitamins, salts, and buffer) followed by ~100 hours of feeding with a glucose-containing defined feed medium. Glucose was utilized as the carbon and energy source and combined with trace metals, vitamins, and salts. The pH was kept near pH 5 and the temperature setpoint was 30° C. The feed rate was controlled to prevent oxygen depletion and to minimize ethanol formation (glucose-limited conditions). The fermentation minimal medium is based on Verduyn C, Postma E, Scheffers W A, Van Dijken J P. (1992). Yeast 8, 501-517.

Example 2

Purification of Compounds 1-4 and NMR Spectroscopy

Figure 3:
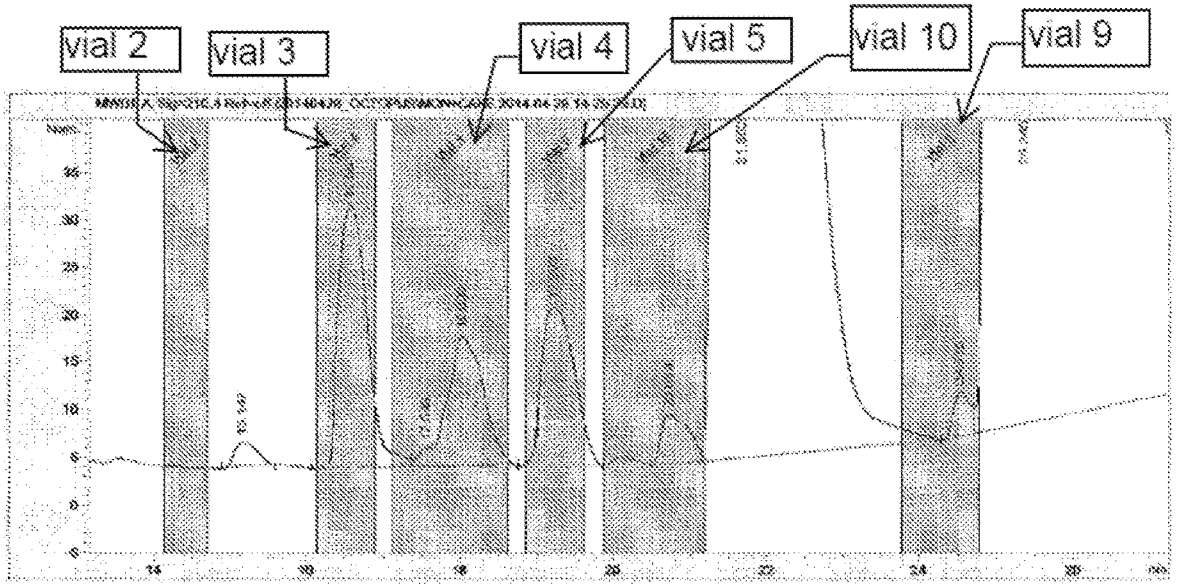
FIG. 3 is a purification chromatogram of compound 3 (OPS 1-4) and compound 4 (OPS 1-5). OPS 1-4 and OPS 1-5 purification chromatogram. Vial 10 contains OPS 1-4 and vial 9 contains OPS 1-5. Purified fractions of each compound from multiple injections were pooled together and dried under nitrogen at room temperature, producing the solid material. OPS 1-4 and OPS 1-5 were repurified by solubilizing in 50% ethanol and injecting on this method again to collect only the OPS 1-4 and OPS 1-5 compounds.
Figure 4A:
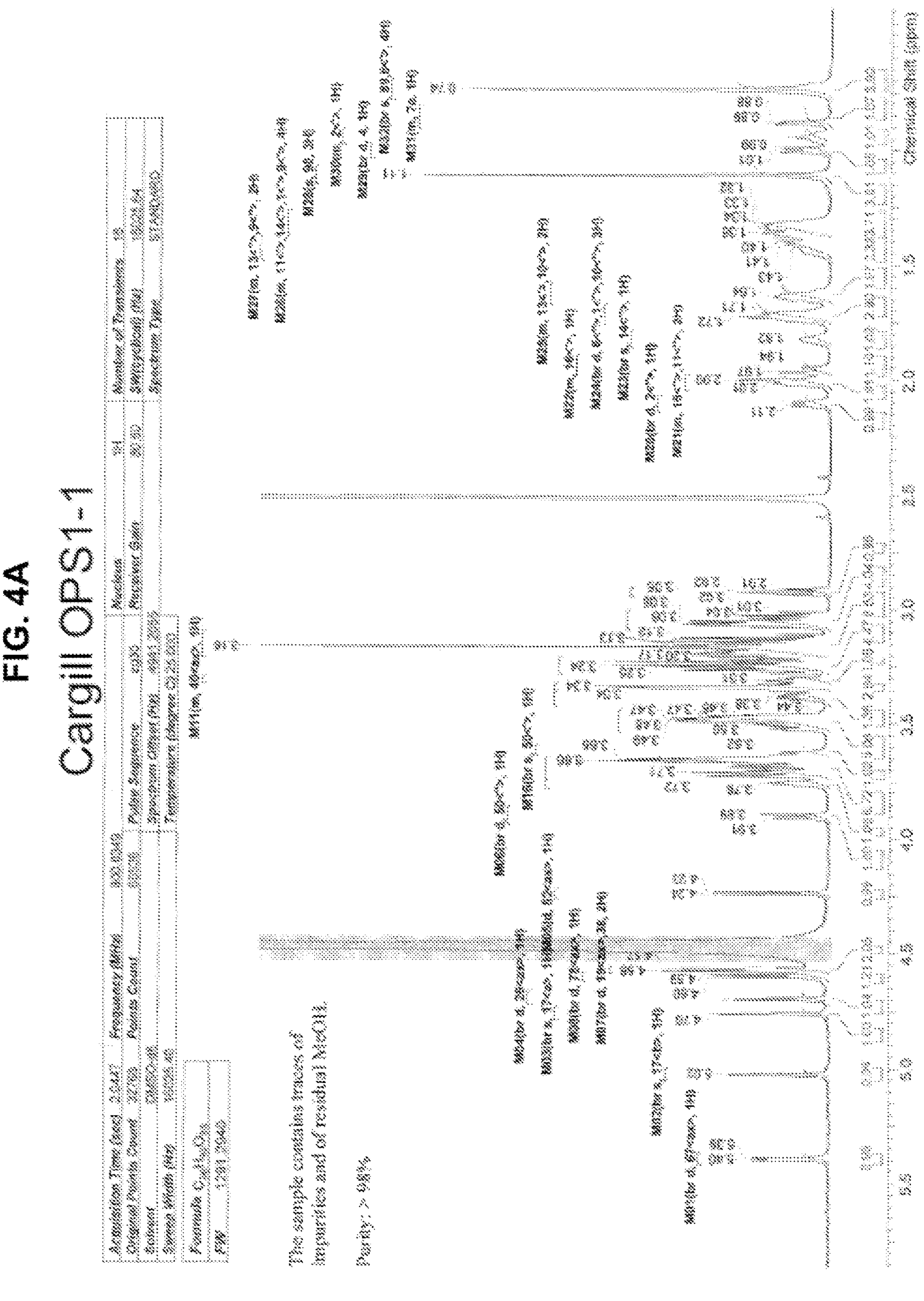
FIGS. 4A-4D constitute a graph showing the position and number of chemical shifts from NMR spectroscopy for compound 1 (OPS 1-1), $^{1}$H NMR (FIG. 4B: $^{1}$H NMR (800 MHz, DMSO-$d_6$) δ ppm 0.74 (br s, 4H) 0.81-0.91 (M, 1H) 1.00 br d, J=12.72 Hz, 1H) 1.11 (s, 3H) 1.27-1.38 (m, 4H) 1.38-1.49 (m, 2H) 1.53-1.67 (m, 2H) 1.72 (br d, J=12.23 Hz, 3H) 1.82 (br s, 1H) 1.89-1.98 (m, 1H) 1.98-2.04 (m, 2H) 2.10 (br d, J=11.49 Hz, 1H) 2.90-2.95 (m, 1H) 3.00-3.09 (M, 4H) 3.10-3.21 (M, 8H) 3.25 (br, dd, J=17.24 Hz, 4H) 3.3 3.32-(M 1H) 3.34 (br d, J=4.65 Hz, 3H) 3.36-3.43 (m, 1H) 3.44-3.54 (M, 5H) 3.62 (br s, 1H) 3.64-3.74 (M, 6 H) 3.75 (br d, J=8.56 Hz, 1H) 3.90 (br d, J=11.25 Hz, 1H) 4.24 (d, J=7.82 Hz, 1H) 4.57 (br d, J=7.83 Hz, 2H) 4.60 (br d, J=7.58 Hz, 1H) 4.76 (br s, 1H) 5.02 (br s, 1H) 5.39 (br, J=7.34 Hz, 1H) and $^{13}$C NMR (FIG. 4C: $^{13}$C NMR (201 MHz, DMSO-$d_6$) δ ppm 17.1, 19.9, 20.6, 22.7, 29.2, 37.7, 38.3, 40.3, 40.8, 42.1, 42.2, 44.4, 44.8, 47.4, 54.0, 57.4, 61.6, 61.9, 62.0, 62.1, 69.1, 69.3, 70.3, 70.8, 70.8, 71.3, 71.5, 74.2, 74.4, 75.1, 75.4, 75.6, 76.9, 76.9, 77.2, 77.2, 77.2, 77.2, 77.2, 77.2, 77.6, 77.8, 78.4, 79.6, 86.5, 88.4, 93.6, 96.4, 103.0, 103.3, 103.9, 105.8, 153.2, 178.0) spectroscopy data and atom numbering for compound 1, and chemical assignments for compound 1 made based on COSY, TOCSY, HSQC-DEPT, and HMBC correlations.
Figure 4B:
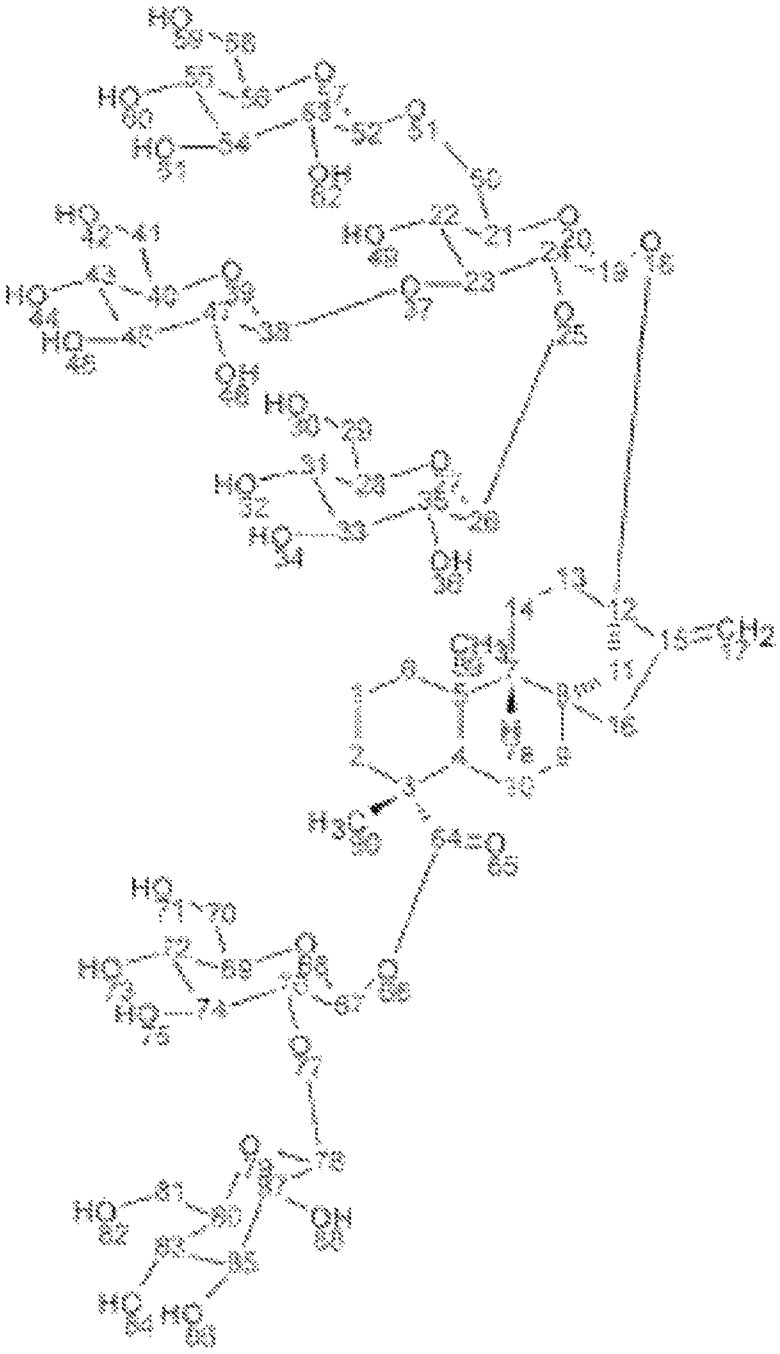
Figure 4C:
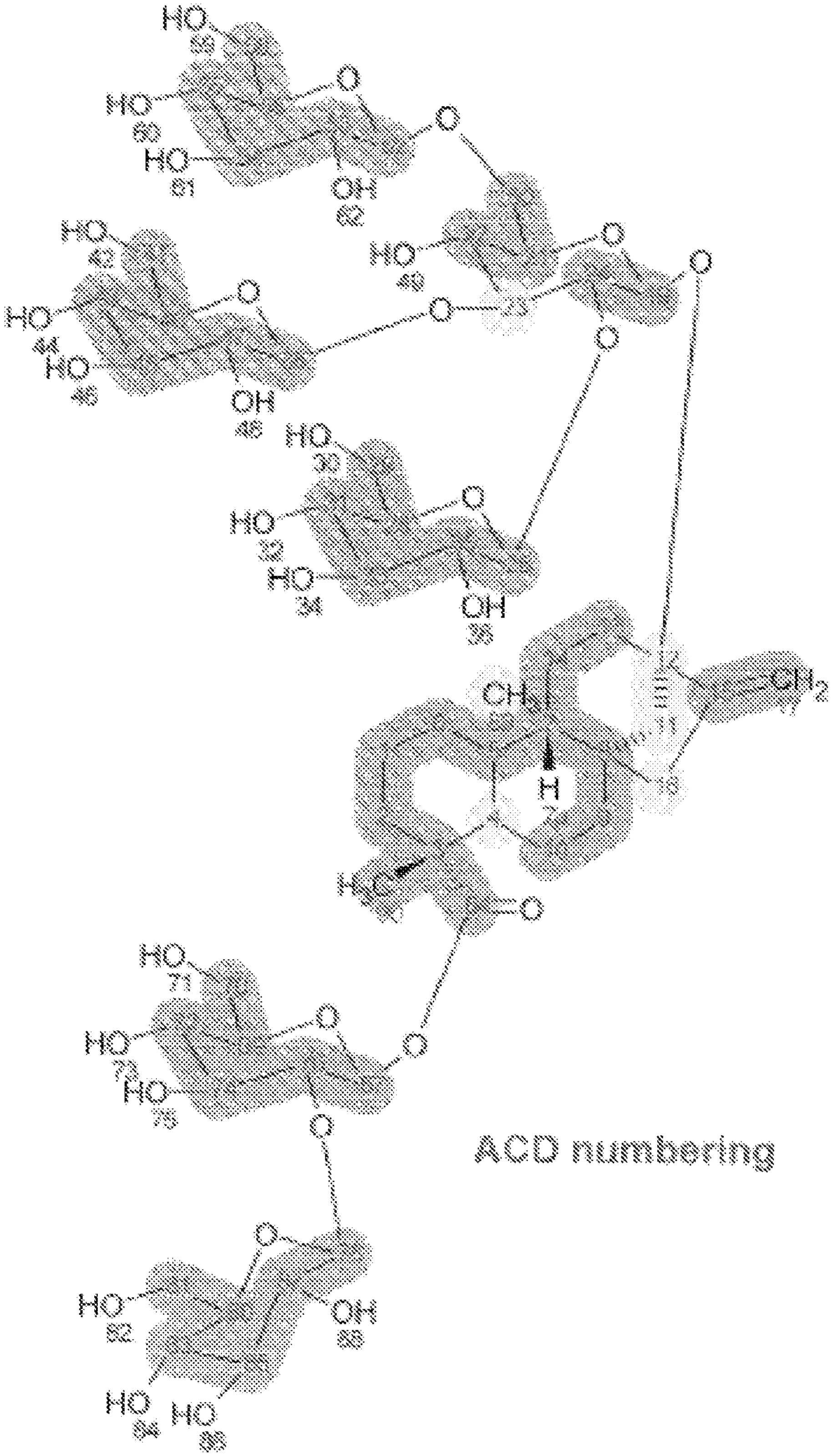
Figure 4D:
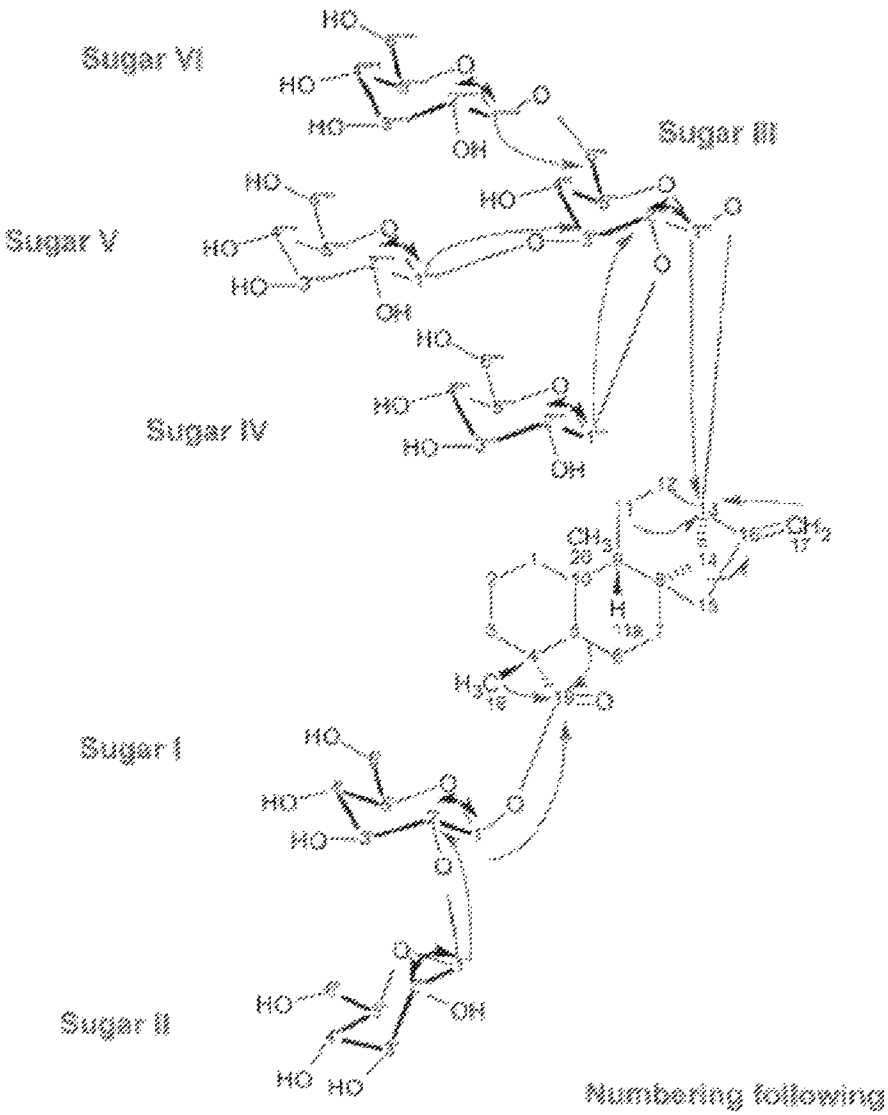
Figure 5A:
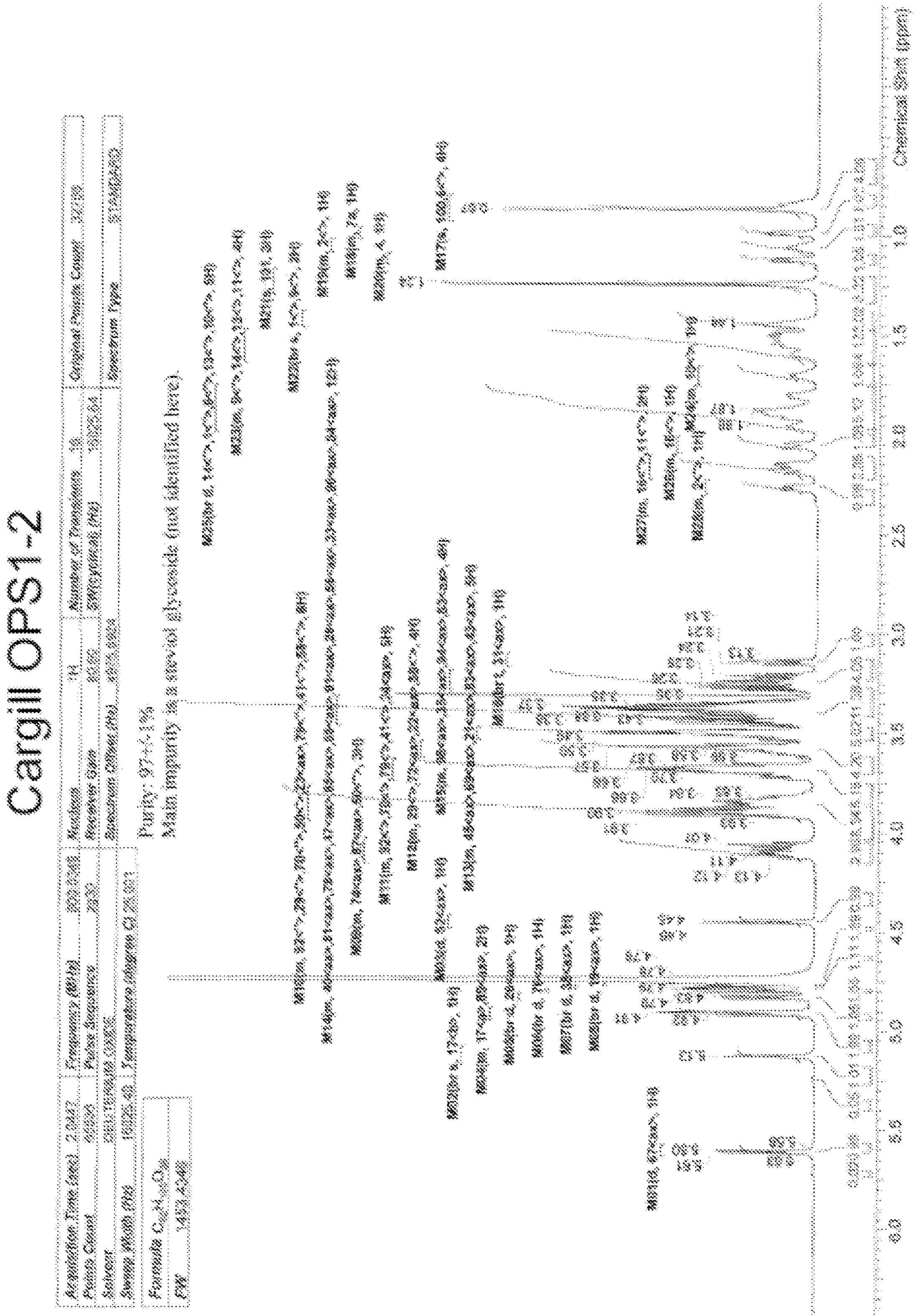
Figure 5B:
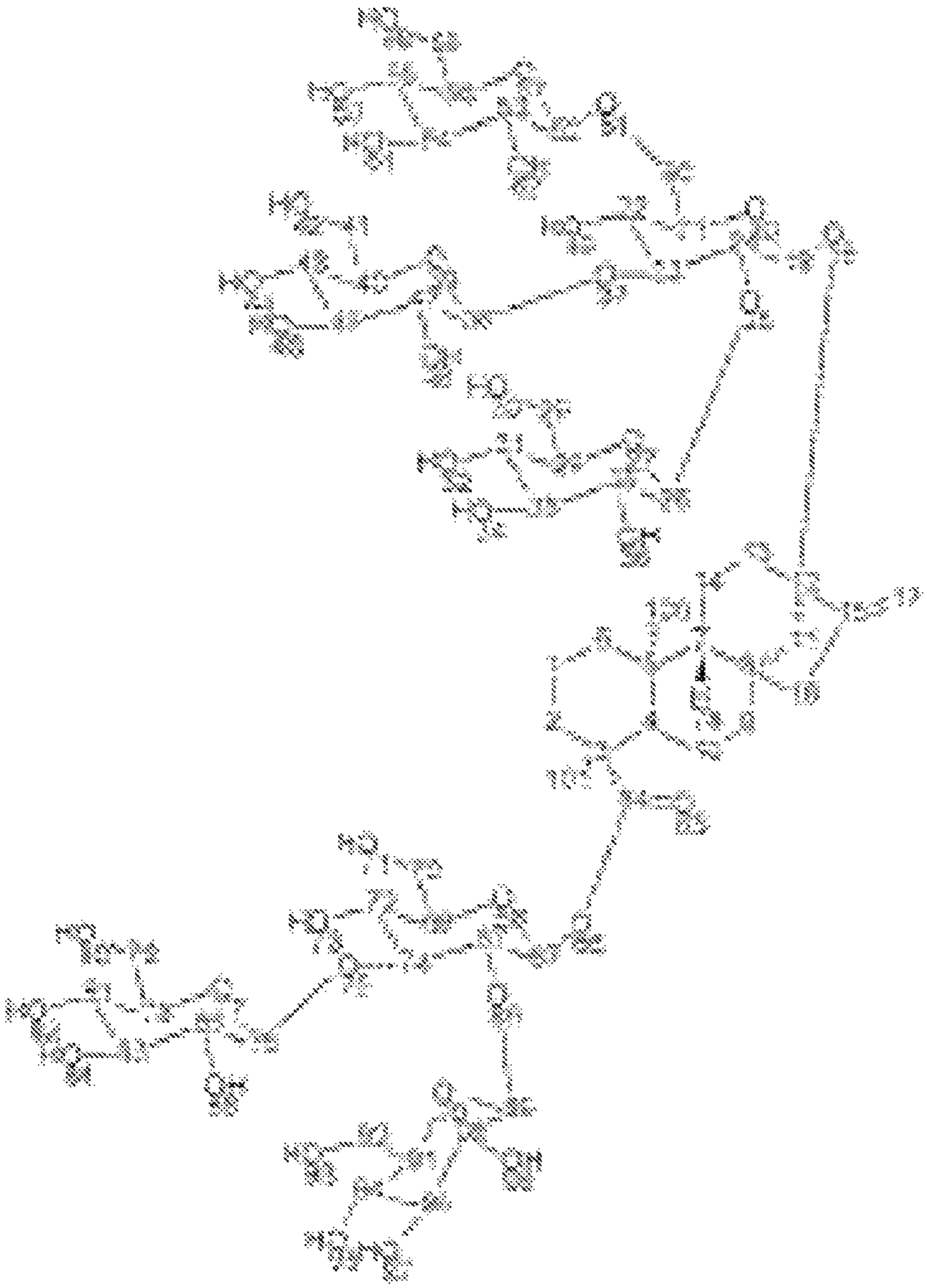
Figure 5C:
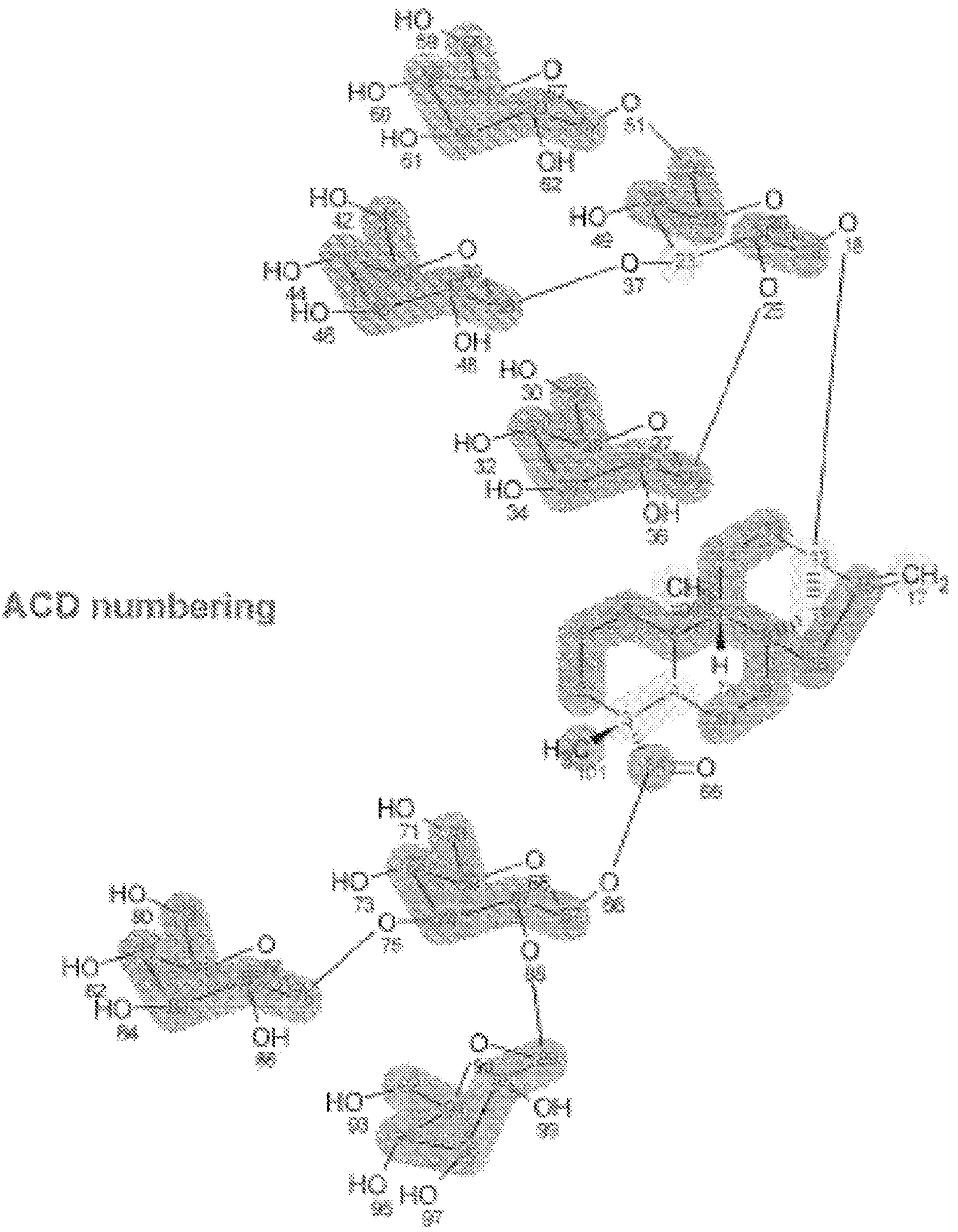
Figure 6A:
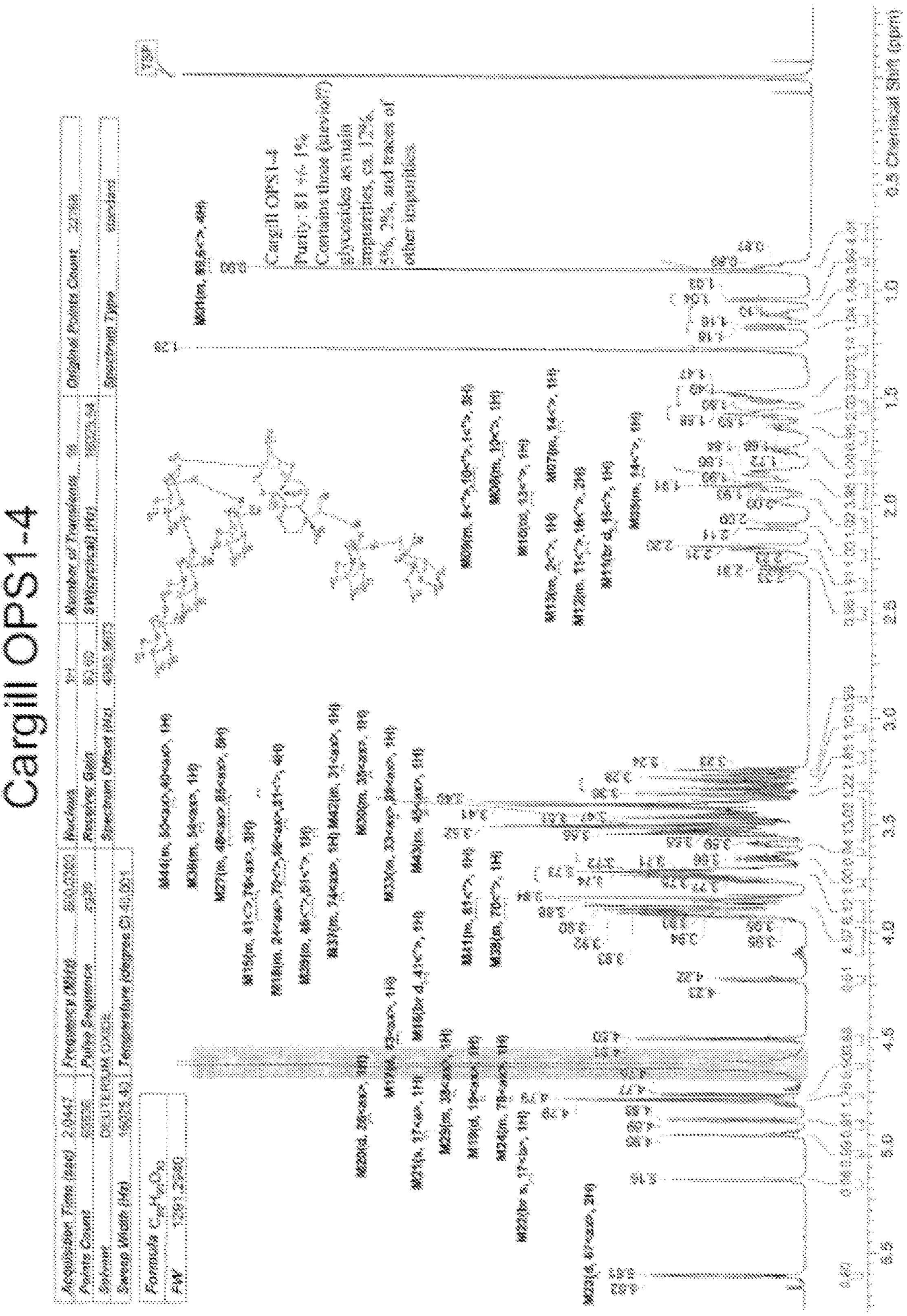
Figure 6C:
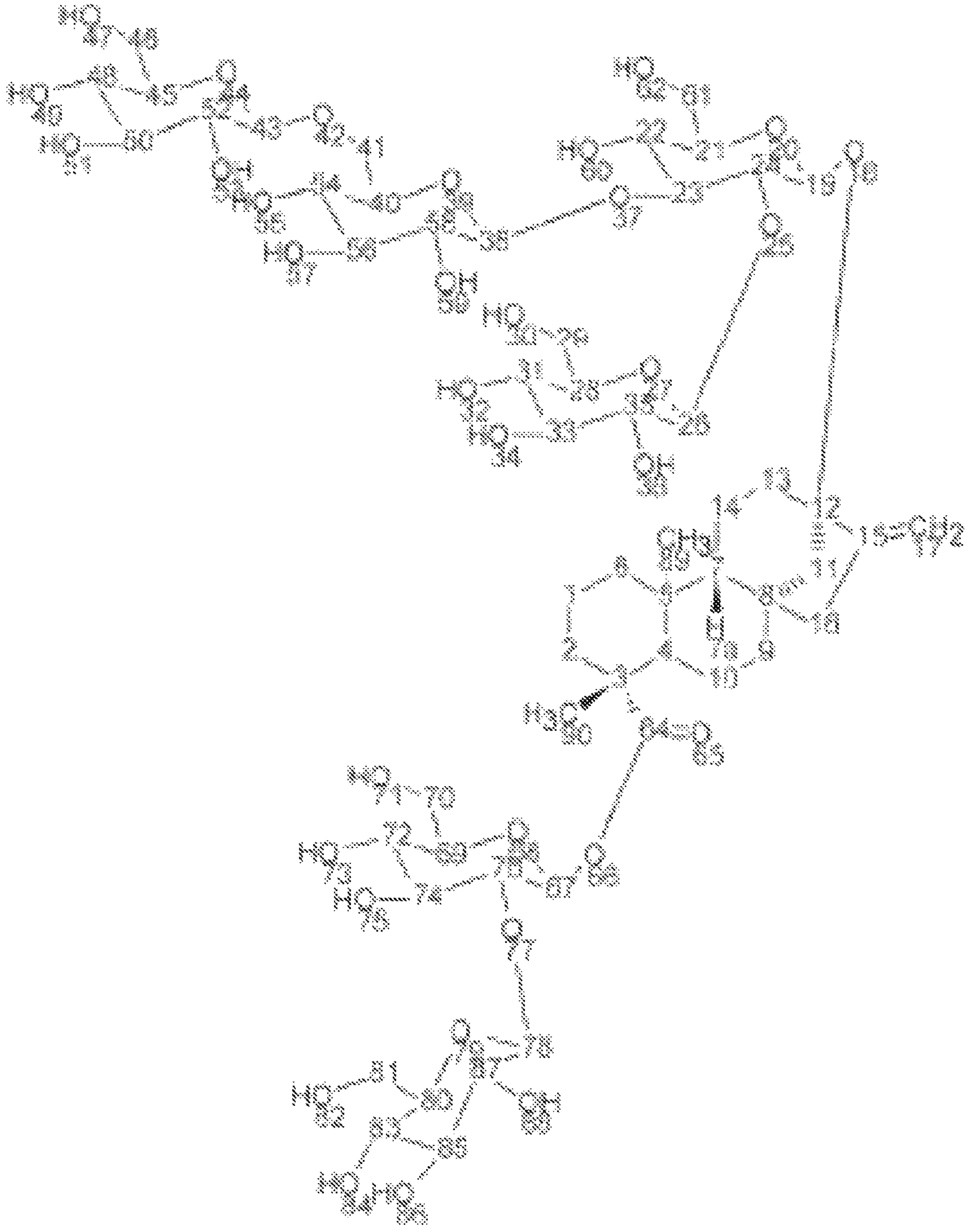
Figure 6D:
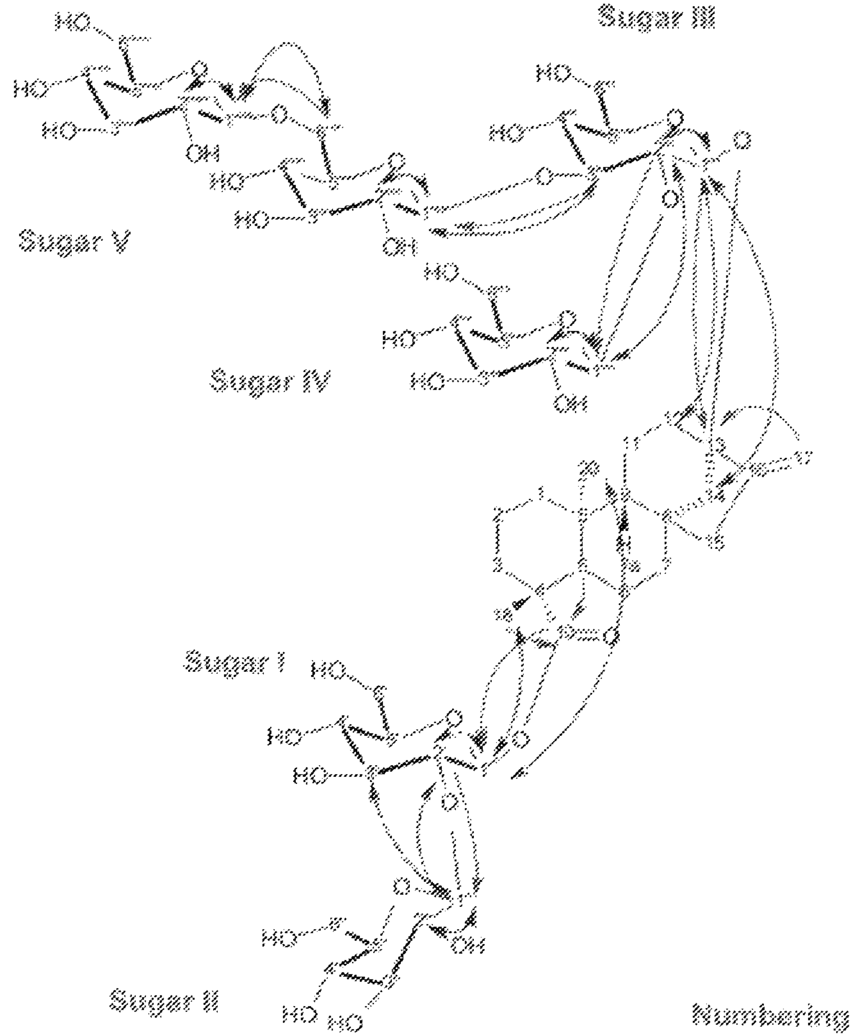
Figure 7A:
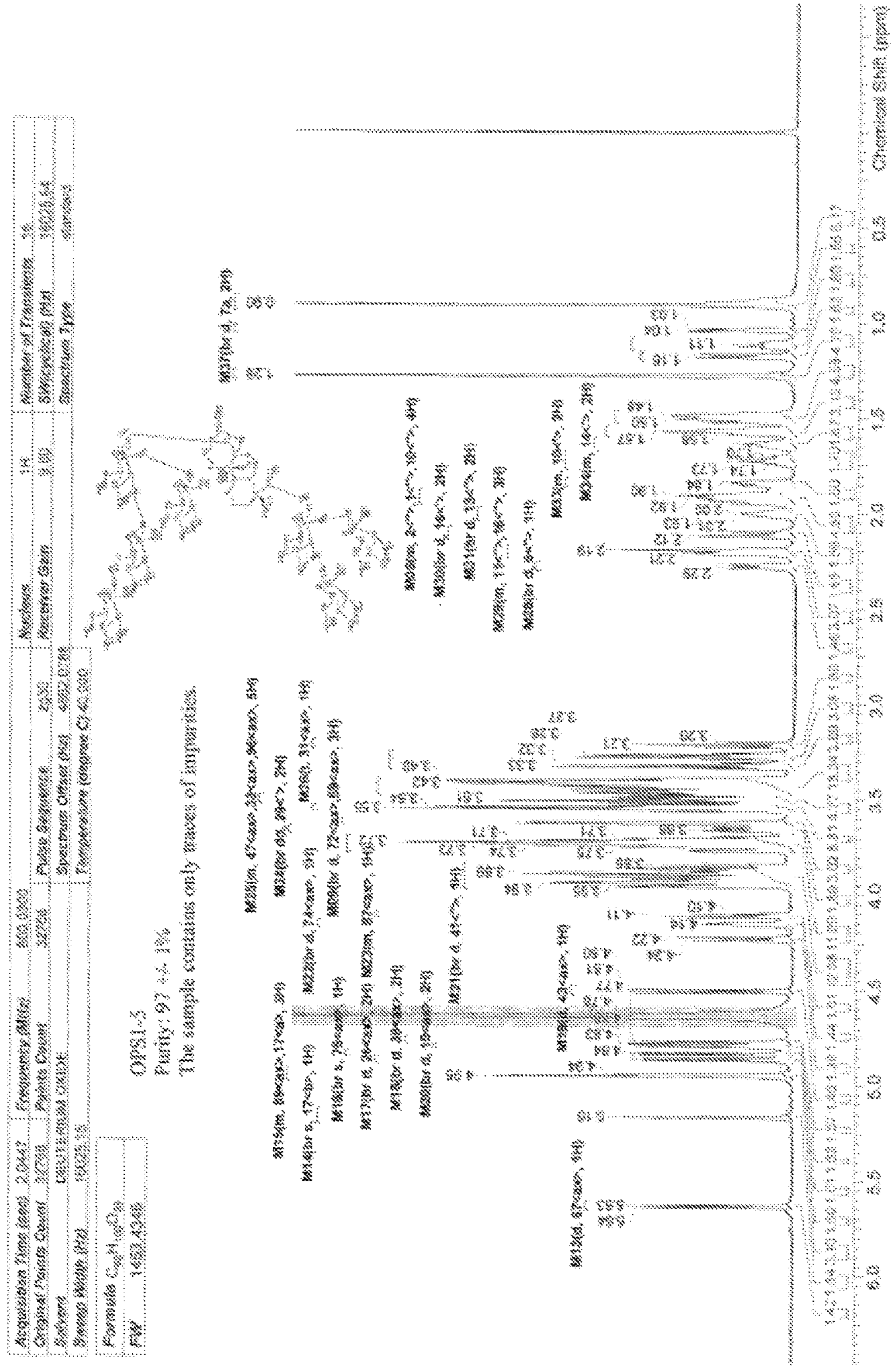
FIGS. 7A-7D constitute a graph showing the position and number of chemical shifts from NMR spectroscopy for compound 4 (OPS 1-5), $^{1}$H NMR (FIG. 7B: $^{1}$H NMR (800 MHz, DEUTERIUM OXIDE) δ ppm 0.90 (s, 6H) 1.04 (br d, J=7.83 Hz, 2H) 1.08-1.14 (m, 2H) 1.17 (br d, J=12.23 Hz, 2H) 1.28 (s, 5H) 1.46-1.53 (m, 5H) 1.54-1.60 (m, 3H) 1.60-1.67 (m, 2H) 1.67-1.77 (m, 2H) 1.84 (br d, J=9.29 Hz, 2H) 1.87-1.96 (m, 4H) 2.00 (br d, J=6.36 Hz, 2H) 2.11 (br d, J=16.14 Hz, 2H) 2.17-2.23 (m, 3H) 2.28 (br d, J=12.72 Hz, 1H) 3.21 (t, J=9.29 Hz, 1H) 3.27 (q, J=8.31 Hz, 3H) 3.30-3.35 (m, 3H) 3.39-3.48 (m, 13H) 3.48-3.53 (m, 5H) 3.53-3.56 (m, 6H) 3.62 (br d, J=4.40 Hz, 3H) 3.66 (br dd, J=12.23, 7.34 Hz, 2H) 3.69-3.78 (m, 11H) 3.83-3.97 (m, 13H) 4.09-4.13 (m, 1H) 4.15 (br d, J=3.91 Hz, 1H) 4.23 (br d, J=10.76 Hz, 1H) 4.50 (d, J=7.83 Hz, 1H) 4.77 (br d, J=7.83 Hz, 2H) 4.79 (br d, J=8.31 Hz, 2H) 4.81 (br s, 1H) 4.86 (br d, J=7.82 Hz, 2H) 4.90-4.98 (m, 3H) 5.16 (br s, 1H) 5.63 (d, J=7.34 Hz, 1H) and $^{13}$C NMR (FIG. 7C: $^{13}$C NMR (201 MHz, DEUTERIUM OXIDE) δ ppm 18.8, 21.7, 22.7, 24.5, 31.0, 39.7, 39.9, 41.9, 42.7, 43.9, 44.1, 46.7, 46.8, 49.4, 55.9, 59.5, 63.5, 63.6, 63.6, 63.7, 64.5, 64.5, 71.0, 71.5, 71.6, 72.4, 72.5, 72.5, 73.4, 73.4, 76.0, 76.3, 76.8, 77.0, 77.6, 78.0, 78.6, 78.6, 78.8, 78.8, 78.8, 78.8, 78.8, 79.1, 79.1, 79.1, 81.4, 87.5, 89.2, 90.7, 95.6, 98.3, 104.5, 104.9, 105.0, 105.2, 105.4, 107.1, 155.7, 181.2) spectroscopy data and atom numbering for compound 4, and chemical assignments for compound 4 made based on COSY, TOCSY, HSQC-DEPT, and HMBC correlations. The chemical structure shown in FIG. 7A is the same as that shown in FIGS. 7B and 7C, where it is more legible.
Figure 7B:
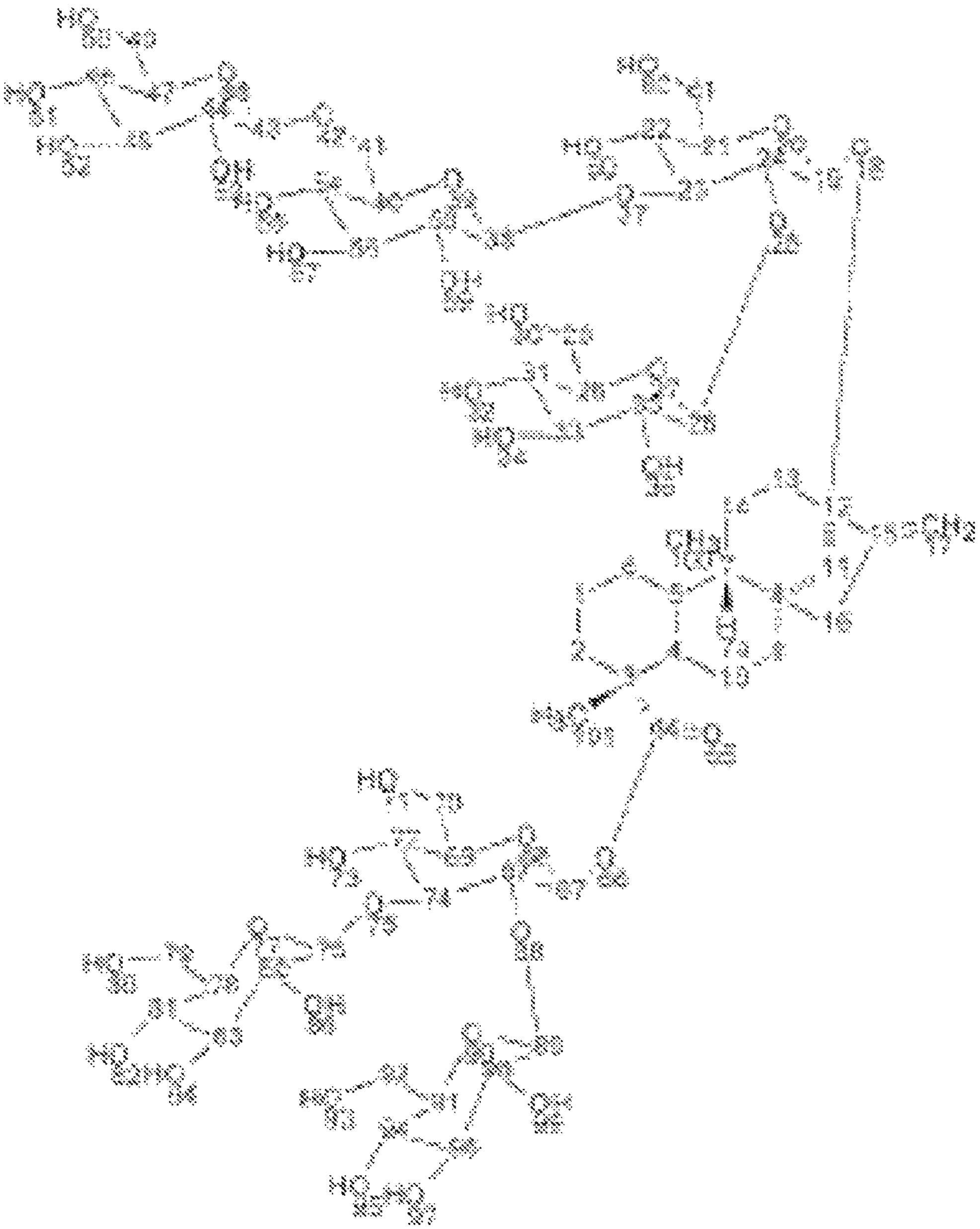
Figure 7C:
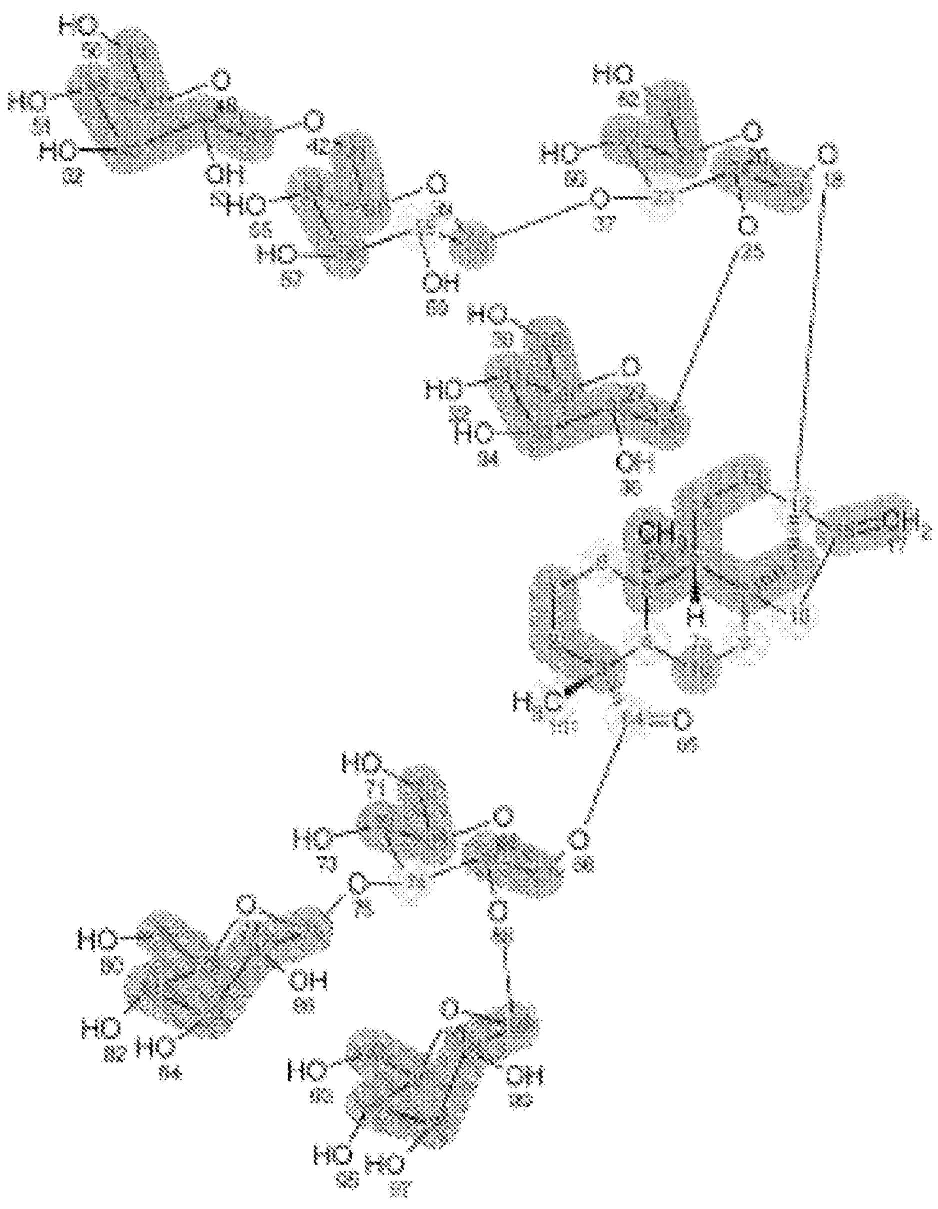
Figure 7D:
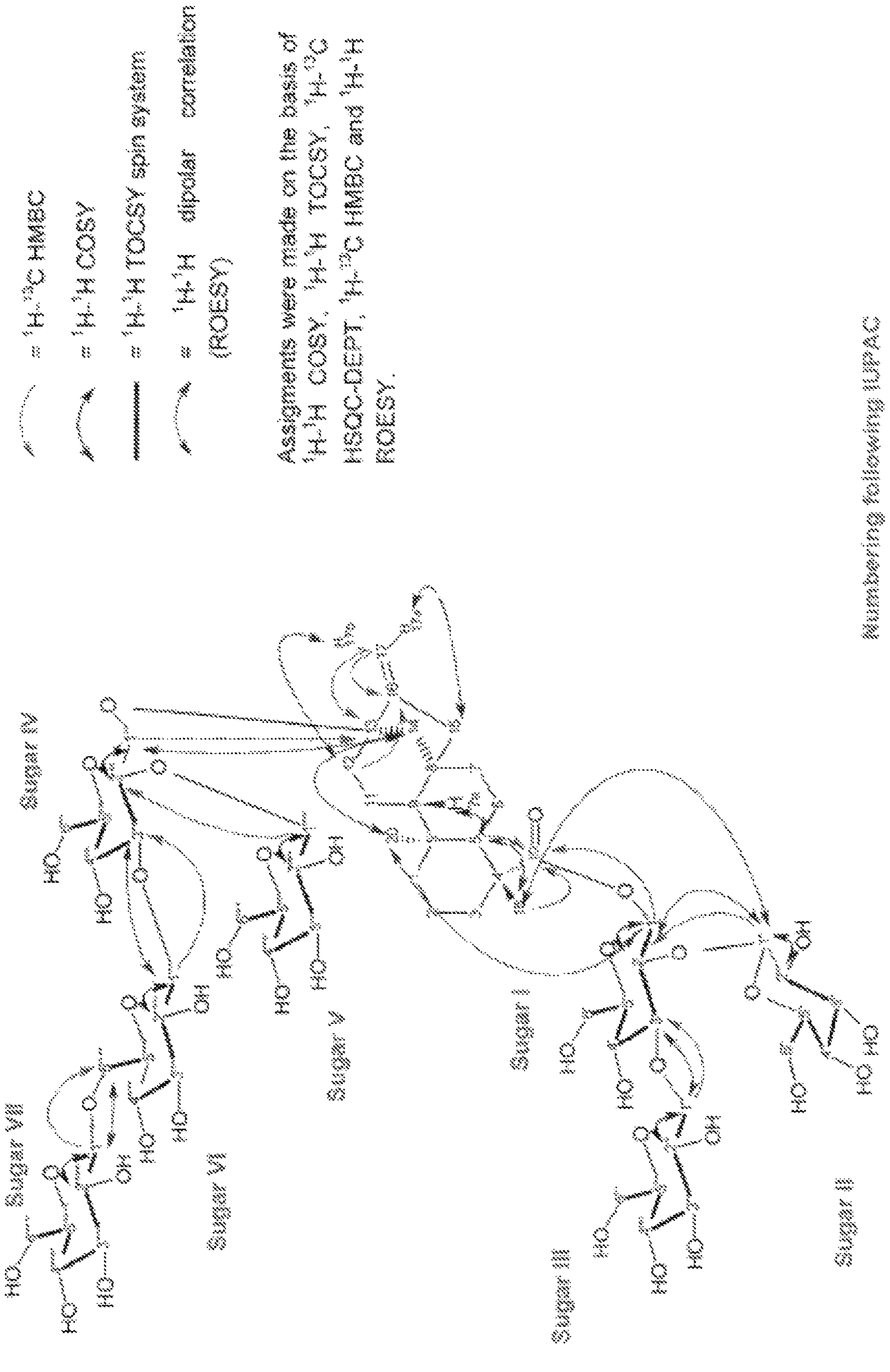

Compounds 1-4 (designated in the purification chromatogram as shown in FIGS. 2 and 3 as OPS1-1, OPS1-2, OPS1-4, and OPS1-5) were purified with preparative liquid chromatography as follows. Dried fermentation broth enriched in these compounds was used as the starting material for purification. The material was dissolved in 50:50 ethanol:water by sonication at 50° C. 5 mL of the solution was filtered through a 0.2 μm nylon syringe tip filter into a 5 mL autosampler vial for injection onto an Agilent 1260 preparative LC.

Compound 1 (OPS1-1) and Compound 2 (OPS1-2) fractions were purified as follows: 2.5 mL of sample was injected on the Phenomenex Kinetex XB-C18 5 μm, 21.2×250 mm column. A mixture of methanol and water (40:60 v/v) was used as a solvent. The flow rate was set at 20 mL/min, with a maximum pressure of 400 bar. FIG. 2: OPS 1-1 and OPS 1-2 purification chromatogram. Vial 2 is compound 1 (OPS1-1) and vial 4 is compound 2 (OPS1-2). Purified fractions of each compound from multiple injections were pooled together and dried under nitrogen at room temperature, producing the solid material that was characterized by NMR.

Compound 3 (OPS1-4) and Compound 4 (OPS1-5) fractions were purified as follows: 2.5 mL of sample was injected on the Phenomenex Kinetex XB-C18 5 μm, 21.2×250 mm column. A mixture of methanol and water (40:60 v/v) was used as a solvent. The flow rate was set at 20 mL/min, with a maximum pressure of 400 bar. FIG. 3: OPS 1-4 and OPS 1-5 purification chromatogram. Vial 2 is compound 1 (OPS 1-1) and vial 4 is compound 2 (OPS 1-2). Vial 10 contains OPS 1-4 and vial 9 contains OPS 1-5.

Purified fractions of each compound from multiple injections were pooled together and dried under nitrogen at room temperature, producing the solid material. OPS 1-4 and OPS 1-5 were repurified by solubilizing in 50% ethanol and injecting on this method again to collect only the OPS 1-4 and OPS 1-5 compounds. Purified fractions of each compound from multiple injections were pooled together and dried under nitrogen at room temperature, producing the solid material that was characterized by NMR.

All NMR spectra were acquired on a 800 MHz Bruker Avance machine (800 MHz for 1H, 201 MHz for 13C) equipped with a cryogenic probe (5 mm CPTCI 1H-13C/15N/D Z-GRD Z44909/0010). OPS1-1 was dissolved in 550 ul DMSO-d6/D2O 1:1 and run in 5 mm tubes. OPS 1-2 was dissolved in 60 ul D2O and measured in a 1.7 mm tube. OPS 1-4 & 5 were dissolved in 200 ul D2O (TSP as standard for chemical shift referencing) and measured in 3 mm tubes. OPS 1-1 & 2 were measured at 25 C, OPS 1-4 & 5 at 40 C.

Structures were solved by means of standard homo- and heteronuclear multipulse NMR experiments, namely $^{1}H$,$^{1}H$-COSY, $^{1}H$,$^{1}H$-ROESY, $^{1}H$,$^{13}C$-HSQC and $^{1}H$,$^{13}C$-HMBC.

FIGS. 4A-7D constitute graphs showing the position and number of chemical shifts from NMR spectroscopy, $^{1}H$ NMR and $^{13}C$ NMR spectroscopy data and atom numbering, and chemical assignments based on COSY, TOCSY, HSQC-DEPT, and HMBC correlations for compounds 1-4 (OPS 1-1, OPS 1-2, OPS 1-4, and OPS 1-5).

Example 3

Steviol Glycoside Composition of Fermentation Media

The fermentation media prepared from Example 1 was analyzed to determine the types and amounts of steviol glycoside compounds, including compounds 1-4.

TABLE 1

| Profile of 140501-B1 | |
|---|---|
| Compound 1 | 3.73 |
| Compound 2 | 0.51 |
| Compound 3 | 0.64 |
| Reb D | 37.83 |

TABLE 1-continued

| Profile of 140501-B1 | |
|---|---|
| Compound 4 | 0.19 |
| Reb M | 57.58 |
| Total Steviol Glycosides | 99.9% |

Example 4

Enhancement of Steviol Glycoside Solubility by Compounds 1-4

The presence of compounds 1-4, even at low concentrations, showed a significant effect on the solubility of rebD and rebM in a composition. The instantaneous and equilibrium solubility was studied for pure rebD, rebM, a blend of pure rebD/rebM, and compared to the solubility of rebD and rebM from the fermentation composition containing these isomers Instantaneous solubility is determined by mixing steviol glycoisde with deionized water vigorously for 10 minutes at room temperature. Equilibrium solubility is determined by heating deionized water with steviol glycoside at 80° C. for 15 minutes and cooling down to room temperature for observation up to 4 days. Clear solutions without precipitates are considered soluble. The results are shown below.

RebD has a very low instantaneous solubility (<0.08% at room temperature). Upon heating to 80° C. for 15 minutes, rebD stayed soluble at 0.08% for at least 4 days at room temperature. Table 2 reflects the instantaneous and equilibrium solubility of RebD.

TABLE 2

| RebD | 0.08% | 0.10% | 0.15% | 0.20% |
|---|---|---|---|---|
| instantaneous | | | | |
| equilibrium | soluble | | | |

RebM has a higher solubility than rebD. Its instantaneous solubility is at least 0.13% and with heating, the equilibrium solubility of rebM is at least 0.2% at room temperature. Table 3 reflects the instantaneous and equilibrium solubility of RebD.

TABLE 3

| RebM | 0.10% | 0.13% | 0.20% | 0.30% |
|---|---|---|---|---|
| instantaneous | soluble | soluble | | |
| equilibrium | soluble | soluble | soluble | |

To assess if rebM would enhance the solubility of rebD, a mixture of rebD and rebM at different ratios were used. No improvement in instantaneous solubility was seen by blending rebD and with rebM and no obvious increase in equilibrium solubility was seen either. Table 4 reflects the instantaneous and equilibrium solubility of the RebD and RebM mixture.

TABLE 4

| D/M | 0.08% D/0.12% M | 0.08% D/0.17% M | 0.11% D/0.24% M |
|---|---|---|---|
| instantaneous | | | |
| equilibrium | soluble | soluble | |

Surprisingly, fermentation derived steviol glycoside composition from Example 1, which includes compounds 1-4, was found to have a significantly improved solubility over pure rebD and rebM mixtures. At least 0.37% of fermentation steviol glycoside is soluble instantaneously in room temperature water, which contains 0.14% rebD and 0.21% rebM. Therefore a 75% improvement in solubility over pure rebD was shown in the presence of compounds 1-4. Table 5 reflects the instantaneous and equilibrium solubility fermentation derived steviol glycoside composition which includes RebD, RebM, and compounds 1-4.

TABLE 5

| Lot 140501-B1 | 0.14% D/0.21% M | 0.20% D/0.30% M |
|---|---|---|
| instantaneous | soluble | |
| equilibrium | soluble | |

The invention claimed is:

1. An aqueous composition, comprising a first and a second steviol glycosides, wherein the first steviol glycoside is compound 1, compound 2, compound 3, or compound 4 according to the following structures:

(compound 1)

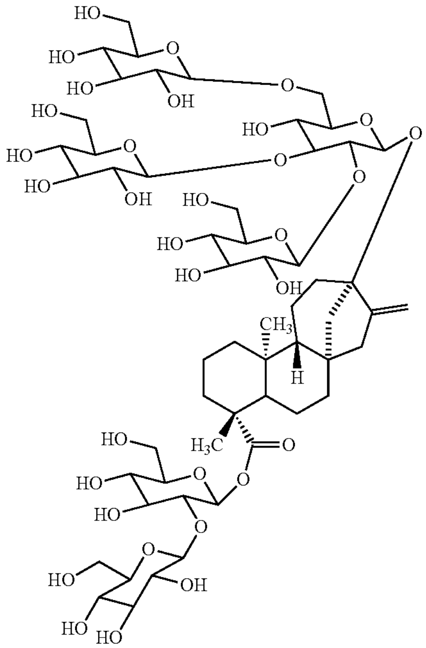

-continued (compound 3)

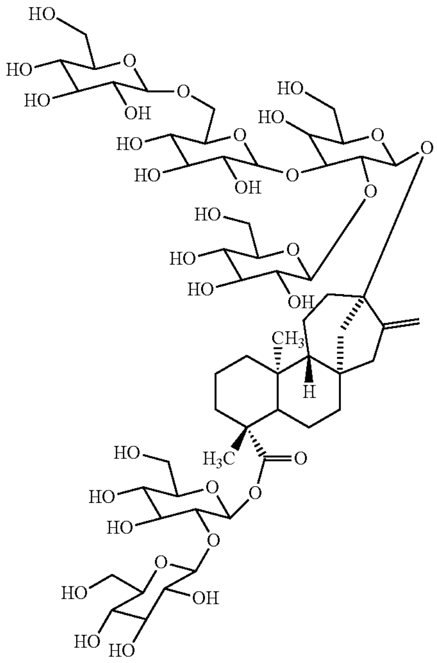

(compound 2)

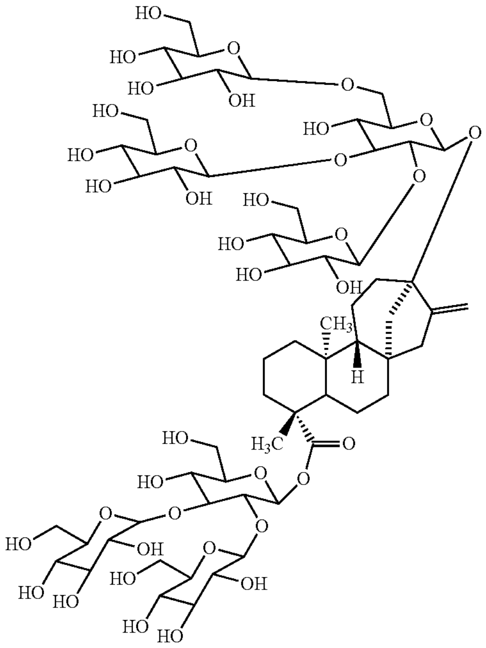

-continued (compound 4)

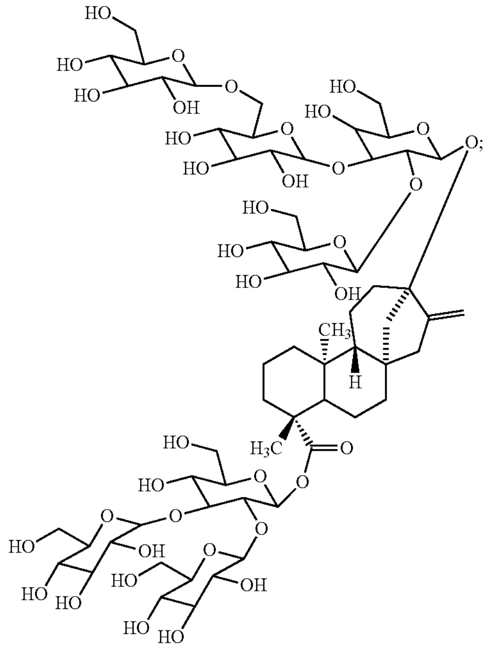

wherein the second steviol glycoside is different from the first steviol glycoside; and wherein the presence of the first steviol glycoside improves the solubility of the second steviol glycoside in the composition by 5% or greater.

2. The aqueous composition of claim 1, wherein the presence of the first steviol glycoside improves the solubility of the second steviol glycoside in the composition by 20% or greater.

3. The aqueous composition of claim 1, wherein the second steviol glycoside is rebaudioside A, rebaudioside B, rebaudioside M, rebaudioside D, rebaudioside I, rebaudioside Q, rebaudioside N, or stevioside.

4. The aqueous composition of claim 1, wherein the second steviol glycoside comprises rebaudioside D and/or rebaudioside M.

5. The aqueous composition of claim 1, wherein the solubility is an instantaneous solubility.

6. The aqueous composition of claim 1, wherein the solubility is an equilibrium solubility.

7. The aqueous composition of claim 1, wherein the first steviol glycoside is present in the composition in an amount of less than 6% of the total amount of steviol glycosides in the composition.

8. The aqueous composition of claim 1, wherein the first steviol glycoside is present in the composition in an amount from about 0.5% to about 6% of the total amount of steviol glycosides in the composition.

9. The aqueous composition of claim 1, wherein the first steviol glycoside is present in the composition in an amount of greater than 6% of the total amount of steviol glycosides in the composition.

10. The aqueous composition of claim 1, wherein the composition is a fermentation broth.

11. The aqueous composition of claim 1, wherein the composition is a beverage, a beverage concentrate, or a sweetener.

12. A method of enhancing the solubility of a steviol glycoside in an aqueous composition, comprising a step of providing an aqueous composition comprising a first and a second steviol glycosides, wherein the first steviol glycoside is compound 1, compound 2, compound 3, or compound 4 according to the following structures:

(compound 1)

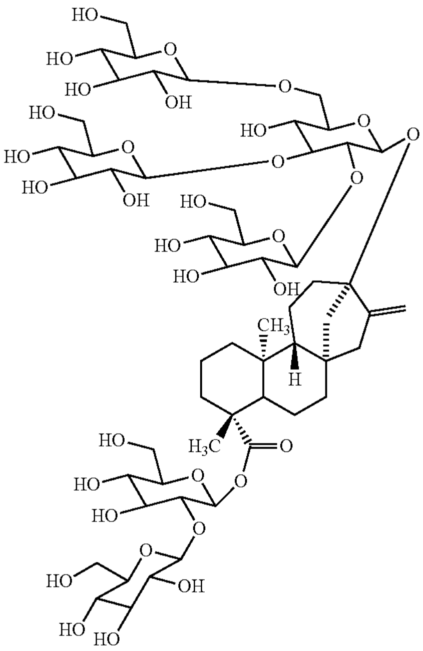

(compound 3)

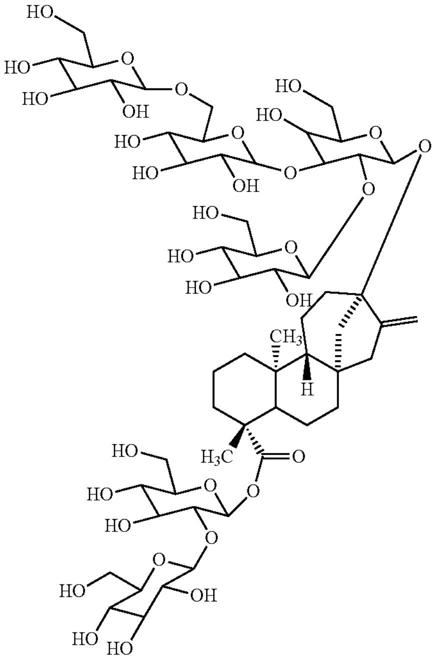

-continued (compound 2)

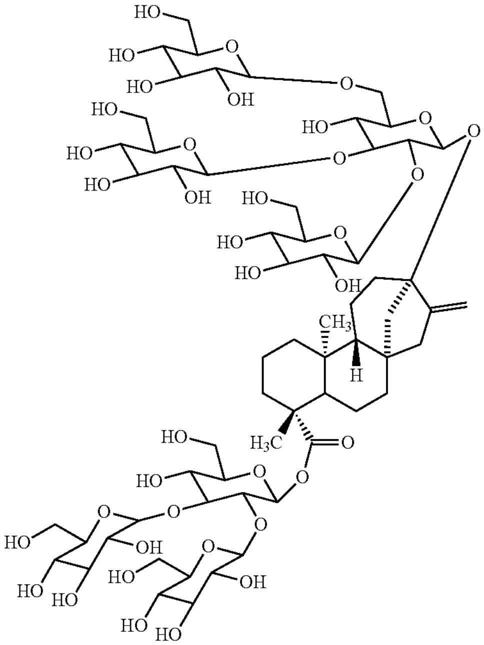

(compound 4)

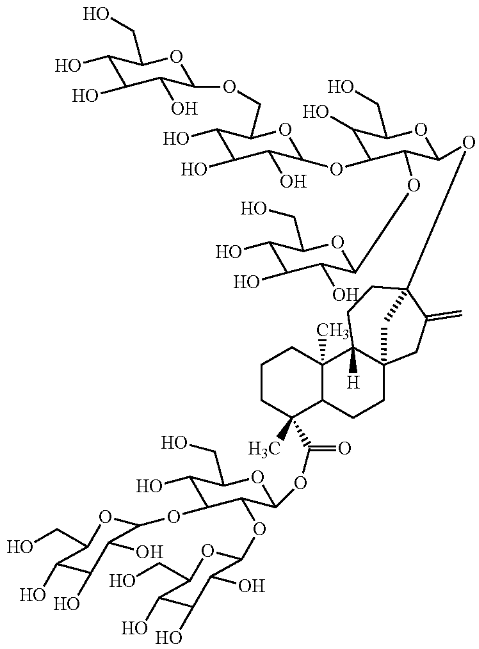

wherein the second steviol glycoside is different than the first steviol glycoside, and wherein the second steviol glycoside has a solubility in an aqueous composition that lacks the first steviol glycoside that is lower than a solubility of the second steviol glycoside in an aqueous composition that includes the first steviol glycoside.

13. The method of claim 12, wherein the second steviol glycoside is rebaudioside A, rebaudioside B, rebaudioside M, rebaudioside D, rebaudioside I, rebaudioside Q, rebaudioside N, or stevioside.

* * * * *

UNITED STATES PATENT AND TRADEMARK OFFICE

CERTIFICATE OF CORRECTION

PATENT NO. : 12,030,905 B2
APPLICATION NO. : 17/856460
DATED : July 9, 2024
INVENTOR(S) : Ting Liu Carlson and Dan Gaspard It is certified that error appears in the above-identified patent and that said Letters Patent is hereby corrected as shown below:

In the Specification

Column 5, Line 4 should read --directed to providing-- instead of "directed of providing".

Column 11, Line 59 should read --19-O-1,2-diglycosylated-- instead of "19-0-1,2-diglycosylated".

Column 12, Line 9 should read --dihydrogen phosphate-- instead of "dihydrogenphosphate".

Column 13, Line 28 should read --micron or sub-micron filter-- instead of "micron or sub-micron".

Column 14, Line 18 should read --0.1% to about 0.25%-- instead of "0.25% to about 0.1%"; Line 51 should read --1, 2, 3, or 4 can optionally-- instead of "1, 2, 3, or 4. can optionally".

Column 15, Line 1 should read --the composition can include-- instead of "composition can include"; Line 4 should read --total amount of steviol glycosides-- instead of "total amount steviol glycosides"; Line 27 should read --solubility of 0.08%-- instead of "solubility 0.08%"; Line 33 should read --addition of compounds 1-4 significantly improves-- instead of "addition of compounds 1-4, significantly improves"; Line 38 should read --the composition may-- instead of "composition may"; Line 40 should read --glycosides other than-- instead of "glycoside other than".

Column 16, Line 33 should read --greater than about 90%, or greater than about 95% relative to-- instead of "greater than about 90%, greater than about 95%, relative to"; Line 61 should read --system). Alternatively,-- instead of "system) Alternatively,".

Column 18, Line 65 should read --a total steviol glycoside-- instead of "total steviol glycoside".

Column 22, Line 16 should read --additives include chitosan-- instead of "additives include, chitosan"; Line 20 should read --poly-L-α-lysine or poly-L-ε-lysine-- instead of "poly-L-a-lysine or poly-L-e-lysine"; Line 21 should read --poly-L-α-ornithine or poly-L-ε-ornithine-- instead of Signed and Sealed this
Eleventh Day of February, 2025

Coke Morgan Stewart
*Acting Director of the United States Patent and Trademark Office*

"poly-L-a-ornithine or poly-L-e-ornithine"; Line 54 should read --carbamoylcholine chloride-- instead of "carbamoyl, choline chloride".

Column 23, Line 52 should read --α-carotene-- instead of "a-carotene"; Line 53 should read --resveratrol-- instead of "reservatol"; Line 56 should read --glutamine-- instead of "gutamine"; Line 61 should read --kaempferol-- instead of "kaempfedrol"; Line 63 should read --eriodictyol-- instead of "erodictyol"; Line 65 should read --epigallocatechin and its gallate forms (ECGC), theaflavin-- instead of "epigallocatechin and its gallate forms (ECGC) theaflavin"; Line 67 should read --anthocyanins-- instead of "anythocyanins".

Column 24, Line 1 should read --cyanidine-- instead of "cyaniding"; Line 7 should read --(R)-α-lipoic acid-- instead of "R-a-lipoic acid"; Line 9 should read --rooibos extract green-- instead of "rooibos extract, green"; Line 18 should read --wolfberry-- instead of "wolf erry"; Line 37 should read --embodiments of this invention include-- instead of "embodiments of this invention, include"; Line 39 should read --resveratrol-- instead of "reservatrol"; Line 65 should read --refers to any polyunsaturated fatty acid-- instead of "any polyunsaturated fatty acid".

Column 25, Line 17 should read --vitamin B12-- instead of "vitamin B 12".

Column 26, Line 58 should read --body, causes-- instead of "body causes"; Line 61 should read --resorcylic acid lactones-- instead of "resorcyclic acid lactones".

Column 27, Line 29 should read --those of ordinary skill-- instead of "those or ordinary skill"; Line 41 should read --ascertain-- instead of "acertain"; Line 44 should read --steviol-- instead of "teviol".

Column 28, Line 23 should read --(including prodrugs thereof). Excipients include-- instead of "(including prodrugs thereof. Excipients included"; Line 57 should read --anti-glaucoma-- instead of "anti-gluacoma" and --cerumenolytics-- instead of "ceruminolytics"; Line 58 should read --antitussives-- instead of "antitussive"; Line 62 should read --anticholinesterases-- instead of "anticholinesterase"; Line 64 should read --luteinizing hormone-- instead of "luteinizings hormones", --progestogens-- instead of "progestogen" and --dopamine agonists-- instead of "dopamine agonist"; Line 65 should read --prostaglandins-- instead of "prostaglandin"; Line 67 should read --antiprotozoals-- instead of "antiprotozoal".

Column 29, Line 17 should read --glidants-- instead of "glidiants" and --dioxide), surface active-- instead of "dioxide) surface active"; Line 22 should read --Sterotex®-- instead of "sterotes"; Line 33 should read --sweetener composition-- instead of "sweetener compositions".

Column 30, Line 8 should read --teeth whitening agents-- instead of "teeth-whitening agent"; Line 22 should read --gingivitis-- instead of "Gingiva"; Line 25 should read --stannous fluoride-- instead of "stannos fluoride"; Line 41 should read --are present-- instead of "is present"; Line 66 should read --and/or 4 can serve-- instead of "and/or 4 N can serve".

Column 31, Line 10 should read --jelutong-- instead of "jetulong" and --Gutta-percha, rubber,-- instead of "guttakay rubber".

Column 32, Line 56 should read --composition comprising steviol glycosides-- instead of "composition comprising comprising steviol glycosides".

Column 33, Line 15 should read --about 200 ppm to about 20,000 ppm-- instead of "about 200 to about 20,000 weight percent".

Column 34, Lines 45-46 should read --500 ppm. A method-- instead of "500 ppm A method"; Line 59 should read --tastant and-- instead of "tastant/and".

In the Claims

Column 38, Line 24 (Claim 1) should read --1. An aqueous composition, comprising a first and a second steviol glycoside,-- instead of "1. An aqueous composition, comprising a first and a second steviol glycosides,".

Column 40, Lines 66-67 (Claim 12) should read --a first and a second steviol glycoside,-- instead of "a first and a second steviol glycosides,".